US008497105B2

(12) United States Patent
Walther et al.

(10) Patent No.: US 8,497,105 B2
(45) Date of Patent: Jul. 30, 2013

(54) INTEGRATED SYSTEM AND PROCESS FOR BIOPRODUCT PRODUCTION

(75) Inventors: David C. Walther, Oakland, CA (US); Hendrik J. Meerman, Scotts Valley, CA (US); Stacy M. Burns-Guydish, Campbell, CA (US); Richard W. Wilson, Palo Alto, CA (US); Eamon T. Hogg, Decatur, GA (US); Gregory W. Luli, San Diego, CA (US); Robert Eckert, Auburn, WA (US)

(73) Assignee: Cobalt Technologies, Inc., Mountain View, CA (US)

( * ) Notice: Subject to any disclaimer, the term of this patent is extended or adjusted under 35 U.S.C. 154(b) by 327 days.

(21) Appl. No.: 12/823,092

(22) Filed: Jun. 24, 2010

(65) Prior Publication Data

US 2010/0330633 A1 Dec. 30, 2010

Related U.S. Application Data

(60) Provisional application No. 61/221,007, filed on Jun. 26, 2009, provisional application No. 61/221,474, filed on Jun. 29, 2009, provisional application No. 61/278,932, filed on Oct. 13, 2009.

(51) Int. Cl.
C12P 1/04 (2006.01)
(52) U.S. Cl.
USPC .............................. 435/160; 435/41; 435/132
(58) Field of Classification Search
None
See application file for complete search history.

(56) References Cited

U.S. PATENT DOCUMENTS

| | | | |
|---|---|---|---|
| 2,487,884 A | 11/1949 | Lunt | |
| 3,004,089 A | 10/1961 | Hutto | |
| 3,390,057 A | 6/1968 | Day | |
| 3,875,019 A | 4/1975 | Cocuzza et al. | |
| 4,186,058 A | 1/1980 | Katz et al. | |
| 4,282,067 A | 8/1981 | Katz et al. | |
| 4,309,254 A | 1/1982 | Dahlstrom et al. | |
| 4,319,964 A | 3/1982 | Katz et al. | |
| 4,326,032 A | 4/1982 | Grove | |
| 4,356,196 A | 10/1982 | Hultquist | |
| 4,398,920 A | 8/1983 | Guibet et al. | |
| 4,424,275 A | 1/1984 | Levy | |
| 4,427,453 A | 1/1984 | Reitter | |
| 4,440,601 A | 4/1984 | Katz et al. | |
| 4,443,542 A | 4/1984 | Hayashida et al. | |
| 4,520,104 A | 5/1985 | Heady et al. | |
| 4,539,293 A | 9/1985 | Bergstrom et al. | |
| 4,560,658 A | 12/1985 | Datta et al. | |
| 4,568,643 A | 2/1986 | Levy | |
| 4,600,477 A | 7/1986 | Higashi et al. | |
| 4,615,769 A | 10/1986 | Horigome et al. | |
| 4,628,116 A | 12/1986 | Cenedella | |
| 4,649,112 A | 3/1987 | Datta et al. | |
| 4,671,856 A | 6/1987 | Sears | |
| 4,757,010 A | 7/1988 | Hermann et al. | |
| 4,769,113 A | 9/1988 | Sears | |
| 4,777,135 A | 10/1988 | Husted et al. | |
| 4,869,067 A | 9/1989 | Sears | |
| 4,902,197 A | 2/1990 | Rhodes et al. | |
| 4,919,592 A | 4/1990 | Sears et al. | |
| 4,978,429 A | 12/1990 | Sears et al. | |
| 5,063,156 A | 11/1991 | Glassner et al. | |
| 5,124,004 A | 6/1992 | Greithlein et al. | |
| 5,192,673 A | 3/1993 | Jain et al. | |
| 5,210,032 A | 5/1993 | Kashket | |
| 5,229,285 A | 7/1993 | Kajiyama et al. | |
| 5,292,658 A | 3/1994 | Cormier et al. | |
| 5,411,594 A | 5/1995 | Brelsford | |
| 5,418,155 A | 5/1995 | Cormier et al. | |
| 5,491,084 A | 2/1996 | Chalfie et al. | |
| 5,563,069 A | 10/1996 | Yang | |
| 5,595,893 A | 1/1997 | Pometto et al. | |
| 5,597,453 A | 1/1997 | Sears | |
| 5,604,123 A | 2/1997 | Kazami et al. | |
| 5,618,722 A | 4/1997 | Zenno et al. | |
| 5,625,048 A | 4/1997 | Tsien et al. | |
| 5,641,641 A | 6/1997 | Wood | |
| 5,650,135 A | 7/1997 | Contag et al. | |
| 5,650,289 A | 7/1997 | Wood | |
| 5,670,356 A | 9/1997 | Sherf et al. | |
| 5,753,474 A | 5/1998 | Ramey | |
| 5,755,967 A | 5/1998 | Meagher et al. | |
| 5,777,079 A | 7/1998 | Tsien et al. | |
| 5,804,387 A | 9/1998 | Cormack et al. | |
| 5,874,304 A | 2/1999 | Zolotukhin et al. | |

(Continued)

FOREIGN PATENT DOCUMENTS

EP 0922106 B1 9/2005
EP 2072621 6/2009

(Continued)

OTHER PUBLICATIONS

Almeida, et al. Increased tolerance and conversion of inhibitors in lignocellulosic hydrolysates by *Saccharomyces cerevisiae*. Journal of Chemical Technology & Biotechnology. 2007;82(4):340-349.
Alsaker, et al. Transcriptional analysis of spo0A overexpression in *Clostridium acetobutylicum* and its effect on the cell's response to butanol stress. J Bacteriol. Apr. 2004;186(7):1959-71.
Andersch, et al. Level of enzymes involved in acetate, butyrate, acetone and butanol formation by *Clostridium acetobutylicum*. Eur J Appl Microbiol Biotechnol. 1983; 18: 327-32.
Araki, et al. Continuous fermentation by butanol-isopropanol by Butanol-Isopropanol Producing Microorganisms Immobilized by Ca-Alginate. J Soc Fermentation and Bioengineering. 1993. 71(1):9-14. (in Japanese with English abstract).

(Continued)

*Primary Examiner* — James Martinell
(74) *Attorney, Agent, or Firm* — Wilson Sonsini Goodrich & Rosati

(57) ABSTRACT

Processes and systems for production of bioproducts such as biofuels are provided. The bioproduct production processes and systems utilize pretreatment of a carbohydrate-containing feedstock to produce soluble sugar molecules and continuous conversion of the pretreated feedstock to a bioproduct by an immobilized fermenting microorganism.

40 Claims, 12 Drawing Sheets

U.S. PATENT DOCUMENTS

| | | | |
|---|---|---|---|
| 5,968,321 | A | 10/1999 | Sears |
| 5,968,738 | A | 10/1999 | Anderson et al. |
| 6,043,392 | A | 3/2000 | Holtzapple et al. |
| 6,066,476 | A | 5/2000 | Tsien et al. |
| 6,146,826 | A | 11/2000 | Chalfie et al. |
| 6,358,717 | B1 | 3/2002 | Blaschek et al. |
| 6,436,682 | B1 | 8/2002 | Bryan et al. |
| 6,617,156 | B1 | 9/2003 | Doucette-stamm et al. |
| 6,638,398 | B1 | 10/2003 | Ramm-schmidt et al. |
| 6,673,596 | B1 | 1/2004 | Sayler et al. |
| 6,733,997 | B1 | 5/2004 | Ding et al. |
| 6,737,245 | B1 | 5/2004 | Francis et al. |
| 6,841,158 | B1 | 1/2005 | Cotten et al. |
| 6,919,186 | B2 | 7/2005 | Stubbs et al. |
| 6,955,892 | B2 | 10/2005 | Lin et al. |
| 7,005,511 | B2 | 2/2006 | Tsien et al. |
| 7,056,728 | B2 | 6/2006 | Francis et al. |
| 7,090,976 | B2 | 8/2006 | Anderson et al. |
| 7,109,005 | B2 | 9/2006 | Eroma et al. |
| 7,179,644 | B2 | 2/2007 | Farmer |
| 7,300,792 | B2 | 11/2007 | Gupta et al. |
| 7,354,743 | B2 | 4/2008 | Vlasenko et al. |
| 7,572,353 | B1 | 8/2009 | Vander Griend |
| 2003/0044951 | A1 | 3/2003 | Sporleder et al. |
| 2004/0142356 | A1 | 7/2004 | Patterson et al. |
| 2004/0248250 | A1 | 12/2004 | Nakai et al. |
| 2005/0072662 | A1 | 4/2005 | Holtzapple et al. |
| 2005/0080248 | A1 | 4/2005 | Caldwell et al. |
| 2005/0089979 | A1 | 4/2005 | Ezeji et al. |
| 2005/0176121 | A1 | 8/2005 | Takeshita et al. |
| 2005/0191723 | A1 | 9/2005 | Otte et al. |
| 2005/0285129 | A1 | 12/2005 | Jackson et al. |
| 2006/0010506 | A1 | 1/2006 | Otte et al. |
| 2006/0029958 | A1 | 2/2006 | Sakanyan et al. |
| 2006/0195935 | A1 | 8/2006 | Otte et al. |
| 2006/0263882 | A1 | 11/2006 | Fazio et al. |
| 2007/0137996 | A1 | 6/2007 | Beckman |
| 2007/0215453 | A1 | 9/2007 | Eddington |
| 2007/0218541 | A1 | 9/2007 | Denney et al. |
| 2007/0259411 | A1 | 11/2007 | Bramucci et al. |
| 2008/0078205 | A1 | 4/2008 | Cuellar et al. |
| 2008/0248540 | A1 | 10/2008 | Yang |
| 2008/0293086 | A1 | 11/2008 | Contag |
| 2008/0299633 | A1 | 12/2008 | Rush |
| 2009/0081715 | A1 | 3/2009 | Burns-Guydish et al. |
| 2009/0155869 | A1 | 6/2009 | Buelter et al. |
| 2011/0129887 | A1 | 6/2011 | Contag et al. |

FOREIGN PATENT DOCUMENTS

| | | |
|---|---|---|
| JP | 63109766 A | 5/1988 |
| WO | WO 81/01012 A1 | 4/1981 |
| WO | WO 2007/041269 A2 | 4/2007 |
| WO | WO 2007/130560 A2 | 11/2007 |
| WO | WO 2008/006038 A2 | 1/2008 |
| WO | WO 2008/013996 A2 | 1/2008 |
| WO | WO 2007/041269 A3 | 6/2008 |
| WO | WO 2007/130560 A3 | 7/2008 |
| WO | WO 2008/082726 A2 | 7/2008 |
| WO | WO 2008/006038 A3 | 8/2008 |
| WO | WO 2008/013996 A3 | 10/2008 |
| WO | WO 2008/082726 A3 | 11/2008 |
| WO | WO 2009/033114 A2 | 3/2009 |
| WO | WO 2009/033114 A3 | 5/2009 |
| WO | WO 2009/120806 A2 | 10/2009 |
| WO | WO 2009/120806 A3 | 2/2010 |
| WO | WO 2010/027531 A1 | 3/2010 |
| WO | WO 2011/003962 A2 | 1/2011 |
| WO | WO 2011/003962 A3 | 3/2011 |

OTHER PUBLICATIONS

Baer, et al. Effect of Butanol Challenge and Temperature on Lipid Composition and Membrane Fluidity of Butanol-Tolerant *Clostridium acetobutylicum*. Appl Environ Microbiol. Dec. 1987;53(12):2854-2861.

Bahl, et al. Continuous production of acetone and butanol by *Clostridium acetobutylicum* in a two-stage phosphate limited chemostat. Eur J Appl Microbiol Biotechnol. 1982; 15: 201-5.

Bahl, et al. Nutritional factors affecting the ratio of solvents produced by *Clostridium acetobutylicum*. Appl Environ Microbiol 1986; 52(1): 169-72.

Bahl, et al. Parameters affecting solvent production by *Clostridium acetobutylicum* in continuous culture. In: Wang, et al., ed. Biotechnology and Bioengineering Symposium No. 14, Sixth Symposium on Biotechnology for Fuels and Chemicals. New York, NY: John, (1984) pp. 215-223.

Beesch, S. Acetone-butanol fermentation of starches. Appl Microbiol. 1953; 1: 85-96.

Beesch, S. Acetone-butanol fermentation of sugars. Eng Proc Dev. 1952; 44: 1677-82.

Bermejo, et al. Expression of *Clostridium acetobutylicum* ATCC 824 genes in *Escherichia coli* for acetone production and acetate detoxification. Appl Environ Microbiol. Mar. 1998;64(3):1079-85.

Blevins, et al. Adaptation of a luciferase gene reporter and lac expression system to *Borrelia burgdorferi*. Appl Environ Microbiol. Mar. 2007;73(5):1501-13.

Boynton, et al. Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824. J Bacteriol. 1996; 178(11): 3015-24.

Boynton, et al. Cloning, sequencing, and expression of genes encoding phosphotransacetylase and acetate kinase from *Clostridium acetobutylicum* ATCC 824. Appl Environ Microbiol. 1996; 62(8): 2758-66.

Bräu, et al. Cloning and expression of the structural gene for pyruvate decarboxylase of *Zymomonas mobilis* in *Escherichia coli*. Arch Microbiol. 1986; 144: 296-301.

Bringer-Meyer, et al. Pyruvate decarboxylase from *Zymomonas mobilis*. Isolation and partial characterization. Arch Microbiol. 1986; 146(2): 105-10.

Burchhardt, et al. Cloning and analysis of the β-galactosidase-encoding gene from *Clostridium thermosulferogenes* EM1. Gene. 1991; 106: 13-9.

Chakraborty, et al. Coordinate regulation of virulence genes in *Listeria monocytogenes* requires the product of the prfA gene. J Bacteriol. 1992; 174(2): 568-74.

Chalfie, et al. Green fluorescent protein as a marker for gene expression. Science. 1994; 263(5148): 802-5.

Chin, et al. Fedbatch operation using *Clostridium acetobutylicum* suspension culture as biocatalyst for enhancing hydrogen production. Biotechnol Prog. Mar.-Apr. 2003;19(2):383-8.

Contag, et al. Cloning of a lactate dehydrogenase gene from *Clostridium acetobutylicum* B643 and expression in *Escherichia coli*. Appl Environ Microbiol. 1990; 56(12):3760-5.

Conway, et al. Cloning and sequencing of the alcohol dehydrogenase II gene from *Zymomonas mobilis*. J Bacteriol. 1987; 169(6): 2591-7.

Cormack, et al. Yeast-enhanced green fluorescent protein (yEGFP)a reporter of gene expression in *Candida albicans*. Microbiology. 1997; 143(Pt 2): 303-11.

Davies, et al. Studies of the acetone-butyl alcohol fermentation. I. Nutritional and other factors involved in the preparation of active suspensions of *Clostridium acetobutylicum*. Biochem J. 1941; 35: 1320-31.

Davison, et al. Continuous direct solvent extraction of butanol in a fermenting fluidized-bed bioreactor with immobilized *Clostridium acetobutylicum*. In: Applied biochemistry and biotechnology.1993, vol. 39-40 (27 ref.), pp. 415-426.

Davison, et al. Novel immobilized-biocatalyst bioreactors for productioin of fuels and chemicals. In: ACS National Meeting & Exposition (Anaheim), 1999, vol. 42(2), pp. 215-218.

De Wet, et al. Cloning of firefly luciferase cDNA and the expression of active luciferase in *Escherichia coli*. Proc Natl Acad Sci USA. 1985; 82(23): 7870-3.

De Wet, et al. Firefly luciferase gene: structure and expression in mammalian cells. Mol Cell Biol. 1987; 7: 725-37.

Doyle, et al. Expression of firefly luciferase in *Candida albicans* and its use in the selection of stable transformants. Microb Pathog. Feb. 2006;40(2):69-81.

Durre, et al. Transcriptional regulation of solventogenesis in *Clostridium acetobutylicum*. J Mol MiCrobiol Biotechnol. 2002; 4: 295-300.

European search report dated Oct. 8, 2010 for Application No. 07842375.3.

Ezeji, et al. Bioproduction of butanol from biomass: from genes to bioreactors. Cuff Opin Biotechnol. Jun. 2007;18(3):220-7.

Ezeji, et al. Butanol fermentation research: upstream and downstream manipulations. Chem Rec. 2004;4(5):305-14.

Feustel, et al. Characterization and development of two reporter gene systems for *Clostridium acetobutylicum*. Appl Environ Microbiol. 2004; 70: 798-803.

Fey, et al. Green fluorescent protein production in the cellular slime molds *Polysphondylium pallidum* and *Dictyostelium discoideum*. Gene. 1995; 165(1): 127-30.

Fischer, et al. Cloning, sequencing, and molecular analysis of the sol operon of *Clostridium acetobutylicum*, a chromosomal locus involved in solventogenesis. J Bacteriol. 1993; 175(21): 6959-69.

Fischer, et al. Selection and optimization of microbial hosts for biofuels production. Metab Eng. Nov. 2008;10(6):295-304.

Fontaine, et al. Molecular characterization and transcriptional analysis of adhE2, the gene encoding the NADH-dependent aldehyde/alcohol dehydrogenase responsible for butanol production in alcohologenic cultures of *Clostridium acetobutylicum* ATCC 824. J Bacteriol. 2002; 184(3): 821-30.

Frackman, et al. Cloning, organization, and expression of the bioluminescence genes of *Xenorhabdus luminescens*. J Bacteriol. 1990; 172(10): 5767-73.

Frick, et al. Continuous acetone-butanol production with free and immobilized *Clostridium acetobutylicum*. In: Applied microbiology and biotechnology. 1986, vol. 25, No. 3, pp. 186-193.

George, et al. Acetone, isopropanol, and butanol production by *Clostridium beijernickii* (syn. *Clostridium butylicum*) and *Clostridium aurantibutyricum*. Appl Environ Microbiol. 1983; 45: 1160-3.

Gerischer, et al. Cloning, sequencing, and molecular analysis of the acetoacetate decarboxylase gene region from *Clostridium acetobutylicum*. J Bacteriol. 1990; 172(12): 6907-18.

Gerischer, et al. mRNA analysis of the adc gene region of *Clostridium acetobutylicum* during the shift to solventogenesis. J Bacteriol. 1992; 174: 426-33.

Girbal, et al. Development of a sensitive gene expression reporter system and an inducible promoter-repressor system for *Clostridium acetobutylicum*. Appl Environ Microbiol. 2003; 69: 4985-8.

Girbal, et al. Regulation of metabolic shifts in *Clostridium acetobutylicum* ATCC824. FEMS Microbiol Rev. 1995; 17: 287-97.

Gottschalk. Bacterial Metabolism, 2nd Ed. New York, NY: Springer-Verlag; 1986, pp. xi-xiii.

Gottwald, et al. Formation of n-butanol from D-glucose by strains of *Clostridium tetanomorphum* group. Appl Environ Microbiol. 1984; 48: 573-6.

Gupta, et al. Expression of the *Photorhabdus luminescens* lux genes (luxA, B, C, D, and E) in *Saccharomyces cerevisiae*. FEMS Yeast Res. Dec. 2003;4(3):305-13.

Harris, et al. Characterization of recombinant strains of the *Clostridium acetobutylicum* butyrate kinase inactivation mutant: Need for new phenomenological models for solventogenesis and butanol inhibition? Biotechnol Bioeng. Jan. 5, 2000;67(1):1-11.

Hartmanis, et al. Uptake and activation of acetate and butyrate in *Clostridium acetobutylicum*. Appl Microbiol Biotechnol. 1984; 20: 66-71.

Hausding, et al. Inhibition of small G proteins of the rho family by statins or *Clostridium difficile* toxin B enhances cytokine-mediated induction of NO synthase II. Br J Pharmacol. Oct. 2000;131(3):553-61.

Hermann, et al. Isolation and characterization of butanol-resistant mutants of *Clostridium acetobutylicum*. Appl Environ Microbiol. Nov. 1985;50(5):1238-43.

Hung, et al. Continuous perfusion microfluidic cell culture array for high-throughput cell-based assays. Biotechnol Bioeng. Jan. 5, 2005;89(1):1-8.

Hunter, et al. Formaldehyde metabolism by *Escherichia coli*. Carbon and solvent deuterium incorporation into glycerol, 1,2-propanediol, and 1,3-propanediol. Biochemistry. 1985; 24(15): 4148-55.

Hüsemann, et al. Solventogenesis in *Clostridium acetobutylicum* fermentations related to carboxylic-acid and proton concentrations. Biotechnol Bioeng. 1988; 32: 843-52.

Ingram, et al. Expression of different levels of ethanologenic enzymes from *Zymomonas mobilis* in recombinant strains of *Escherichia coli*. Appl Environ Microbiol. 1988; 54(2): 397-404.

Ingram, et al. Genetic engineering of ethanol production in *Escherichia coli*. Appl Environ Microbiol, 1987; 53(10): 2420-5.

International search report dated Apr. 13, 2009 for PCT Application No. US2008/75515.

International search report dated Jan. 6, 2010 for PCT Application No. US2009/40050.

International search report dated Oct. 19, 2009 for PCT Application No. US2009/036868.

International search report dated Dec. 18, 2009 for PCT Application No. US2009/038300.

International search report dated Aug. 23, 2010 for PCT Application No. US10/39873.

International search report dated Sep. 16, 2008 for PCT Application No. US07/78321.

Jones, et al. Acetone-butanol fermentation revisited. Microbio. Rev. 1986; 50: 484-524.

Junelles, et al. Effect of pyruvate on glucose metabolism in *Clostridium acetobutylicum*. Biochimie. 1987; 69: 1183-90.

Keis, et al. Emended descriptions of *Clostridium acetobutylicum* and *Clostridium beijerinckii*, and descriptions of *Clostridium saccharoperbutylacetonicum* sp. nov. and *Clostridium saccharobutylicum* sp. nov. Int J Syst Evol Microbiol. Nov. 2001;51(Pt 6):2095-103.

Killeffer, D. Butanol and acetone from corn. A description of the fermentation process. Ind Eng Chem. 1927; 19: 46-50.

Klinke, et al. Inhibition of ethanol-producing yeast and bacteria by degradation products produced during pre-treatment of biomass. Applied Microbiology and Biotechnology. 2004;66(1):10-26.

Knoshaug, et al. Butanol Tolerance in a Selection of Microorganisms. Appl Biochem Biotechnol. Dec. 17, 2008. (8 pages).

Largier, et al. Immobilized *Clostridium acetobutylicum* P262 Mutants for Solvent Production. Appl Environ Microbiol. Aug. 1985;50(2):477-81.

Lee, et al. Fermentative butanol production by *Clostridia*. Biotechnol Bioeng. Oct. 1, 2008;101(2):209-28.

Lee. Biological conversion of lignocellulosic biomass to ethanol. Journal of Biotechnology. 1997;56(1):1-24.

Liu, et al. Genomic adaptation of ethanologenic yeast to biomass conversion inhibitors. Journal Applied Microbiology and Biotechnology. 2006;73(1): 27-36.

Lopez-Contreras, A. Utilisation of saccharides in extruded domestic organic waste by *Clostridium acetobutylicum* ATCC 824 for production of acetone, butanol, and ethanol. Appl Microbiol Biotechnol. 2000; 54: 162-7.

Martin, et al. Engineering a mevalonate pathway in *Escherichia coli* for production of terpenoids. Nature Biotech. 2003; 21: 796-802.

McCutchan, et al. The Butanol-Acetone Fermentations. Industrial Fermentations, Underkofler, et al., eds. New York, NY: Chemical Publishing. 1954. 347-388.

McNeil, et al. Effect of temperature upon growth rate and solvent production in batch cultures of *Clostridium acetobutylicum*. Biotech Lett. 1985; 7: 499-502.

Mermelstein, et al. Expression of cloned homologous fermentative genes in *Clostridium acetobutylicum* ATCC 824. Biotechnology (NY). 1992; 10(2): 190-5.

Miller, et al. An improved GFP cloning cassette designed for prokaryotic transcriptional fusions. Gene. 1997; 191(2); 149-53.

Miyamoto, et al. Nucleotide sequence of the LuxC gene and the upstream DNA from the bioluminescent system of *Vibrio harveyi*. Nucleic Acids Res. 1988;16(4): 1551-62.

Mosier, et al. Features of promising technologies for pretreatment of lignocellulosic biomass. Bioresource Technology. 2005;96(6):673-686.

Nair, et al. Molecular characterization of an aldehyde/alcohol dehydrogenase gene from *Clostridium acetobutylicum* ATCC 824. J Bacteriol. 1994; 176(3): 871-85.

Neale, et al. Nucleotide sequence of the pyruvate decarboxylase gene from *Zymomonas mobilis*. Nucl Acids Res. 1987; 15(4): 1753-61.

Ohta, et al. Genetic improvement of *Escherichia coli* for ethanol production: chromosomal integration of *Zymomonas mobilis* genes encoding pyruvate decarboxylase and alcohol dehydrogenase II. Appl Environ Microbiol. 1991; 57(4): 893-900.

Palmqvist, et al. Fermentation of lignocellulosic hydrolysates. II: inhibitors and mechanisms of inhibition. Bioresource Technology. 2000;74(1):25-33.

Paredes, et al. Transcriptional organization of the *Clostridium acetobutylicum* genome. Nuc Acids Res. 2004; 32(6): 1973-81.

Patterson, et al. Codon optimization of bacterial luciferase (lux) for expression in mammalian cells. J Ind Microbiol Biotechnol. Mar. 2005;32(3):115-23.

Petersen, et al. Molecular cloning of an alcohol (butanol) dehydrogenase gene cluster from *Clostridium acetobutylicum* ATCC 824. J Bacteriol. 1991; 173: 1831-4.

Phillips-Jones, et al. Use of a lux reporter system for monitoring rapid changes in alpha-toxin gene expression in Clostridium perfringens during growth. FEMS Microbiol Lett. Jul. 1, 2000;188(1):29-33.

Phillips-Jones, M. Bioluminescence (lux) expression in the anaerobe *Clostridium perfringens*. FEMS Microbiol Lett. Feb. 1, 1993;106(3):265-70.

Prendergast, et al. Chemical and physical properties of aequorin and the green fluorescent protein isolated from *Aequorea forskalea*. Biochemistry. 1978; 17(17): 3448-53.

Quixley, et al. Construction of a reporter gene vector for *Clostridium beijerinckii* using a *Clostridium endoglucanase* gene. J Mol Microbiol Biotechnol. 2000; 2: 53-7.

Quratulain, et al. Development and characterization of butanol—Resistant strain of *Clostridium acetobutylicum* in molasses medium. Folia Microbiologica. 1995;40(5):467-471.

Qureshi, et al. Biofilm reactors for industrial bioconversion processes: employing potential of enhanced reaction rates. Microb Cell Fact. Aug. 25, 2005;4:24-45. (21 pages).

Qureshi, et al. Butanol production from corn fiber xylan using *Clostridium acetobutylicum*. Biotechnol Prog. May-Jun. 2006;22(3):673-80.

Qureshi, et al. Continuous production of acetone-butanol-ethanol using immobilized cells of *Clostridium acetobutylicum* and integration with product removal by liquid-liquid extraction. Journal of Fermentation and Bioengineering. 1995;80(2):185-189.

Qureshi, et al. Continuous solvent production by *Clostridium beijerinckii* BA101 immobilized by adsorption onto brick. In: World journal of microbiology & biotechnology. 2000, vol. 16, No. 4, pp. 377-382.

Reardon, et al. In Situ Fluorescence Monitoring of Immobilized *Clostridum acetobutylicum*. Biotechnol Lett. 1986; 8(11): 817-822.

Rogers, et al. *Clostridium acetobutylicum* mutants that produce butyraldehyde and altered quantities of solvents. Appl Enviorn Microbiol. 1987; 53: 2761-6.

Rogers, P. Genetics and biochemistry of *Clostridium* relevant to development of fermentation process. Adv Appl Microbiol. 1986; 31: 1-60.

Sauer, et al. Differential induction of genes related to solvent formation during the shift from acidogenesis to solventogenesis in continuous culture of *Clostridium acetobutylicum*. FEMS Microbiol Lett. 1995; 125: 115-20.

Scotcher, et al. Sequences affecting the regulation of solvent production in *Clostridium acetobutylcum*. J. Ind. Microbiol. 2003; 30:414-420.

Stim-Herndon, et al. Characterization of an acetyl-CoA C-acetyltransferase (thiolase) gene from *Clostridium acetobutylicum* ATCC 824. Gene. 1995; 154(1): 81-5.

Straight, et al. GFP tagging of budding yeast chromosomes reveals that proteinprotein interactions can mediate sister chromatid cohesion. Curr Biol. 1996; 6(12): 1599-608.

Syed, et al. Enhanced butanol production by mutant strains of *Clostridium acetobutylicum* in molasses medium. Turkish Journal of Biochemistry. 2008; 33(1):25-30.

Tashiro, et al. High butanol production by *Clostridium saccharoperbutylacetonicum* N1-4 in fed-batch culture with pH-Stat continuous butyric acid and glucose feeding method. J Biosci Bioeng. 2004;98(4):263-8.

Tatsumi, et al. Molecular cloning and expression in *Escherichia coli* of a cDNA clone encoding luciferase of a firefly, *Luciola lateralis*. Biochim Biophys Acta. 1992;1131(2): 161-5.

Thormann, et al. Control of butanol formation in *Clostridium acetobutylicum* by transcriptional activation. J Bacteriol. Apr. 2002;184(7):1966-73.

Tolan, et al. Fermentation of d-xylose and 1-arabinose to ethanol by *Erwinia chrysanthemi*. Appl Environ Microbiol. 1987; 53(9): 2033-2038.

Tomas, et al. Transcriptional analysis of butanol stress and tolerance in *Clostridium acetobutylicum*. J Bacteriol. Apr. 2004;186(7):2006-18.

Tummula, et al. Development and characterization of a gene expression reporter system for *Clostridium acetobutylicum* ATCC 824. Appl Environ Microbiol. 1999; 65: 3793-9.

UK combined office action dated Jan. 18, 2008 and search report for Application No. GB0718077.1.

UK combined office action dated Jul. 27, 2010 and search report dated Jan. 17, 2008 for Application No. GB0718077.1.

UK office action dated Aug. 19, 2010 for Application No. GB0906322.3.

Walter, et al. Molecular characterization of two *Clostridium acetobutylicum* ATCC 824 butanol dehydrogenase isozyme genes. J Bacteriol. 1992; 174(22): 7149-58.

Ward, et al. An energy transfer protein in coelenterate bioluminescence. Characterization of the Renilla green-fluorescent protein. J Biol Chem. 1979; 254(3): 781-8.

Ward, et al. Energy-transfer via protein-protein interaction in renilla bioluminescence. Photochemistry and Photobiology. 1978; 27: 389-96.

Ward, et al. Reversible denaturation of Aequorea green-fluorescent protein: physical separation and characterization of the renatured protein. Biochemistry. 1982; 21(19): 4535-40.

Winzer, et al. Differential regulation of two thiolase genes from*Clostridium acetobutylicum* DSM 792. J Mol Microbiol Biotechnol. 2000; 2(4): 531-41.

Wood, et al. Complementary DNA coding click beetle luciferases can elicit bioluminescence of different colors. Science. 1989; 244: 700-2.

Xi, et al. Cloning and nucleotide sequences of lux genes and characterization of luciferase of *Xenorhabdus luminescens* from a human wound. J Bacteriol. 1991; 173: 1399-405.

Yamada, et al. Production of glycerol from methanol by a mutant strain of *Candida boidinii* No. 2201. Agric Biol Chem. 1989; 53(2): 541-3.

Yu, et al. Differential induction of β-galactosidase and phospho-β-galactosidase activities in the fermentation of whey permeate by *Clostridium acetobutylicum*. Appl Microbiol Biotechnol. 1987; 26: 254-7.

Zaldivar, et al. Fuel ethanol production from lignocellulose: a challenge for metabolic engineering and process integration. Journal Applied Microbiology and Biotechnology. 2001;56(1-2):17-34.

Craney, et al. A synthetic luxCDABE gene cluster optimized for expression in high-GC bacteria. Nucleic Acids Res. 2007;35(6):e46. Epub Mar. 1, 2007.

European search report (supplemental) dated Nov. 23, 2010 for Application No. 08829763.5.

European search report and search opinion dated Nov. 4, 2010 for Application No. 08829763.5.

International search report dated Jun. 28, 2010 for PCT Application No. US2010/32463.

International search report dated Aug. 3, 2010 for PCT Application No. US2010/032462.

Meighen, E. Bacterial bioluminescence: organization, regulation, and application of the lux genes. Faseb J. Aug. 1993;7(11):1016-22.

U.S. Appl. No. 13/353,233, filed Jan. 18, 2012, Contag.

U.S. Appl. No. 13/441,786, filed Apr. 4, 2012, Burns-Guydish et al.

U.S. Appl. No. 13/061,898, filed Mar. 2, 2011, Burns-Guydish et al.

Office action dated Sep. 28, 2010 for U.S. Appl. No. 11/853,681.

UK office action dated Mar. 31, 2011 for Application No. GB0906322.3.

Office action dated Jul. 19, 2011 for U.S. Appl. No. 11/853,681.

Biebl. Fermentation of glycerol by *Clostridium pasteurianum*—batch and continuous culture studies. J Ind Microbiol Biotechnol. Jul. 2001;27(1):18-26.

Chiao, et al. History of the acetone-butanol-ethanol fermentation industry in China: development of continuous production technology. J Mol Microbiol Biotechnol. 2007;13(1-3):12-4.

Forsberg. Production of 1,3-Propanediol from Glycerol by *Clostridium acetobutylicum* and Other *Clostridium* Species. Appl Environ Microbiol. Apr. 1987;53(4):639-43.

Gonzalez-Pajuelo, et al. Microbial conversion of glycerol to 1,3-propanediol: physiological comparison of a natural producer, *Clostridium butyricum* VPI 3266, and an engineered strain, *Clostridium acetobutylicum* DG1(pSPD5). Appl Environ Microbiol. Jan. 2006;72(1):96-101.

Ni, et al. Recent progress on industrial fermentative production of acetone-butanol-ethanol by *Clostridium acetobutylicum* in China. Appl Microbiol Biotechnol. Jun. 2009;83(3):415-23. Epub May 9, 2009.

Office action dated Jul. 13, 2011 for EP Application No. 07842375.3.

Sun, et al. The Acetone-Butanol (ABE) Fermentation Industries in China. Accessed Sep. 2, 2011. services.bepress.com/cgi/viewcontent.cgi?article=1006&context=eci/bioenergy_i.

Zverlov, et al. Bacterial acetone and butanol production by industrial fermentation in the Soviet Union: use of hydrolyzed agricultural waste for biorefinery. Appl Microbiol Biotechnol. Aug. 2006;71(5):587-97. Epub May 10, 2006.

Huang, et al. Continuous production of butanol by *Clostridium acetobutylicum* immobilized in a fibrous bed reactor. Appl Biochem and Biotechnol. 2004; 113-116:887-898.

Office action dated Oct. 7, 2011 for U.S. Appl. No. 12/205,845.

Office action dated Dec. 29, 2011 for U.S. Appl. No. 12/936,611.

UK office action dated Sep. 30, 2011 for Application No. GB0906322.3.

U.S. Appl. No. 13/866,884, filed Apr. 19, 2013, Contag et al.

Chang, et al. Kinetics of butanol fermentation by *Clostridium acetobutylicum* in multiple-step fibrous bed bioreactor—BIOT 388. Aug. 20, 2008, 236th ACS National Meeting. Phildelphia, PA.

European office action dated Oct. 24, 2012 for EP 07842375.3.

European office action dated Nov. 29, 2012 for EP 09730267.3.

European search report and opinion dated Mar. 16, 2012 for EP Application No. 09811872.2.

European search report and search opinion dated Mar. 13, 2013 for EP Application No. 10792688.3.

European seasrch report and search opinion dated Apr. 3, 2012 for EP 09730267.3.

Gholizadeh, L. Thesis. Enhanced Butanol Production by Free and Immobilized *Clostridium* sp. Cells Using Butyric Acid as Co-Substrate. School of Engineering. University of Boras, School of Engineering. Aug. 12, 2009.

Huang, et al. Acetic acid production from fructose by *Clostridium formicoaceticum* immobilized in a fibrous-Bed bioreactor . Biotechnol Prog. Sep. 1998;14(5):800-6.

Liu, et al. Construction and characterization of ack deleted mutant of *Clostridium tyrobutyricum* for enhanced butyric acid and hydrogen production. Biotechnol Prog. Sep.-Oct. 2006;22(5):1265-75.

Office action dated May 7, 2012 for U.S. Appl. No. 12/936,611.

Office action dated Nov. 28, 2012 for CN Application No. 200980121678.2.

Ramey, et al. Production of Butyric Acid and Butanol from Biomass. Work performed under Contract No. DE-F-G02-00ER86106 for U.S. Department of Energy, Morgantown, WV. 2004.

Suwannakham, et al. Enhanced propionic acid fermentation by *Propionibacterium acidipropionici* mutant obtained by adaptation in a fibrous-bed bioreactor. Biotechnol Bioeng. Aug. 5, 2005;91(3):325-37.

Wu, et al. Extractive fermentation for butyric acid production from glucose by *Clostridium tyrobutyricum*. Biotechnol Bioeng. Apr. 5, 2003;82(1):93-102.

Yang, et al. Continuous propionate production from whey permeate using a novel fibrous bed bioreactor. Biotechnol Bioeng. May 1994;43(11):1124-30.

Zhang, et al. Continuous acetone-butanol-ethanol production by corn stalk immobilized cells. J Ind Microbiol Biotechnol. Aug. 2009;36(8):1117-21. doi: 10.1007/s10295-009-0582-3. Epub May 1, 2009.

Zhu, et al. Adaptation of *Clostridium tyrobutyricum* for enhanced tolerance to butyric acid in a fibrous-bed bioreactor. Biotechnol Prog. Mar.-Apr. 2003;19(2):365-72.

Zhu, et al. Construction and characterization of pta gene-deleted mutant of *Clostridium tyrobutyricum* for enhanced butyric acid fermentation. Biotechnol Bioeng. Apr. 20, 2005;90(2):154-66.

Zhu, Y. Dissertation. Enhanced Butyric Acid Fermentation by *Clostridium tyrobutyricum* Immobilized in a Fibrous-Bed Bioreactor. Graduate School of The Ohio State University. 2003.

INTEGRATED SYSTEM AND PROCESS FOR BIOPRODUCT PRODUCTION

CROSS-REFERENCE

This application claims the benefit of U.S. provisional application Nos. 61/221,007, filed Jun. 26, 2009, 61/221,474, filed Jun. 29, 2009, and 61/278,932, filed Oct. 13, 2009, all of which are incorporated herein by reference in their entireties.

FIELD OF THE INVENTION

The invention relates to production of a bioproduct, such as biobutanol, in a continuous microbial fermentation process.

BACKGROUND OF THE INVENTION

Butanol is a high quality fuel and fuel additive. Butanol can be mixed, stored and transported together with gasoline. It has more energy per gallon than ethanol, which translates into better fuel economy for consumers using butanol blends, and has lower vapor pressure than ethanol, which translates into less ground level pollution. Butanol's low vapor pressure makes it an attractive low volatility, oxygenated, blend component for refiners to use in complying with stringent vapor pressure specifications. Butanol can provide the oxygenate benefits of ethanol but without undue evaporative emissions, which are a significant source of air pollution, and at a potentially lower cost. Butanol is also more hydrophobic than ethanol, i.e., it has a higher tendency to repel water, and is more suitable for blending with gasoline. As such, butanol should be a highly desired component of Reformulated Gasoline Blendstock for Oxygenate Blending (RBOB) and California (CARBOB) fuel blendstock. Butanol is also expected to have a reduced life cycle emission of $CO_2$. Butanol blends should have no detrimental effects on modern fuel system elastomers, and corrosion and electrical conductivity are expected to be similar to gasoline.

Butanol can also be blended in concentrations in excess of 20% with diesel fuel. The benefits of addition of oxygenates to diesel fuel include the reduction in soot formation, CO, and unburned hydrocarbon emissions. Importantly, addition of butanol to diesel fuel in concentrations sufficient to realize these benefits retains the flammability rating (flash point) of the diesel fuel without oxygenate. This is a significant benefit to deployment and implementation.

Butanol is also widely used as an industrial chemical. It is used in the production of paints, plasticizers, and pesticides, as an ingredient in contact lens cleansers, cement, and textiles, and also as a flavoring in candy and ice cream. The global market for n-butanol was approximately 1 billion gallons in 2006; the U.S. market was approximately 300 million gallons, and is expected to grow approximately 2% per year.

Butanol is currently made from petroleum. Production costs are high and margins are low, and price trends generally track the price of oil and are heavily influenced by global economic growth.

There is a need for improved methods for production of butanol. In particular, methods for environmentally compatible, cost efficient, and energy efficient production of butanol would be desirable.

BRIEF SUMMARY OF THE INVENTION

Processes and systems for bioproduct production are provided.

In one aspect, a process is provided for producing a bioproduct, including continuously fermenting a microorganism in the presence of hydrolyzed feedstock of a carbohydrate-containing material. The microorganism is immobilized on a support in a bioreactor. Hydrolyzed feedstock is produced by hydrolysis of the feedstock, which produces carbohydrate molecules that serve as a carbon source for the microbial fermentation. The microorganism continuously converts the hydrolyzed feedstock into a bioproduct. In some embodiments, the feedstock is hydrolyzed continuously upstream from the bioreactor and the resulting hydrolyzed feedstock is fed continuously to the bioreactor for the duration of the fermentation. In one embodiment, the bioproduct is a biofuel (e.g., butanol, acetone, ethanol). In other embodiments, the bioproduct is a biochemical or a biochemical feedstock, i.e., a biochemical that may be derivatized or converted to another product, e.g., via chemical synthesis. In some embodiments, the bioproduct is a solvent, a biomolecule, an organic acid, an alcohol, a vitamin, a fatty acid, an aldehyde, a lipid, a long chain organic molecule, or a sugar alcohol.

In some embodiments, the hydrolyzed feedstock is fed continuously into multiple bioreactors arranged in parallel and/or in series, the fermentation occurs continuously in the multiple bioreactors, and the multiple bioreactors contain the same or different microorganism(s). In one embodiment, the hydrolyzed feedstock is fed continuously into multiple bioreactors arranged in parallel, the fermentation occurs continuously in the multiple bioreactors, and the multiple bioreactors contain the same or different microorganism(s). In another embodiment, the fermentation occurs continuously in multiple bioreactors that are arranged in series, the hydrolyzed feedstock is fed continuously into the first bioreactor in the series, and effluent from each bioreactor is fed to the next bioreactor downstream in the series. In some embodiments, evolved gas may be removed between series nodes during operation of the bioreactors.

In one embodiment, bioreactors are arranged in parallel trains in a hybrid series/parallel arrangement. For example, fermentation may proceed in multiple bioreactors that are arranged in a combination to optimize productivity, such as a primary reactor arranged in series with a train of parallel reactors, with hydrolyzed feedstock fed continuously into the first bioreactor in the series and effluent from each bioreactor fed to the next bioreactor downstream in the series.

In one embodiment, the duration of the fermentation is at least about 300 hours. In another embodiment, the duration of the fermentation is at least about 1000 hours.

In some embodiments, the feedstock is a cellulosic material, for example, a lignocellulosic material. In some embodiments, the feedstock contains cellulose and hemicellulose, e.g., lignocellulosic material or wood pulp. In some embodiments, the feedstock is wood selected from softwood, hardwood, or a combination thereof. In some embodiments, the feedstock is a lignocellulosic material in the form of wood chips, sawdust, saw mill residue, or a combination thereof. In some embodiments, the lignocellulosic material (e.g., wood chips sawdust, saw mill residue, or a combination thereof) is from a feedstock source that has been subjected to some form of disease or infestation in the growth and/or harvest production period. In one embodiment, the feedstock source is mountain pine beetle infested pine. In another embodiment, the feedstock source is sudden oak death syndrome infested oak, e.g., coastal live oak, tanoak, etc. In another embodiment, the feedstock source is Dutch elm disease infested elm. In other embodiments, the feedstock source is lignocellulosic material that has been damaged by drought or fire.

In some embodiments, lignocellulosic feedstock material is deconstructed prior to hydrolysis. Deconstruction may include one or more process selected from presteaming, mechanical grinding, and mechanical explosion. In some embodiments, the feedstock material is deconstructed prior to harvest by a natural or non-natural environmental condition, for example, drought, infestation, fire, and/or herbicide exposure. In some embodiments, the feedstock material may be deconstructed by a disease organism, for example, mountain pine beetle deconstruction of pine, sudden oak death syndrome deconstruction of oak, or Dutch elm disease deconstruction of elm. In some embodiments, lignocellulosic feedstock material is pretreated to remove extractives. The extractive removal pretreatment may include compression, water extraction, solvent extraction, alkaline extraction, enzymatic treatment, fungal treatment, oxygen treatment, or air drying. In some embodiments, the pretreatment to remove extractives may occur prior to or in conjunction with deconstruction.

In some embodiments, hydrolysis of a feedstock, such as a lignocellulosic feedstock, is performed by treatment with an acid. In some embodiments, the acid includes nitric acid, formic acid, acetic acid, phosphoric acid, hydrochloric acid, or sulfuric acid, or a combination thereof. In one embodiment, the hydrolysis is performed with nitric acid. In another embodiment, the hydrolysis is performed with a combination of nitric acid and acetic acid. In some embodiments, the feedstock contains acetyl groups and releases acetic acid, resulting in autohydrolysis of hemicellulose, which may then release more acetic acid. This autohydrolysis may be supplemented by addition of a mineral acid, or the amount of mineral acid required for hydrolysis of the feedstock may be reduced by "leveraging" the natural acetyl content in the feedstock.

In some embodiments, hydrolysis of a lignocellulosic feedstock is performed with nitric acid in a process including a first stage and a second stage, with the second stage hydrolysis performed at a higher temperature than the first stage. In some embodiments, performing hydrolysis at a higher temperature in the second stage decreases or prevents degradation of a desired intermediate product (e.g., monomeric sugar molecules). In some embodiments, the conditions in the first stage are chosen to achieve hydrolysis of at least about 70% of the hemicellulose in the feedstock, and the conditions in the second stage are chosen to achieve hydrolysis of at least about 40% of the cellulose in the feedstock. In some embodiments, the feedstock is a hardwood, the first stage hydrolysate comprises at least about 60% 5-carbon sugar and at least about 25% 6-carbon sugar, and the second stage hydrolysate comprises at least about 80% 6-carbon sugar. In some embodiments, the feedstock is a softwood, the first stage hydrolysate comprises at least about 20% 5-carbon sugar and at least about 70% 6-carbon sugar, and the second stage hydrolysate comprises at least about 90% 6-carbon sugar.

In some embodiments, lignin is recovered in the residue of the terminal stage, e.g., second stage, of hydrolysis of lignocellulosic feedstock. In one embodiment, the lignin-containing residue is dried to a liquid content of about 15% or less. In some embodiments, the lignin-containing residue is dried to a liquid content of about 35% to about 15%, e.g., any of about 35%, 30%, 25%, 20%, or 15%, or about 35% to about 30%, about 30% to about 25%, about 25% to about 20%, or about 20% to about 15%. In one embodiment, the lignin-containing residue is used as an energy source for said process. In one embodiment, the lignin-containing residue is used as a fuel source for electricity generation. In some embodiments, the lignin-containing residue is used as a chemical precursor for production of useful products, such as phenolic resins. In some embodiments, the lignin-containing residue is used as a feed to an anaerobic digestor for production of useful gaseous products, such as methane or syngas ($CO+CH_4$). In some embodiments, the lignin-containing residue is used as a soil enhancer.

In some embodiments, hydrolysis of a feedstock, e.g., lignocellulosic feedstock, is performed with an acid, e.g., nitric acid, in multiple stages including a first and a second stage, and the multiple, e.g., first and second, stage hydrolysates are combined prior to introduction into the bioreactor. In other embodiments, multiple, e.g., first and second, stage hydrolysates are introduced as separate hydrolyzed feedstock streams into separate bioreactors. For example, the first stage hydrolysate is introduced into a first bioreactor and the second stage hydrolysate is introduced into a second bioreactor, where the first and second bioreactors contain the same or different microorganism(s). In one embodiment, the first bioreactor comprises a first microorganism and the second bioreactor comprises a second microorganism, the first and second microorganisms are different, the first microorganism is optimized for growth and/or bioproduct production on the first stage hydrolysate, and the second microorganism is optimized for growth and/or bioproduct production on the second stage hydrolysate. In some embodiments, the process includes multiple first bioreactors in series and/or multiple second bioreactors in series.

In some embodiments, hydrolysis of a feedstock, e.g., lignocellulosic feedstock is performed with an acid, e.g., nitric acid, in multiple stages including a first stage and a second stage, the first stage hydrolysis occurs in a first hydrolysis module and the second stage hydrolysis occurs in a second hydrolysis module, the resulting second stage hydrolysate is re-introduced into the first hydrolysis module to produce a third hydrolysate, and the amount of soluble sugar molecules in the third hydrolysate is greater than the amount of soluble sugar molecules in the second stage hydrolysate.

In some embodiments, hydrolysis of a feedstock, e.g., lignocellulosic feedstock, is performed with an acid, e.g., nitric acid, in multiple stages including a first stage and a second stage, flash steam is generated in the first stage hydrolysis, and the flash steam is used to deconstruct the feedstock prior to hydrolysis. In some embodiments, flash steam is generated in the second stage hydrolysis, and the flash steam is used to deconstruct said feedstock prior to hydrolysis and/or to provide energy for the first stage hydrolysis. In some embodiments, flash steam is generated in the second stage hydrolysis, the flash steam is recompressed, and the recompressed steam is used to provide energy for the first stage hydrolysis and/or other applications such as, for example, a downstream distillation process for product purification, such as steam stripping distillation. In some embodiments, flash steam is generated in the second stage hydrolysis, the flash steam is used to provide energy for a third stage hydrolysis, the temperature of the third stage hydrolysis is lower than the temperature of the second stage hydrolysis, and the lower temperature permits hydrolysis of remaining oligomeric sugar molecules with less degradation than hydrolysis performed at a higher temperature.

In some embodiments, hydrolyzed feedstock is conditioned to remove inhibitors of microbial growth and/or bioproduct, e.g., biofuel, for example, butanol, production prior to introduction of the hydrolyzed feedstock into the bioreactor, with the conditioning process occurring continuously for the duration of the fermentation. In some embodiments, removal of inhibitors includes one or more process selected from overliming, adsorption, precipitation, and ion exchange. In one embodiment, removal of inhibitors is performed by contact of hydrolyzed feedstock with an ion exchange resin under conditions such that the inhibitors are retained on the resin. In one embodiment, the ion exchange resin is an anion exchange resin. In one embodiment, removal of inhibitors is performed by precipitation with a metal salt, such as an aluminum or iron salt, for example, aluminum sulfate or ferric chloride. In some embodiments, the inhibitors include organic acids, furans, phenols, soluble lignocellulosic materials, extractives, and/or ketones.

In some embodiments, fermentation of the immobilized microorganism is conducted under anaerobic conditions. In one embodiment, the microorganism is a *Clostridium* strain. In some embodiments, the *Clostridium* strain is derived from a species selected from *Clostridium saccharobutylicum*, *Clostridium saccharoperbutylacetonicum*, *Clostridium acetobutylicum*, and *Clostridium beijerinckii*. In some embodiments, the *Clostridium* strain is an environmental isolate or is derived from an environmental isolate. In some embodiments, the *Clostridium* strain possesses one or more phenotypic characteristics selected from butanol tolerance, tolerance to inhibitors of fermentation, low acid accumulation, stability in continuous fermentation, high butanol titer, production of biofuel with high butanol to acetone ratio, increased yield of butanol per unit of feedstock, increased yield of butanol per unit of cellular biomass, increased oxygen tolerance, increased ability to adhere to a solid support, and decreased ability to sporulate, relative to a wild-type or parent strain from which the *Clostridium* strain is derived, or *Clostridium saccharobutylicum* B643, *Clostridium saccharobutylicum* P262, *Clostridium sacchroperbutylacetonicum* N1-4, *Clostridium acetobutylicum* 824, or *Clostridium beijerinckii* 8524, grown under identical conditions.

In some embodiments, the support material on which the microorganism is immobilized is selected from bone char, polypropylene, steel, diatomaceous earth, zeolite, ceramic, engineered thermal plastic, clay brick, concrete, lava rock, wood chips, polyester fiber, glass beads, Teflon, polyetheretherketone, and polyethylene.

In some embodiments, the immobilized microorganism includes a biofilm.

In some embodiments, the bioreactor in which the immobilized microorganism is grown is in the form of a packed bed, an expanded bed, or a fluidized bed.

In some embodiments, the bioproduct produced in the process includes a biofuel, such as butanol, acetone, ethanol, or a combination thereof. In one embodiment, the biofuel includes butanol. In one embodiment, butanol is produced by a *Clostridium* strain.

In some embodiments, the process further includes recovery of the bioproduct, e.g., biofuel, from the fermentation medium. In some embodiments, the recovery process operates continuously for the duration of the fermentation. In some embodiments, the recovery process includes concentration of the bioproduct. In one embodiment, concentration of the bioproduct includes mechanical vapor recompression.

In some embodiments, the process further includes distillation to separate the bioproduct, e.g., a biofuel, such as butanol, from other components of the fermentation medium. In one embodiment, flash steam generated during hydrolysis of the feedstock provides energy for the distillation. In one embodiment, butyric acid is recovered in the distillation, the butyric acid is added to the fermentation medium in the bioreactor, and the microorganisms in the bioreactor convert the butyric acid to butanol. In one embodiment, the bioproduct is butanol, butyric acid is recovered in the distillation, the butyric acid is recycled back to the fermentation medium in the bioreactor, and the microorganisms in the bioreactor convert the butyric acid to butanol.

In some embodiments, hydrolysis of a feedstock, e.g., lignocellulosic feedstock, is performed with an acid, e.g., nitric acid, in multiple stages including a first stage and a second stage, the second stage hydrolysis is performed at a higher temperature than the first stage, flash steam is generated in the second stage hydrolysis, the flash steam is recompressed, and the recompressed steam is used to provide energy for the distillation. In some embodiments, flash steam is generated in the second stage hydrolysis, optionally recompressed, and used to provide energy for preheating a feed stream to the distillation. In some embodiments, flash steam is generated in the second stage hydrolysis, recompressed, and used to provide energy for drying and/or dehydration of the products separated in the distillation.

In another aspect, a system for production of a bioproduct is provided. The system includes a feedstock hydrolysis unit and a bioreactor. A carbon-containing feedstock is hydrolyzed in the hydrolysis unit. The hydrolyzed feedstock is continuously fed to a microbial growth medium in the bioreactor, which contains a fermenting microorganism immobilized on a support. In some embodiments, the feedstock hydrolysis unit and the bioreactor are in fluid communication, the hydrolysis unit is upstream from the bioreactor, and the feedstock is continuously hydrolyzed and continuously fed to the bioreactor for the duration of the fermentation. Hydrolysis of the feedstock produces carbohydrate molecules that serve as a carbon source for the fermentation, and the microorganism continuously converts the hydrolyzed feedstock into a bioproduct. In one embodiment, the bioproduct is a biofuel (e.g., butanol, acetone, ethanol). In other embodiments, the bioproduct is a biochemical or a biochemical feedstock, i.e., a biochemical that may be derivatized or converted to another product, e.g., via chemical synthesis. In some embodiments, the bioproduct is a solvent, a biomolecule, an organic acid, an alcohol, a vitamin, a fatty acid, an aldehyde, a lipid, a long chain organic molecule, or a sugar alcohol.

In some embodiments, the system contains multiple bioreactors arranged in parallel, the multiple bioreactors are in fluid communication with the hydrolysis unit, the hydrolyzed feedstock is fed continuously into the bioreactors, the fermentation of the microorganism occurs continuously in the bioreactors, and the multiple bioreactors contain the same or different microorganism(s).

In some embodiments, the system contains multiple bioreactors arranged in series, the first bioreactor in the series is in fluid communication with the hydrolysis unit and with a downstream bioreactor, each subsequent bioreactor in the series downstream from the first bioreactor is in fluid communication with the previous upstream bioreactor in the series, the hydrolyzed feedstock is fed continuously into the first bioreactor in the series, and effluent from each bioreactor is fed to the next bioreactor downstream in the series. In some embodiments, evolved gas may be removed between series nodes during operation of the bioreactors.

In one embodiment, bioreactors are arranged in parallel trains in a hybrid series/parallel arrangement. For example, fermentation may proceed in multiple bioreactors that are arranged in a combination to optimize productivity, such as a primary reactor arranged in series with a train of parallel reactors with hydrolyzed feedstock fed continuously into the first bioreactor in the series and effluent from each bioreactor fed to the next bioreactor downstream in the series.

In one embodiment, continuous hydrolysis and fermentation, and optionally conditioning and/or product recovery, operate continuously in the system for at least about 300 hours. In another embodiment, continuous hydrolysis and fermentation operate continuously in the system for at least about 1000 hours.

In some embodiments, the feedstock is a cellulosic material, for example, a lignocellulosic material. In some embodiments, the feedstock is wood selected from softwood, hardwood, or a combination thereof. In some embodiments, the feedstock is a lignocellulosic material in the form of wood chips, sawdust, saw mill residue, or a combination thereof. In some embodiments, the lignocellulosic material (e.g., wood chips sawdust, saw mill residue, or a combination thereof) is from a feedstock source that has been subjected to some form of disease in the growth and/or harvest production period. In one embodiment, the feedstock source is mountain pine beetle infested pine. In another embodiment, the feedstock source is sudden oak death syndrome infested oak, e.g., coastal live oak, tanoak, etc. In another embodiment, the feedstock source is Dutch elm disease infested elm. In other embodiments, the feedstock source is lignocellulosic material that has been damaged by drought or fire.

In some embodiments, lignocellulosic feedstock material is deconstructed prior to hydrolysis. Deconstruction may include one or more process selected from presteaming, mechanical grinding, and mechanical explosion. In some embodiments, the feedstock material is deconstructed prior to harvest by a natural or non-natural environmental condition, for example, drought, infestation, fire, and/or herbicide exposure. In some embodiments, the feedstock material may be deconstructed by a disease organism, for example, mountain pine beetle deconstruction of pine.

In some embodiments, lignocellulosic feedstock material is pretreated to remove extractives. The extractive removal pretreatment may include compression, water extraction, solvent extraction, alkaline extraction, enzymatic treatment, fungal treatment, oxygen treatment, or air drying. In some embodiments, the pretreatment to remove extractives may occur prior to or in conjunction with deconstruction.

In some embodiments, hydrolysis of a feedstock, such as a lignocellulosic feedstock, is performed by treatment with an acid. In some embodiments, the acid includes nitric acid, formic acid, acetic acid, phosphoric acid, hydrochloric acid, or sulfuric acid, or a combination thereof. In one embodiment, the hydrolysis is performed with nitric acid. In another embodiment, the hydrolysis is performed with a combination of nitric acid and acetic acid. In one embodiment, the hydrolysis is performed with nitric acid, and the hydrolysis reactor contains stainless steel. In some embodiments, the hydrolysis reactor contains hastelloy or zirconium. In some embodiments, hydrolysis is performed in multiple stages in the same or different hydrolysis reactor module(s).

In some embodiments, the hydrolysis unit contains a first hydrolysis module and a second hydrolysis module, acid, e.g., nitric acid, hydrolysis of a feedstock, e.g., lignocellulosic feedstock, is performed in multiple stages, including a first stage in the first hydrolysis module and a second stage in the second hydrolysis module, and the temperature of the nitric acid in the first hydrolysis module is higher than the temperature of the nitric acid in the second hydrolysis module.

In some embodiments, the hydrolysis product stream from the second hydrolysis module is re-introduced into the first hydrolysis module to produce a third hydrolysate, and the amount of soluble sugar molecules produced in the third hydrolysate is greater than the amount of soluble sugar molecules in the second stage hydrolysate.

In some embodiments, the hydrolysis product streams from multiple, e.g., first and second, hydrolysis modules are combined prior to introduction into the bioreactor.

In other embodiments, the hydrolysis product streams from multiple, e.g., first and second, hydrolysis modules are introduced as separate hydrolyzed feedstock streams into separate bioreactors. For example, the first stage hydrolysate is introduced into a first bioreactor and the second stage hydrolysate is introduced into a second bioreactor, and the first and second bioreactors contain the same or different microorganism(s). In one embodiment, the first bioreactor contains a first microorganism and the second bioreactor contains a second microorganism, the first and second microorganisms are different, and the first microorganism is optimized for growth on the first stage hydrolysate and the second microorganism is optimized for growth on the second stage hydrolysate.

In some embodiments, the system contains multiple first bioreactors in series and/or multiple second bioreactors in series.

In some embodiments, hydrolysis of a feedstock, e.g., lignocellulosic feedstock, is performed with an acid, e.g., nitric acid, in multiple stages including a first stage and a second stage, flash steam is generated in the first stage hydrolysis, and the flash steam provided to the feedstock for deconstruction of the feedstock prior to hydrolysis. In some embodiments, flash steam is generated in the second stage hydrolysis, and the flash steam is provided to the feedstock for deconstruction of the feedstock prior to hydrolysis and/or to the first hydrolysis module to provide energy for the first stage hydrolysis. In some embodiments, flash steam is generated in the second stage hydrolysis, the flash steam is recompressed, and the recompressed steam is provided to the first hydrolysis module to provide energy for the first stage hydrolysis and/or other applications such as, for example, steam stripping distillation. In some embodiments, flash steam is generated in the second stage hydrolysis, the flash steam is provided to a third hydrolysis module to provide energy for a third stage hydrolysis, the temperature in the third hydrolysis module is lower than the temperature in the second hydrolysis module, and the lower temperature permits hydrolysis of remaining oligomeric sugar molecules with less degradation than hydrolysis performed at a higher temperature.

In some embodiments, the system further includes a conditioning unit that is in fluid communication with both the hydrolysis unit and the bioreactor, downstream from the hydrolysis unit and upstream from the bioreactor. In some embodiments, hydrolysis and conditioning processes occur continuously for the duration of the fermentation. In one embodiment, hydrolyzed feedstock is conditioned in the conditioning unit to remove inhibitors of microbial growth and/or production of bioproduct, e.g., biofuel, such as butanol, prior to introduction of the hydrolyzed feedstock into the bioreactor, and the conditioning process occurs continuously for the duration of the fermentation. In some embodiments, removal of inhibitors includes one or more process(as) selected from overliming, adsorption, precipitation, and ion exchange. In one embodiment, the conditioning unit includes an ion exchange resin, and removal of inhibitors is performed by contact of hydrolyzed feedstock with the ion exchange resin under conditions in which the inhibitors are retained on the resin. In one embodiment, the ion exchange resin is an anion exchange resin. In one embodiment, removal of inhibitors is performed by precipitation with a metal salt, such as an aluminum or iron salt, for example, aluminum sulfate or ferric chloride. In some embodiments, the inhibitors include organic acids, furans, phenols, soluble lignocellulosic materials, extractives, and/or ketones.

In some embodiments, fermentation is conducted under anaerobic conditions. In one embodiment, the microorganism is a *Clostridium* strain.

In some embodiments, the support material on which the microorganism is immobilized is selected from bone char, polypropylene, steel, diatomaceous earth, zeolite, ceramic, engineered thermal plastic, clay brick, concrete, lava rock, wood chips, polyester fiber, glass beads, Teflon, polyetheretherketone, and polyethylene.

In some embodiments, the immobilized microorganism includes a biofilm.

In some embodiments, the bioreactor in which the immobilized microorganism is grown is in the form of a packed bed, an expanded bed, or a fluidized bed.

In some embodiments, the bioproduct is a biofuel which includes butanol, acetone, ethanol, or a combination thereof. In one embodiment, the biofuel includes butanol.

In some embodiments, the system further includes a recovery unit for recovery of the bioproduct from the fermentation medium. In some embodiments, the recovery unit is in fluid communication with and downstream from the bioreactor, and the recovery process operates continuously for the duration of the fermentation.

In some embodiments, the recovery unit includes a concentration module for concentration of the bioproduct. In one embodiment, concentration of the bioproduct includes mechanical vapor recompression.

In some embodiments, the recovery unit includes a distillation module to separate the bioproduct from other components of the fermentation medium, in fluid communication with and downstream from the concentration module. In some embodiments, flash steam generated during hydrolysis of the feedstock provides energy for the distillation. In one embodiment, the bioproduct is butanol, and the system contains a recovery unit for recovery of butanol from the fermentation medium. Recovery of butanol may include distillation to separate butanol from other components of the fermentation medium. In one embodiment, butyric acid is recovered in the distillation, butyric acid is recycled back to the bioreactor and is added to the fermentation medium in the bioreactor, and the microorganism in the bioreactor converts butyric acid to butanol.

In one embodiment, the distillation module includes a first distillation column in fluid communication with and downstream from the concentration module, the distillate exiting the top of the first distillation column contains acetone and ethanol, and the distillate from the bottom of the first distillation column contains butanol, the distillation module further includes a decanter in fluid communication with and downstream from the first distillation column, the decanter comprises a top phase and a bottom phase, and butanol and water from the top phase in the decanter are fed into a second distillation column in fluid communication with and downstream from the decanter, and the distillate from the bottom of the second distillation column contains butanol. In one embodiment, the distillation module further contains a third distillation column in fluid communication with and downstream from the first distillation column, distillate exiting the top of the third distillation column contains acetone and distillate exiting the bottom of the column comprises ethanol, and the temperature of the third distillation column is lower than the temperature of the first distillation column. In one embodiment, the distillate from the bottom of the second distillation column contains both butanol and butyric acid, and the distillation module further includes a distillation column for separation of butanol and butyric acid in fluid communication with and downstream from the second distillation column, distillate exiting the top of the column for separation of butanol and butyric acid contains butanol and distillate exiting the bottom of the column contains butyric acid, butyric acid is recovered in the distillation, the butyric acid is provided to the fermentation medium in the bioreactor, and the microorganism converts said butyric acid to butanol.

In some embodiments, lignin is recovered in the residue of the terminal stage, e.g., second stage, of hydrolysis of lignocellulosic feedstock. In one embodiment, the lignin-containing residue is dried to a liquid content of about 35% to about 15%, e.g., any of about 35%, 30%, 25%, 20%, or 15%, or about 35% to about 30%, about 30% to about 25%, about 25% to about 20%, or about 20% to about 15% or less. In one embodiment, the lignin-containing residue is used as an energy source for said process. In one embodiment, the lignin-containing residue is used as a fuel source for electricity generation. In some embodiments, the lignin-containing residue is used as a chemical precursor for production of useful products, such as phenolic resins. In some embodiments, the lignin-containing residue is used as a feed to an anaerobic digestor for production of useful gaseous products, such as methane or syngas. In some embodiments, the lignin-containing residue is used as a soil enhancer.

In some embodiments, hydrolysis of a feedstock, e.g., lignocellulosic feedstock, is performed with an acid, e.g., nitric acid, in multiple stages including a first stage and a second stage, the hydrolysis unit includes a first hydrolysis module and a second hydrolysis module, nitric acid hydrolysis comprises a first stage in the first hydrolysis module and a second stage in the second hydrolysis module, the temperature of the nitric acid in the first hydrolysis module is higher than the temperature of the nitric acid in the second hydrolysis module, flash steam is generated in the second stage hydrolysis, the flash steam is recompressed, and the recompressed steam is used to provide energy for said distillation. In some embodiments, flash steam is generated in the second stage hydrolysis, optionally recompressed, and used to provide energy for preheating a feed stream to said distillation. In some embodiments, flash steam is generated in the second stage hydrolysis, the flash steam is recompressed, and the recompressed steam is used to provide energy for drying and/or dehydration of the products separated in the distillation.

In some embodiments, an extractives stream removed before or during feedstock hydrolysis and/or flash steam generated during feedstock hydrolysis is in fluid communication with the product recovery system in order to recover additional products of value, such as terpenes, sterols, sterol esters, resin acids, fatty acids, wax esters, diglycerides, triglycerides, and/or methanol. In some embodiments, flash steam generated during feedstock hydrolysis is in fluid communication with the product recovery system for use as a distillation aid, for preheating the feed mixture and/or for use in steam stripping distillation.

In some embodiments, material recovered from a primary product recovery column, from which a bioproduct, e.g., a solvent, has been removed, is reintroduced into the bioproduct production system. For example, the material may used as primary dilution water or rinse water (for example, to rinse sugars from biomass), or other water addition stream. In so doing, fermentation nutrients may be reintroduced to the process, reducing cost and/or increasing performance, sugars may be reintroduced to the process, improving process yield, and/or water may be reused.

In some embodiments of the bioproduct production processes and systems herein, the bioreactor(s) operated under pressure to compress gas in the bioreactor(s), for example, $CO_2$ generated by the microorganisms during fermentation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
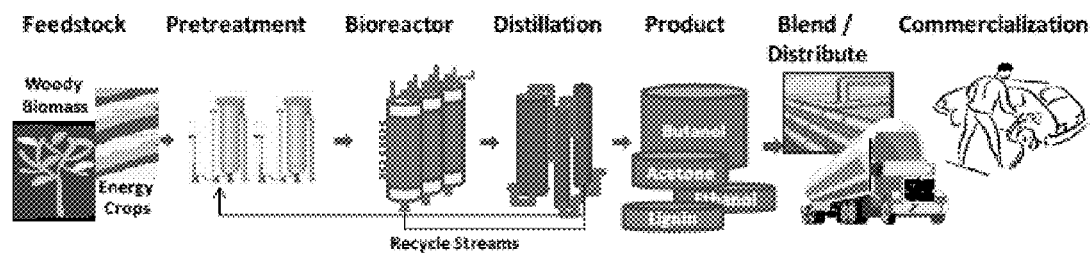
FIG. 1 shows a schematic diagram of an embodiment of an integrated biofuel plant in which biobutanol production processes and systems described herein may be utilized.

The invention provides processes and systems for continuous bioproduct, e.g., biofuel, production via microbial fermentation. In the processes and systems described herein, microbial fermentation is utilized to convert sugars extracted from a carbohydrate-containing feedstock to produce a bioproduct, such as a biofuel, for example, biobutanol and optionally other co-products.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

Numeric ranges provided herein are inclusive of the numbers defining the range.

Definitions

"A," "an" and "the" include plural references unless the context clearly dictates otherwise.

"Bioproduct" refers to any substance of interest produced biologically, i.e., via a metabolic pathway, by a microorganism, e.g., in a microbial fermentation process. Bioproducts include, but are not limited to biofuels (e.g., butanol, acetone, ethanol), solvents, biomolecules (e.g., proteins (e.g., enzymes), polysaccharides), organic acids (e.g., formate, acetate, butyrate, propionate, succinate, lactate, adipic acid, amino acids), alcohols (e.g., methanol, propanol, isopropanol, pentanol, hexanol, 2-butanol, isobutanol, glycerol), fatty acids, aldehydes (e.g., acetaldehyde, butyraldehyde), ketones (e.g., butanone), lipids, long chain organic molecules (for example, for use in surfactant production), vitamins, and sugar alcohols (e.g., xylitol).

"Biofuel" refers to fuel molecules (e.g., butanol, acetone, and/or ethanol) produced biologically by a microorganism, e.g., in a microbial fermentation process.

"Biobutanol" refers to butanol (i.e., n-butanol) produced biologically by a microorganism, e.g., in a microbial fermentation process.

"Byproduct" refers to a substance that is produced and/or purified and/or isolated during any of the processes described herein, which may have economic or environmental value, but that is not the primary process objective. Nonlimiting examples of byproducts of the processes described herein include lignin compounds and derivatives, carbohydrates and carbohydrate degradation products (e.g., furfural, hydroxymethyl furfural, formic acid), and extractives (described infra).

"Feedstock" refers to a substance that can serve as a source of sugar molecules to support microbial growth in a fermentation process. In some embodiments, the feedstock must be pretreated to release the sugar molecules. In one embodiment, the feedstock, which contains carbohydrate polymers, is hydrolyzed to release 5 and/or 6 carbon containing carbohydrate molecules in monomeric and/or soluble oligomeric forms.

"Deconstruction" refers to mechanical, chemical, and/or biological degradation of biomass into to render individual components (e.g., cellulose, hemicellulose) more accessible to further pretreatment processes, for example, a process to release monomeric and oligomeric sugar molecules, such as acid hydrolysis.

"Conditioning" refers to removal of inhibitors of microbial growth and/or bioproduct, e.g., biofuel, production from a feedstock or pretreated feedstock (e.g., a hydrolysate produced by hydrolysis of a feedstock) and/or adjustments to physical properties of the feedstock or pretreated feedstock to improve conditions that support microbial growth and product production.

"Titer" refers to amount of a substance produced by a microorganism per unit volume in a microbial fermentation process. For example, biobutanol titer may be expressed as grams of butanol produced per liter of solution.

"Yield" refers to amount of a product produced from a feed material (for example, sugar) relative to the total amount that of the substance that would be produced if all of the feed substance were converted to product. For example, biobutanol yield may be expressed as % of biobutanol produced relative to a theoretical yield if 100% of the feed substance (for example, sugar) were converted to biobutanol.

"Productivity" refers to the amount of a substance produced by a microorganism per unit volume per unit time in a microbial fermentation process. For example, biobutanol productivity may be expressed as grams of butanol produced per liter of solution per hour.

"Wild-type" refers to a microorganism as it occurs in nature.

"Biomass" refers to cellulose- and/or starch-containing raw materials, including but not limited to wood chips, corn stover, rice, grasses, forages, perrie-grass, potatoes, tubers, roots, whole ground corn, grape pomace, cobs, grains, wheat, barley, rye, milo, brans, cereals, sugar-containing raw materials (e.g., molasses, fruit materials, sugar cane, or sugar beets), wood, and plant residues.

"Starch" refers to any starch-containing materials. In particular, the term refers to various plant-based materials, including but not limited to wheat, barley, potato, sweet potato, tapioca, corn, maize, cassava, milo, rye, and brans. In general, the term refers to any material comprised of the complex polysaccharide carbohydrates of plants, comprised of amylose, and amylopectin, with the formula $(C_6H_{10}O5)_x$, wherein "x" can be any number.

"ABE fermentation" refers to production of acetone, butanol, and/or ethanol by a fermenting microorganism.

"Advanced biofuels" are high-energy liquid transportation fuels derived from low nutrient input/high per acre yield crops, agricultural or forestry waste, or other sustainable biomass feedstocks including algae.

"Lignocellulosic" biomass refers to plant biomass that contains cellulose, hemicelluloses, and lignin. The carbohydrate polymers (cellulose and hemicelluloses) are tightly bound to lignin.

"Lignins" are macromolecular components of wood that contain phenolic propylbenzene skeletal units linked at various sites.

n-Butanol (1-butanol) is also referred to as "butanol" herein.

"ATCC" refers to the American Type Culture Collection, P.O. Box 1549, Manassas, Va. 20108.

Feedstock

A feedstock is a substance that provides the base material from which sugar molecules are generated for inclusion in a microbial growth medium, to support the growth of the microorganism. In some embodiments, the feedstock is cellulosic biomass. In some embodiments, the feedstock contains cellulose and hemicellulose, for example, lignocellulosic biomass or wood pulp. In some embodiments, the feedstock is a polysaccharide from which soluble sugar molecules may be produced that can support growth of a microorganism, for example, a polysaccharide waste product such as crab, shrimp, or lobster shells, chitin, chitosan, pectin, or sucrose.

In some embodiments, the feedstock is woody biomass. In one embodiment, the feedstock is softwood, for example, pine, e.g., Lodgepole or Loblolly pine. In one embodiment, the feedstock contains mountain pine beetle infested pine, for example, dying ("red stage") or dead ("grey" stage). In another embodiment, the feedstock is hardwood, for example, maple, birch, or ash. In another embodiment, the feedstock is mixed hardwood and softwood. In another embodiment, the feedstock is mixed hardwood. In some embodiments, the woody biomass is in the form of wood chips, sawdust, saw mill residue, wood fines, or a combination thereof.

In some embodiments, the feedstock is obtained as a process stream from a biomass processing facility, for example, a pulp mill. In various embodiments of pulp mill process streams, the process stream may include reject pulp, wood knots or shives, pulp screening room rejects (e.g., essentially cellulose in water), prehydrolysis extraction stream, and/or black liquor. In other embodiments, the feedstock may include bagasse, corn cobs, beet molasses, pulp and/or paper, sweet sorghum syrup, or barley hulls.

Lignocellulose contains a mixture of carbohydrate polymers and non-carbohydrate compounds. The carbohydrate polymers contain cellulose and hemicellulose, and the non-carbohydrate portion contains lignin. The non-carbohydrate portion may also contain ash, extractives, and/or other components. The specific amounts of cellulose, hemicelluloses, and lignin depends on the source of the biomass. For example, municipal solid waste may contain primarily cellulose, and extract streams from a paper and pulp plant may contain primarily hemicelluloses. The remaining composition of lignocellulose may also contain other compounds such as proteins.

Cellulose, which is a β-glucan built up of D-glucose units linked by β(1,4)-glycosidic bonds, is the main structural component of plant cell walls and typically constitutes about 35-60% by weight (% w/w) of lignocellulosic materials.

Hemicellulose refers to non-cellulosic polysaccharides associated with cellulose in plant tissues. Hemicellulose frequently constitutes about 20-35% w/w of lignocellulosic materials, and the majority of hemicelluloses consist of polymers based on pentose (five-carbon) sugar units, such as D-xylose and D-arabinose units, hexose (six-carbon) sugar units, such as D-glucose and D-mannose units, and uronic acids such as D-glucuronic acid.

Lignin, which is a complex, cross-linked polymer based on variously substituted p-hydroxyphenylpropane units, typically constitutes about 10-30% w/w of lignocellulosic materials.

Any material containing cellulose and/or hemicellulose or cellulose and/or hemicellulose oligomeric and/or monomeric compounds (e.g., sugar monomers, dimers (e.g., cellobiose), trimers (e.g., cellotriose)) may be used as the feedstock. The material may contain cellulose and/or hemicellulose without lignin.

Lignocellulosic biomass may be derived from a fibrous biological material such as wood or fibrous plants. Examples of suitable types of wood include, but are not limited to, spruce, pine, hemlock, fir, birch, aspen, maple, poplar, alder, *salix*, cottonwood, rubber tree, marantii, *eucalyptus*, sugi, and acase. Examples of suitable fibrous plants include, but are not limited to, corn stover and fiber, flax, hemp, *cannabis*, sisal hemp, bagasse, straw, cereal straws, reed, bamboo, *mischantus*, kenaf, canary reed, *Phalaris arundinacea*, and grasses. Other lignocellulosic materials may be used such as herbaceous material, agricultural crop or plant residue, forestry residue, municipal solid waste, pulp or paper mill residue, waste paper, recycling paper, or construction debris. Examples of suitable plant residues include, but are not limited to, stems, leaves, hulls, husks, cobs, branches, bagasse, wood chips, wood pulp, wood pulp, and sawdust. Examples of suitable waste paper include, but are not limited to, discarded paper of any type (e.g., photocopy paper, computer printer paper, notebook paper, notepad paper, typewriter paper), newspaper, magazines, cardboard, and paper-based packaging material. Materials with high mineral content may potentially require additional pH adjustment (e.g., additional amounts of chemicals for pH adjustment) for effective processing.

In embodiments in which wood is used as the feedstock, the bioproduct, e.g., biofuel, production plant can include a facility to unload, wash and screen incoming wood chips to remove any dirt and debris. The chips can be ground to the optimum size for hydrolysis and conveyed to the feed hopper for introduction into the hydrolysis unit. Data can be collected from a feedstock provider and used to size and specify the wood handling equipment for a given plant.

Other feedstocks that may be used in the bioproduct (e.g., biofuel, for example, biobutanol) production processes described herein include hemicellulose extract from wood, beet extract, beet molasses, sorghum syrup, barley hulls, potato processing waste, and brewers mash.

In some embodiments, a feedstock mix containing about 40% logging residues, about 20% sustainable roundwood, about 20% woody energy crops, and about 20% herbaceous energy crops may be used. This blend can account for regional variation and provide significant flexibility in selecting locations for facilities and in procuring feedstock supply contracts.

Feedstock flexibility may permit utilization of combinations of feedstocks in geographic locations where the available supply of feedstocks taken individually are not sufficient to justify a commercial scale bioproduct, e.g., biobutanol, production plant, or where synergistic value can be realized from combining feedstocks that allow for better practices to be implemented with regard to the underlying land (e.g, improved crop rotations) or in terms of more economic harvest, handling and storage logistics. Feedstock flexibility may also provide opportunities to locate plants in niche sites where end use markets are in close proximity to otherwise non-utilizable feedstocks.

In some embodiments, diverse feedstocks may be utilized by versatile strains which are capable of converting both 5-carbon and 6-carbon sugar molecules (including multimeric forms) to a bioproduct, e.g., biofuel, for example, n-butanol. In some embodiments, a feedstock may be hydrolyzed to provide hydrolysates that are rich in 5-carbon or 6-carbon sugars, and microbial strains which have been optimized for growth and bioproduct, e.g., biofuel, production on 5-carbon or 6-carbon sugars are used for bioproduct production, either in separate or combined fermentations. In some embodiments, a microbial strain that has been optimized for growth on a particular feedstock or hydrolysate generated from a particular feedstock, is used for bioproduct, e.g., biofuel, production.

Pretreatment of Feedstock

Feedstocks such as those described herein can be pretreated using a variety of methods and systems prior to bioconversion. Preparation of the feedstock can include chemical or physical modification of the feedstock. For example, the feedstock can be shredded, sliced, chipped, chopped, heated, burned, dried, separated, extracted, hydrolyzed, and/or degraded. These modifications can be performed by biological, non-biological, chemical, or non-chemical processes.

In some embodiments in which a cellulosic, e.g., lignocellulosic, feedstock is used, processes may be used to break down cellulose and/or hemicellulose into sugar molecules that may be more easily processed by a microorganism. Processes that may be used include acid hydrolysis, enzymatic hydrolysis, gasification, pyrolysis, and cellulose degradation by a microorganism.

Deconstruction

In some embodiments, the feedstock, such as lignocellulosic feedstock, for example, wood chips, sawdust, and/or sawdust residue, is deconstructed prior to a downstream pretreatment process such as hydrolysis. Deconstruction may include, but is not limited to, presteaming to swell and loosen material, mechanical grinding, mechanical explosion (e.g., steam or other chemical treatment followed by rapid decompression), vacuum treatment, acid-feedstock contact (diffusion of acid into feedstock), or a combination thereof. In some embodiments, deconstruction renders cellulose and/or hemicellulose in the feedstock more accessible for hydrolysis.

Removal of Extractives

In some embodiments, the feedstock, such as lignocellulosic feedstock, for example, wood chips, sawdust, and/or sawdust residue, is pretreated to remove extractives. Extractives are material that is extracted from the feedstock by a process such as compression, water or solvent extraction, or air drying. Non-limiting examples of extractives include terpenes, resin acids, fatty acids, sterols, phenolic compounds, and triglycerides. Extractives may include, but are not limited to, p-coumaric acid, ferulic acid, 4-hydroxybenzoic acid, vanillic acid, syringaldehyde, vanillin, furfural, hydroxymethylfurfural, and glucuronic acid. Extractives may be removed for other uses, such as production of sterols, or burned to provide energy for a bioproduct, e.g., biofuel, production process as described herein.

In some embodiments, extractives are removed prior to or in conjunction with deconstruction of the feedstock.

Hydrolysis

Typically, a feedstock contains sugar molecules in an oligomeric form, e.g., a polymeric form, and must be hydrolyzed to extract and release soluble monomeric and/or multimeric sugar molecules, which are converted to bioproduct, e.g., biofuel, in a microbial fermentation as described herein. In some embodiments, the sugar molecules are present in the feedstock in cellulose and/or hemicellulose. In one embodiment, the feedstock is lignocellulosic biomass and the sugar molecules are present in the feedstock in cellulose and hemicellulose.

Figure 4:
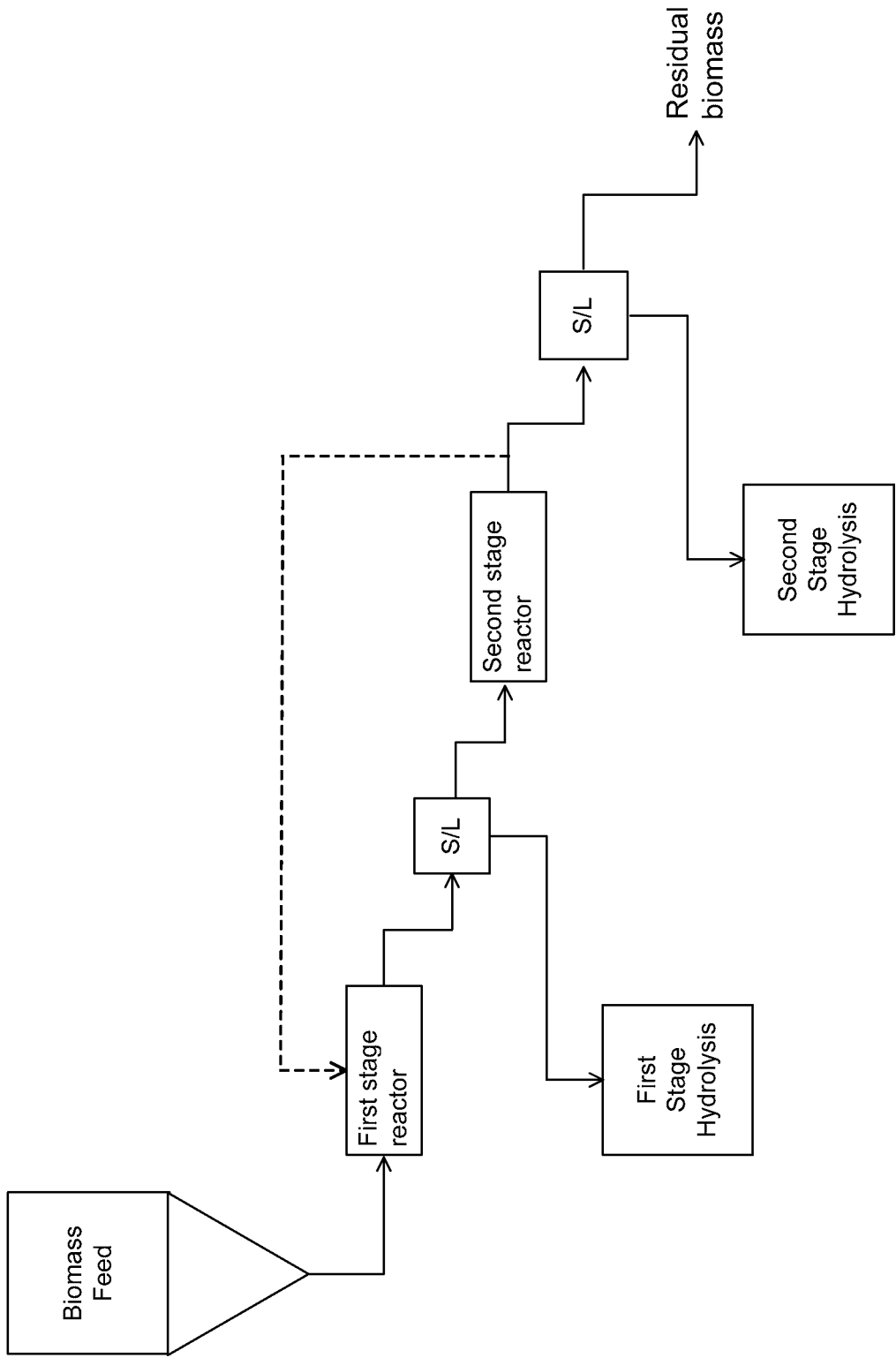
FIG. 4 shows a schematic diagram of an embodiment of a two-stage feedstock hydrolysis process.

In some embodiments, the feedstock is pretreated with an acid hydrolysis process. Acids that may be used for hydrolysis include, but are not limited to, nitric acid, formic acid, acetic acid, phosphoric acid, hydrochloric acid, and sulfuric acid, or a combination thereof. In one embodiment, acid hydrolysis is performed in a single stage. In some embodiments, acid hydrolysis is performed in two or more stages, under different conditions in each stage to hydrolyze different components of the feedstock in each stage. Acid hydrolysis performed in multiple stages may serve to limit the impact of kinetically controlled carbohydrate degradation mechanisms. A schematic diagram of an embodiment of a two-stage acid hydrolysis process is depicted in FIG. 4.

An acid hydrolysis system may be designed to submerge and flood the feedstock with the acid solution in the hydrolysis reactor, e.g., in a vertical section of the hydrolysis reactor, to insure even acid impregnation. Even heat distribution may be obtained by using both direct steam injection and a jacketed vessel in conjunction with a mechanical screw auger. Variable speed drives may be used with temperature sensing instrumentation to control reactor residence time and temperature allowing reactor severity to be adjusted on-line. Alternative reactor configurations with functionally similar properties may also be utilized. For example, a horizontal digestor configuration may be used. In this type of reactor, the material is only partially submerged. Similarly, in some embodiments, in order to reach higher soluble sugar concentrations, the feedstock material is not completely submerged in the acid containing solution, thereby producing a hydrolysate that contains an increased sugar concentration (i.e., less dilution water added at the outset). In some embodiments, a multiple-stage dilute nitric acid hydrolysis process is used. In one embodiment, a two-stage dilute nitric acid process is used. In one embodiment, conditions in the first stage are chosen to achieve hydrolysis of about 70% to about 90% of the hemicellulose in the feedstock and conditions in the second stage are chosen to achieve hydrolysis of about 40% to about 70% of the cellulose in the feedstock. The first stage mainly targets the hydrolysis of the hemicellulose, yielding a mannose and/or xylose rich hydrolysate, whereas the second stage uses the solids remaining from the first stage and targets the cellulose, yielding a glucose rich hydrolysate. Typically, first stage hydrolysate liquors contain a mix of 5-carbon and 6-carbon sugars, e.g., extracted primarily from hemicellulose and non-recalcitrant cellulose biomass components, and second stage hydrolysate contains primarily 6-carbon sugars, e.g., extracted from cellulose fibers, in both cases as soluble monomeric and/or multimeric forms. 6-carbon monosaccharides may include, but are not limited to, glucose, mannose, and galactose. 6-carbon disaccharides may include, but are not limited to, cellobiose, mannobiose, glucomannose, and galactomannose. Other multimeric forms may include, but are not limited to, cellotriose, cellotetrose, and cellopentose. 5-carbon monosaccharides may include, but are not limited to xylose and arabinose. 5-carbon disaccharides and other multimeric forms may include, but are not limited to, xylobiose, xylotriose, and arabinoxylose.

In some embodiments in which hardwood is used as the feedstock, the first stage hydrolysate contains about 60% to about 75% 5-carbon sugar by weight and about 25% to about 40% 6-carbon sugar by weight, and the second stage hydrolysate contains about 80% to about 95% 6-carbon sugar by weight. In some embodiments in which softwood is used as the feedstock, the first stage hydrolysate contains about 20% to about 30% 5-carbon sugar by weight and about 70% to about 80% 6-carbon sugar by weight, and the second stage hydrolysate contains about 90% to about 100% 6-carbon sugar by weight, wherein the second stage is performed at a higher temperature than the first stage.

A first stage hydrolysis module may be coupled to a second stage hydrolysis module, with solid residue separated from liquid hydrolysate generated in the first stage hydrolysis serving as substrate for the second hydrolysis process. The residual solids may be rinsed/washed in order to increase the separation and recovery yield of soluble sugars separated from the biomass.

In some embodiments, the second stage hydrolysis is performed at a higher temperature than the first stage hydrolysis.

In some embodiments, hydrolysis is performed at a nitric acid concentration of about 0.05 to about 0.1%, about 0.1% to about 0.5%, about 0.5% to about 1%, about 1% to about 4%, about 1.3% to about 3.5%, or about 1.3% (w/w of dry feedstock) for both hydrolysis stages, at a temperature of about 170° to about 175° C. in the first stage and a temperature of about 210° to about 230° C. in the second stage, and at the saturation pressure for steam at the reactor temperature for each hydrolysis stage.

In some embodiments, the liquid (acid) to solid (feedstock) ratio for hydrolysis is about 10:1 to about 5:1 or about 7.5:1 to about 5:1. In a circulating reactor, the ratio of liquid to solid may be about 5:1 to about 3:1 or about 3.5:1 to about 3:1. In a continuous extrusion reactor, the ratio of liquid to solid may be about 4:1 to about 0.5:1.

In some embodiments, the soluble sugar extraction yield from the feedstock in the first stage hydrolysis as about or at least about 6, 10, 15, 20, 30, 34, 40, 50, or 60% from cellulose and about or at least about 1, 3, 6, 10, 20, 40, 60, 70, 75, 80, 85, 90, 95, or 99% from hemicellulose. In some embodiments, the soluble sugar extraction yield from solid residue remaining after the first stage hydrolysate in the second stage hydrolysis is about or at least about 25, 35, 45, 55, 65, 75, 85, or 95% from cellulose and about or at least about 1, 3, 6, or 10% from hemicellulose. In some embodiments, conditions are chosen such that short residence times may be utilized, providing high productivity (smaller reactors) and minimal sugar degradation products. Minimizing degradation products makes the pretreatment step more compatible with the downstream fermentation process. For example, in some embodiments, residence time in the hydrolysis reactor for first stage nitric acid hydrolysis with ¼ inch wood chips may be about 5 to about 8 minutes, with longer residence time of about 3 to about 15, or up to about 30 minutes for larger feed material, and residence time for ¼ inch wood chips for second stage nitric acid hydrolysis may be about 3 to about 6 minutes, or about 3 to about 20 minutes, with longer residence time for larger feed material. The residence times may be affected by the degree of material deconstruction and/or the applied acid conditions.

Dilute nitric acid pretreatment has several advantages over other types of acid pretreatment. The passivation characteristics of nitric acid at lignocellulosic pretreatment conditions permit the use of stainless steel, rather than the more exotic and expensive materials required for other pretreatment processes, such as dilute sulfuric acid treatment. This confers a substantial capital cost advantage. Further, the hydrolysis and neutralization process is rich in nitrogen that can be utilized in fermentation. In some embodiments, hydrolysate streams are neutralized with ammonia to produce ammonium nitrate Ammonium nitrate is a nutrient for microorganisms in the downstream fermentation process.

Parameters for nitric acid hydrolysis of feedstock are also described in U.S. Pat. Nos. 4,384,897, 4,706,903, 5,221,357, 5,366,558, 5,536,325, 5,628,830, and 6,019,900.

In a multiple-stage hydrolysis process as described herein, hydrolysis reactors for each stage may be the same or different. For example, a second stage reactor may have a higher or lower capacity than a first stage reactor. In some embodiments, a hydrolysis reactor may have an internal volume of about or at least about 1, 2, 5, 10, 20, 50, 100, 200, 500, 1000, 2500, 5000, 10,000, 50,000, 100,000, 150,000, or 200,000 gallons. In some embodiments, a nitric acid hydrolysis reactor may be smaller than a comparable capacity sulfuric acid hydrolysis reactor.

In a multiple-stage hydrolysis process as described herein, such as a two-stage nitric acid hydrolysis process, one or more processing operations can be used between stages, such as between first and second nitric acid hydrolysis stages, including mechanical degradation, drying, shaking, mixing, chipping, straining, solid-liquid, liquid-liquid, or gas-liquid separation phase separation, decanting, and shearing. Such operations may be used for separation, degradation, attrition, or shearing of an input material.

In some embodiments, a hydrolysis system can include a steam compressor to compress low pressure flash steam. In some embodiments, low pressure flash steam from the first and/or second stage of a nitric acid hydrolysis process may be compressed. By raising the pressure, the low pressure flash steam can be reused in downstream product concentration and/or product distillation operations and significantly reduce the energy requirements of the overall process. In other embodiments, flash steam may be used productively in steam stripping distillation, permitting recovery of useful products contained in the flash stream.

A hydrolysis system for use in the processes described herein can be optimized to produce the greatest yield of products per amount of feedstock, energy required, greenhouse gas emitted, or any combination thereof. Optimization parameters include the type of separations or reactions performed outside of the hydrolysis reactors, and the conditions of the hydrolysis reactors. In some embodiments, degradation and/or hydrolysis of the feedstock material may be reduced or increased due to impact on energy consumption or product yield.

In bioproduct, e.g., biofuel, production processes and systems described herein, a feedstock hydrolysis process as described herein and a fermentation process are coupled to process feedstock in a continuous manner. The continuous operation may be designed such that accumulation of materials between the hydrolysis unit and fermentor is avoided. In some embodiments, a hydrolysis unit may be operated continuously for about or at least about 50, 100, 200, 300, 400, 600, 800, 1000, 1350, 1600, 2000, 2500, 3000, 4000, 5000, 6000, or 8500 hours.

Lignin-containing residue remaining after hydrolysis of a lignocellulosic feedstock may be used as an energy source for the bioproduct, e.g., biofuel, production process described herein and/or as a fuel source for electricity generation. In some embodiments, lignin-containing residue is dried to a liquid content of about 35% to about 15%, e.g., any of about 35%, 30%, 25%, 20%, or 15%, or about 35% to about 30%, about 30% to about 25%, about 25% to about 20%, or about 20% to about 15% or less and the dried residue may be burned as a fuel source for energy or electricity generation, gasified for subsequent combustion or conversion to other chemical products, or converted to other chemical products.

In one embodiment, a method is provided for deconstructing biomass that contains cellulose and hemicellulose for the extraction of sugar molecules from the biomass. The method includes: (a) mechanically disintegrating the biomass in the presence of water and under pressure, thereby producing liquid and/or vapor and solid disintegrated biomass; (b) separating liquid and/or vapor from the biomass, wherein step (b) may be performed after or in conjunction with step (a); (c) contacting the disintegrated biomass with acid in an amount sufficient to depolymerize a polymeric carbohydrate component of the biomass, thereby producing acid impregnated disintegrated biomass; (d) feeding the acid impregnated disintegrated biomass into a digestor through a pressure changing device, wherein the acid impregnated disintegrated biomass is heated in the digestor at a temperature and for an amount of time sufficient to permit the depolymerization reaction to occur; and (e) separating solids from liquids to produce a liquid hydrolysate and residual solids, wherein the hydrolysate contains soluble hemicellulose sugar molecules and the residual solids contain cellulosic fiber, for example, fiber that is at least about 0.35 or 0.37 mm in length. In some embodiments, the acid is nitric acid at a concentration of about 0.1% (w/w) to about 0.5% (w/w). In some embodiments, the digestor is operated at a pressure of about 90 to about 110 psig, a temperature of about 167° C. to about 176° C. and a residence time of about 3 to about 20, about 8 to about 20, or about 5 to about 10 minutes. In some embodiments, the biomass is contacted with steam prior to acid impregnation, which may aid with disintegration of the biomass and extractives removal. In some embodiments, the residual solids are further hydrolyzed, for example, by acid hydrolysis, to release soluble sugar molecules from the cellulose fiber, thereby producing a further hydrolysate that may be used to support microbial fermentation in the processes and systems described herein.

In another embodiment, the method described above for deconstructing biomass that contains cellulose and hemicellulose for the extraction of sugar molecules from the biomass is performed with an acid concentration in step (c), a residence time in step (d), and a temperature in step (d) sufficient to produce a hydrolysate that contains hemicellulose sugars and residual solids that contain cellulosic fiber that is less than about 0.35, 0.30, or 0.28 mm in length. In one embodiment, the residual solids do not contain visible cellulosic fiber. In some embodiments, the acid concentration in step (c) is about 1% (w/w) to about 1.5% (w/w), the residence time in step (d) is about 5 minutes to about 10 minutes, and the temperature in step (d) is about 160° C. to about 180° C. In some embodiments, the acid is nitric acid at a concentration of about 0.05% (w/w) to about 4% (w/w). In some embodiments, the digestor is operated at a pressure of about 90 to about 110 psig, a temperature of about 160° C. to about 180° C., and a residence time of about 4 to about 15 min. In some embodiments, the biomass is contacted with steam prior to acid impregnation, which may aid with disintegration of the biomass and extractives removal. In some embodiments, the residual solids are further hydrolyzed, for example by acid or enzymatic hydrolysis, thereby producing a further hydrolysate that may be used to support microbial fermentation in the processes and systems described herein.

In another embodiment, a method is provided for deconstructing biomass that contains cellulose and hemicellulose for the extraction of sugar molecules from the biomass, including: (a) contacting the biomass with acid in an amount sufficient to depolymerize a polymeric carbohydrate component of the biomass, thereby producing acid impregnated disintegrated biomass; (b) feeding the acid impregnated disintegrated biomass into a digestor through a pressure changing device, wherein the acid impregnated disintegrated biomass is heated in said digestor at a temperature and for an amount of time sufficient to permit the depolymerization reaction to occur; and (c) separating solids from liquids to produce a liquid hydrolysate and residual solids, wherein the hydrolysate comprises hemicellulose sugar molecules and the residual solids contain fiber that is less than about 0.35, 0.30, or 0.28 mm in length. In one embodiment, the residual solids do not contain visible cellulosic fiber. In some embodiments, the acid is nitric acid at a concentration in step (a) is about 0.1% (w/w) to about 5% (w/w), or about 1% (w/w) to about 3% (w/w), the residence time in step (b) is about 8 to about 20 minutes, and the temperature in step (b) is about 160° C. to about 180° C. In some embodiments, the biomass is contacted with steam prior to acid impregnation, which may aid with disintegration of the biomass and extractives removal. In some embodiments, the residual solids are further hydrolyzed, for example by acid or enzymatic hydrolysis, thereby producing a further hydrolysate that may be used to support microbial fermentation in the processes and systems described herein.

Conditioning of Hydrolyzed Feedstock

In some embodiments, hydrolyzed feedstock is "conditioned" to remove inhibitors of microbial growth and/or bioproduct, e.g, biofuel, production, prior to addition of the hydrolyzed feedstock to microbial growth medium. Such inhibitors may include, but are not limited to, organic acids, furans, phenols, soluble lignocellulosic materials, extractives, and ketones Inhibitors present in wood hydrolysates may include, but are not limited to, 5-hydroxyy-methyl furfural (HMF), furfural, aliphatic acids, levulinic acid, acetic acid, formic acid, phenolic compounds, vanillin, dihydroconiferylalcohol, coniferyl aldehyde, vanillic acid, hydroquinone, catechol, acetoguaiacone, homovanillic acid, 4-hydroxy-benzoic acid, Hibbert's ketones, ammonium nitrate and/or other salts, p-coumaric acid, ferulic acid, 4-hydroxybenzoic acid, vanillic acid, syringaldehyde, and glucuronic acid.

Nonlimiting examples of conditioning processes include vacuum or thermal evaporation, overliming, precipitation, adsorption, enzymatic conditioning (e.g., peroxidase, laccase), chemical conversion, distillation, and ion exchange. In one embodiment, conditioning includes contact of hydrolyzed feedstock with an ion exchange resin, such as an anion or cation exchange resin. Inhibitors may be retained on the resin. In one embodiment, the ion exchange resin is an anion exchange resin. Ion exchange resins may be regenerated with caustic, some solvents, potentially including those generated in the bioproduct, e.g., biofuel, production processes described herein, or other known industrial materials. In other embodiments, inhibitors may be precipitated by a metal salt (for example, a trivalent metal salt, for example, an aluminum or iron salt, such as aluminum sulfate or ferric chloride), and/or a flocculant such as polyethylene oxide or other low density, high molecular weight polymers.

In one embodiment, hydrolysate is conditioned on ion exchange resin, such as an anion exchange resin, e.g., Duolite A7, at acidic pH, for example, pH about 2.5 to about 5.5, about 3.5 to about 4.5, or about 2.5, 3, 3.5, 4, 4.5, 5, or 5.5.

In one embodiment, hydrolysate is conditioned with a metal salt, for example, a trivalent metal salt, such as an aluminum or iron salt, e.g., aluminum sulfate or ferric chloride. In some embodiments, the metal salt is added at a concentration of about 1 g/L to about 6 g/L, or about 3 g/L to about 5 g/L. In some embodiments, the pH is adjusted with a base to a basic pH, such as about 9.5 to about 11, or about 9.5, 10, 10.5, or 11, for example, with ammonium hydroxide or ammonia gas.

In some embodiments, microbial growth and/or bioproduct, e.g., biofuel, titer, yield, and/or productivity is increased when conditioned hydrolyzed feedstock is used, in comparison to identical hydrolyzed feedstock which has not been subjected to the conditioning process.

In some embodiments, a microorganism that is tolerant to inhibitors in hydrolyzed feedstock is used, or the microorganism used for bioproduct production develops increased tolerance to inhibitors over time, e.g., by repeated passaging, rendering the conditioning step unnecessary or uneconomical.

In one embodiment, an extractive removal process, as described supra, is used instead of a conditioning process to improved microbial growth and/or bioproduct, e.g., biofuel, titer, yield, and/or productivity. In one embodiment, an extractive removal process, as described supra, is used in addition to a conditioning process to improve microbial growth and/or bioproduct, e.g., biofuel, titer, yield, and/or productivity. An extractive removal process may also be used in some embodiments to generate an additional stream to provide products with commercial value (e.g., sterols) and/or to improve operational parameters (e.g., less resin and regenerant to regenerate the resin (e.g., caustic) required for removal of fermentation and/or bioproduct, e.g., biofuel, production inhibitors.

Fermentation

The bioproduct production process herein includes fermentation of a microorganism that produces a bioproduct, e.g., a biofuel, in an immobilized cell bioreactor (i.e., a bioreactor containing cells that are immobilized on a support, e.g., a solid support). In some embodiments, an immobilized cell bioreactor provides higher productivity due to the accumulation of increased productive cell mass within the bioreactor compared with a stirred tank (suspended cell) bioreactor. In some embodiments, the microbial cells form a biofilm on the support and/or between support particles in the growth medium.

The bioproduct, e.g., biofuel, production process herein includes continuous fermentation of a microorganism (continuous addition of feedstock (e.g., hydrolyzed feedstock) and withdrawal of product stream). Continuous fermentation minimizes the unproductive portions of the fermentation cycle, such as lag, growth, and turnaround time, thereby reducing capital cost, and reduces the number of inoculation events, thus minimizing operational costs and risk associated with human and process error.

Fermentation may be aerobic or anaerobic, depending on the requirements of the bioproduct-producing microorganism.

In some embodiments, an immobilized butanol-producing *Clostridium* strain is fermented anaerobically in a continuous process as described herein. In one embodiment, the support is bone char. In another embodiment, the support is lava rock. In another embodiment, the support is a ceramic/steel support material. In some embodiments, the *Clostridium* strain has an increased tolerance to butanol and/or an increased ability to grow on the support, in comparison to a corresponding parent or wild-type strain, and/or in comparison to *Clostridium saccharobutylicum* B643, *Clostridium saccharobutylicum* P262, *Clostridium saccharoperbutylacetonicum* N1-4, *Clostridium acetobutylicum* 824, and/or *Clostridium beijerinckii* 8524 when grown under identical conditions.

In some embodiments, reactor support materials and implementation thereof are designed so as to maximize reactor productivity. This may include such features as maximizing fermentation gas removal efficiency, liquid-microorganism contact time, minimization of pressure drop, or optimization for cleaning in place.

In some embodiments, bacterial strains, such as *Clostridium* strains, are substituted or rotated periodically to prevent or reduce the occurrence of phage infections.

One or more bioreactors may be used in the bioproduct, e.g., biofuel, systems and processes described herein. When multiple bioreactors are used they can be arranged in series and/or in parallel. The advantages of multiple bioreactors over one large bioreactor include lower fabrication and installation costs, ease of scale-up production, greater ability to control the reaction, and greater production flexibility. For example individual bioreactors may be taken off-line for maintenance, cleaning, sterilization, and the like without appreciably impacting the overall plant production schedule. In embodiments in which multiple bioreactors are used, the bioreactors may be run under the same or different conditions.

In a parallel bioreactor arrangement, hydrolyzed feedstock is fed into multiple bioreactors, and effluent from the bioreactors is removed. The effluent may be combined from multiple bioreactors for recovery of the bioproduct, e.g., biofuel, or the effluent from each bioreactor may be collected separately and used for recovery of the bioproduct.

In a series bioreactor arrangement, hydrolyzed feedstock is fed into the first bioreactor in the series, the effluent from the first bioreactor is fed into a second downstream bioreactor, and the effluent from each bioreactor in the series is fed into the next subsequent bioreactor in the series. The effluent from the final bioreactor in the series is collected and may be used for recovery of the bioproduct, e.g., biofuel. The effluent may be treated between stages (e.g., primary to secondary bioreactor) to increase the overall productivity of the system. Non-limiting examples of processes for such treatment include removal of non-condensable gases and pervaporation for the removal of solvents.

Each bioreactor in a multiple bioreactor arrangement can have the same species, strain, or mix of species or strains of microorganisms or a different species, strain, or mix of species or strains of microorganisms compared to other bioreactors in the series. The fermentation effluent is then removed and sent to separation and recovery.

In some embodiments, feedstock is hydrolyzed in a multi-stage process as described herein, and hydrolysate from each stage is fed to a separate bioreactor. The bioreactors to which the different hydrolysates are fed may contain the same or different microbial species or strains. In one embodiment, the bioreactors to which the different hydrolysates are fed contain different microbial species or strains that have each been optimized for growth on the particular hydrolysate being fed to that bioreactor. In some embodiments, different sets of multiple bioreactors in series are fed hydrolysate from different stages of hydrolysis of the feedstock.

In some embodiments, effluent can be recycled after the harvesting of bioproduct, e.g., biofuel, and used to make the initial fermentation media or a feed stream for future fermentations, thereby allowing maximum utilization of unassimilated and recovered nutrients and minerals. In some embodiments, product is isolated from the effluent and the product reduced effluent is then used as a feedstock for the next bioreactor in the series.

The order of bioreactors in a series can be adjusted to prevent or remove blockage due to excessive microbial growth. For example, when the first fermentor in a series reaches a high level of cell mass, it can be placed second in the series to instead now receive effluent with high product concentration or reduced nutrient levels that may inhibit further cell growth. The timely shifting of the order of fermentors may prevent cell overgrowth and blockage of the bioreactor, which may increase overall productivity of the system and/or reduce operational costs and burdens.

In a continuous process, it is possible to obtain a higher productivity than in batch or fed-batch processes since the cell concentration and the effluent flow rate can be varied independently of each other. In a continuous fermentation, volumetric productivity is calculated by multiplying the product concentration (herein, interchangeably called the "titer") times the nutrient dilution rate (i.e., the rate of changeover of the volume of the bioreactor, or the inverse of the bioreactor residence time). The maximum achievable dilution rate is determined by the concentration of cell mass that one can stably maintain in the bioreactor. At a constant dilution rate (i.e., nutrient consumption rate), as one increases the fermentation titer that can be maintained, the productivity is proportionately increased. However, there may be times when it is desirable to raise the dilution rate temporarily, for a short time relative to the total duration of the fermentation, to remove gas, blockage, or "underperforming" cells.

Immobilized cell bioreactors allow higher concentrations of productive cell mass to accumulate and therefore, the bioreactors can be run at high dilution rates, resulting in a significant improvement in volumetric productivity relative to cultures of suspended cells. Since a high density, steady state culture can be maintained through continuous culturing, with the attendant removal of product containing fermentation broth, smaller capacity bioreactors can be used. Bioreactors for the continuous fermentation of C. acetobutylicum are known in the art. (U.S. Pat. Nos. 4,424,275, and 4,568, 643.)

Bioreactors for use in the bioproduct, e.g., biofuel, production processes and systems herein are designed for continuous operation for at least about 100, 250, 300, 500, 750, 1,000, 1250, 1,500, 2,000, 2,250, 2,500, 3,000, 4,000, 5,000 6,000, or 8,500 hours.

Bioreactor capacities contemplated for use in the bioproduct, e.g., biofuel, production systems herein have a capacity (total nominal volume) of about or at least about 100 L, 1000 L, 6,000 L, 10,000 L, 46,000 L, 50,000 L, 100,000 L, 250,000 L, 270,000 L, 500,000 L, or 1,000,000 L.

Numerous methods of fermentor inoculation are possible including addition of a liquid seed culture to the bottom or the top of the bioreactor and recirculation of the media to encourage growth throughout the bed. Other ways include the addition of a liquid seed culture or impregnated solid support through a port located along the reactor's wall or integrated and loaded with the solid support material. Bioreactor effluent may also be used to inoculate an additional bioreactor and in this case any residual fermentable materials may be converted in the secondary reactor, increasing yield/recovery.

In a similar manner, support material may be added to the reactor through bottom, top, or side loading to replenish support material that becomes degraded or lost from the bioreactor.

Mixing of the bioreactor contents can be achieved through the sparging of sterile gas, e.g., carbon dioxide or N2, which may also serve to prevent contamination of the culture through the maintenance of positive pressure within the fermentor. The evolved gas ($CO_2$, $H_2$) from the fermentation may also be recovered and compressed for utilization in a gas lift or other type reactor to maintain anaerobic, pressurized, well mixed conditions.

Other techniques of mixing culture contents include the use of agitators or the recirculation of fermentation broth, particularly broth returned to the bioreactor after the removal of a fermentation product. In some embodiments, the contents of the bioreactor are not mixed, but may rely on the production and movement of evolved gases to mix contents.

When fermentation conditions are vigorous, the gas produced may be sufficient to prevent the ingress of oxygen to the reactor. For example, an unagitated reactor (e.g., 1000 L reactor), without temperature control and containing fermentation media and fermenting microorganisms, and that is open to the environment (e.g., a tote), may continue to consume feed material and produce bioproducts (e.g., biofuel).

In some embodiments of the bioproduct, e.g., biofuel, production processes and systems herein, immobilized microorganisms are cultured in packed bed bioreactors, also known as plug-flow bioreactors. In other embodiments, the microorganisms are cultured in expanded bed bioreactors. In other embodiments, the microorganisms are cultured in fluidized bed bioreactors. In still further embodiments, the microorganisms are cultured in bioreactors that are designed to operate in "dual mode," i.e., the bioreactors are capable of operating in either packed bed or expanded/fluidized bed mode, e.g., during the same period of operations to increase overall productivity (e.g., removal of detritus, removal of "underperforming" cells). Immobilized cell bioreactors use relatively small sized solid or semi-solid supports that provide a large surface area relative to the volume of the particles, allowing for the microorganisms immobilized on the particles to process large volumes of fluid.

In "packed bed" bioreactors, cells are immobilized on or in structured packing (e.g., Rashig rings, steel/ceramic wool) or semi-solid or solid particles that because of particle size, mechanical restraint and/or low fluid flow rates do not cause or allow for appreciable axial movement of the supporting material.

In contrast, fluidized and expanded bed reactors use semisolid or solid support that is not substantially restrained mechanically so that with sufficient fluid flow, usually an upward-flowing stream, the particles become suspended in the stream or "fluidized," i.e., act as if they are part of the fluid stream. The initial seed support particles may become covered by a biofilm over time and can become fully encapsulated by the biofilm. In some cases, agglomeration of cellular mass may lead to suspended biofilm particles in which there is no "seed" purposefully introduced. Fluid drag on the particles is the primary suspension mechanism, but buoyancy forces can also contribute to the suspension of the particles. Typically, the bioreactors use vertical fluid motion to suspend the particles, but other fluid motion is possible including fluid flow at a direction perpendicular to the vertical axis of the bioreactor. The fluid velocity should be sufficient to suspend the particles, but not large enough to carry them out of the vessel. The fluidization of the bed allows the solid particles to move around the bioreactor, causing the fluid within the bioreactor to thoroughly mix. The magnitude of mixing depends on the extent of particle fluidization achieved in the bioreactor. Fluidized and expanded bed bioreactors require relatively larger amounts of energy to operate compared to packed beds because of the volume of fluid that must be circulated to keep the particles suspended.

A "fluidized bed" bioreactor contains support particles with immobilized microorganisms fluidized throughout the full volume of the bioreactor. Particles exit the bioreactor through the outflow and have to be separated from the effluent liquid and returned to the bioreactor. Support material can be removed, optionally cleaned, and recovered from the effluent stream through the use of settling tanks, dissolved air flotation (DAF) systems, centrifuges, hydrocyclones, filters (e.g., rotary drum), filter aids, dryers, or distillation apparatus.

An "expanded bed" bioreactor contains support particles with immobilized microorganisms fluidized in the bioreactor, but the bioreactor is designed such that the particles are retained in the bioreactor and do not exit through the outflow. An expanded bed bioreactor contains a particle disengagement zone for separating the fluidized particles from the fluid, thereby retaining the particles within the bioreactor. In some embodiments, separation of the particles from the fluid includes slowing the velocity of the fluid. In some embodiments, this is accomplished by increasing the cross sectional area of the bioreactor. As the fluid velocity slows, the particles start to settle out of the fluid. The top section of the particle disengagement zone is free of particles. An outlet can be located at this top portion to remove effluent. In some embodiments, particles are retained by including filters or screens within the bioreactor.

A dual mode, packed bed-fluidized or expanded bed bioreactor allows for the option of conducting fermentations in either mode for the course of a whole fermentation run. Alternately, the fermentation can alternate between modes during the course of a single fermentation. Dual mode bioreactors can have reduced energy usage compared to conventional fluidized or expanded bed bioreactors because fluidization with its requisite increased energy requirement need only be performed, for example, at relatively high cell densities, high product concentrations, or when pH or nutrient inhomogeneities develop that can be corrected through increased mixing of the bioreactor contents.

In various embodiments, a bioreactor may be configured in a vertical, horizontal, or inclined configuration, to maximize gas/liquid separation and/or to improve elution of evolved fermentation gas to improve overall operation and metrics for the production process, e.g., titer, productivity, and/or yield of bioproduct, e.g., biofuel, production. In one embodiment, a bioreactor may be configured as a "trickle bed reactor," in which the material to be reacted is fed into the bed by a slow flow.

In some embodiments, the amount of a bioproduct such as a biofuel, e.g., biobutanol, produced per amount of sugar fed to a bioreactor may be about or at least about 0.1, 0.15, 0.2 0.25, 0.3, 0.33, 0.35, 0.4, 0.45, or 0.5 grams per gram sugar converted, subject to the particular reaction stoichiometry. In some embodiments, the fermentation may utilize about or at least about 40, 50, 60, 65, 70, 75, 80, 85, 90, 95, 96, 97, 98, or 99% of the available sugar. In some embodiments, about or at least about 20, 30, 40, 50, 60, 70, 80, 90, or 95 gallons of biofuel, e.g., biobutanol, is produced per tonne of feedstock, or an amount that approaches the theoretical limit, depending on the feedstock that is used.

In some embodiments, a bioproduct such as a biofuel, e.g., biobutanol, is produced at a productivity of about or at least about 1, 2, 3, 5, 6, 7, 8, 9, 10, 12, 15, 20, 25, 30, 35, 40, 45, or 50 g/L/h.

In some embodiments, bioreactor volumetric productivity and bioproduct, e.g., biofuel, for example, butanol, titer may be improved by reducing the particle size of the immobilized support, which can increase available surface area for cell growth, resulting in higher bioreactor productivity. By fluidizing the solid support in fluidized or expanded bed mode, and by using smaller particles with greater size uniformity, mixing can be greatly improved, permitting optimization of nutrients and pH, further improving fermentation performance.

Some *Clostridium* strains convert sugars into butanol, acetone, and ethanol in a 6:3:1 mass ratio. In some embodiments, strains used in the systems and processes described herein produce a larger proportion of butanol relative to acetone—for example, approximately 75%-25%—with very little ethanol (about 2%). In other embodiments, the ratio of butanol to acetone to ethanol can be about or at least about 58:12:1. In some embodiments, the ratio of butanol to acetone to ethanol is greater than about 58:12:1. In some embodiments, the distribution of products produced by the *Clostridium* strain can be such that the amount of butanol is at least about 70%, the amount of acetone is at least about 25%, and the amount of ethanol is less than about 5%. This higher butanol selectivity results in a higher yield of butanol per unit weight of feedstock. Furthermore, selecting strains having a higher butanol tolerance and higher butanol selectivity in an immobilized environment can result in a higher concentration of butanol in the fermentation broth leaving the reactor, thereby requiring less energy in the product separation phase, and reducing operating costs, cooling water use, and lifecycle GHG emissions.

Fermentation Media

Fermentation media for the production of bioproduct, e.g., biofuel, products contain feedstock, e.g., a hydrolyzed feedstock, as described herein, as a source of fermentable carbohydrate molecules.

As known in the art, in addition to an appropriate carbon source, fermentation media must contain suitable nitrogen source(s), mineral salts, cofactors, buffers, and other components suitable for the growth of the cultures and promotion of the enzymatic pathway necessary for the production of the desired target (e.g., biofuel, such as butanol). In some embodiments, salts and/or vitamin B12 or precursors thereof are included in the fermentation media. In some cases, hydrolyzed feedstock may contain some or all of the nutrients required for growth, minimizing or obviating the need for additional supplemental material.

The nitrogen source may be any suitable nitrogen source, including but not limited to, ammonium salts, yeast extract, corn steep liquor (CSL), and other protein sources including, but not limited to, denatured proteins recovered from distillation of fermentation broth or extracts derived from the residual separated microbial cell mass recovered after fermentation (*Clostridium* extract). Phosphorus may be present in the medium in the form of phosphate salts, such as sodium, potassium, or ammonium phosphates. Sulfur may be present in the medium in the form of sulfate salts, such as sodium or ammonium sulfates. Additional salts include, but are not limited to, magnesium sulfate, manganese sulfate, iron sulfate, magnesium chloride, calcium chloride, manganese chloride, ferric chloride, ferrous chloride, zinc chloride, cupric chloride, cobalt chloride, and sodium molybdate. The growth medium may also contain vitamins such as thiamine hydrochloride, biotin, and para-aminobenzoic acid (PABA). The growth medium may also contain one or more buffering agent(s) (e.g., MES), one or more reducing agent(s) (e.g., cysteine HCl), and/or sodium lactate, which may serve as a carbon source and pH buffer.

Culture Conditions

Optimal culture conditions for various industrially important microorganisms are known in the art. As required, the culture conditions may be anaerobic, microaerotolerant, or aerobic. Aerobic conditions are those that contain oxygen dissolved in the media such that an aerobic culture would not be able to discern a difference in oxygen transfer with the additional dissolved oxygen, and microaerotolerant conditions are those where some dissolved oxygen is present at a level below that found in air or air saturated solutions and frequently below the detection limit of standard dissolved oxygen probes, e.g., less than 1 ppm. The cultures can be agitated or left undisturbed. Typically, the pH of the media changes over time as the microorganisms grow in number, consume feedstock and excrete organic acids. The solubility of $CO_2$, produced during fermentation or present in the media, can also affect pH. The pH of the media can be modulated by the addition of buffering compounds to the initial fermentation media in the bioreactor or by the active addition of acid or base to the growing culture to keep the pH in a desired range. Growth of the culture may be monitored by measuring the optical density, typically at a wavelength of 600 nm, or by other methods known in the art.

For converting sugars to ethanol using *S. cerevisiae*, generally, the temperature is about 25° C. to about 35° C. Useful pH ranges for the conversion medium include about 4.0 to about 6.0, about 4.5 to about 6.0, and about 5.5 to about 5.8. The culture is grown under anaerobic conditions without agitation.

*Clostridium* fermentations are generally conducted under anaerobic conditions. For example, ABE fermentations by *C. acetobutylicum* are typically conducted under anaerobic conditions at a temperature in the range of about 25° C. to about 40° C. Historically, suspension cultures did not use agitators, but relied on evolved or sparged gas to mix the contents of the bioreactors. Cultures, however, can be agitated to ensure more uniform mixing of the contents of the bioreactor. For immobilized cultures, a bioreactor may be run without agitation in a fixed bed (plug flow) or fluidized/expanded bed (well-mixed) mode. Thermophilic bacterial fermentations can reach temperatures in the range of about 50° C. to about 80° C. In some embodiments, the temperature range is about 55° to about 70° C. In some embodiments, the temperature range is about 60° C. to about 65° C. For example, *Clostridium* species such as *C. thermocellum* or *C. thermohydrosulfuricum* may be grown at about 60° C. to about 65° C. The pH of the *Clostridium* growth medium can be modulated by the addition of buffering compounds to the initial fermentation media in the bioreactor or by the active addition of acid or base to the growing culture to keep the pH in a desired range. For example, a pH in the range of about 3.5 to about 7.5, or about 5 to about 7, may be maintained in the medium for growth of *Clostridium*.

Immobilization of Microorganism on Solid Support

Immobilization of the microorganism, from spores or vegetative cells, can be by any known method. In one embodiment, entrapment or inclusion in the support is achieved by polymerizing or solidifying a spore or vegetative cell containing solution. Useful polymerizable or solidifiable solutions include, but are not limited to, alginate, κ-carrageenan, chitosan, polyacrylamide, polyacrylamide-hydrazide, agarose, polypropylene, polyethylene glycol, dimethyl acrylate, polystyrene divinyl benzene, polyvinyl benzene, polyvinyl alcohol, epoxy carrier, cellulose, cellulose acetate, photocrosslinkable resin, prepolymers, urethane, and gelatin.

In another embodiment, the microorganisms are incubated in growth medium with a support. Useful supports include, but are not limited to, bone char, cork, clay, resin, sand, porous alumina beads, porous brick, porous silica, celite (diatomaceous earth), polypropylene, polyester fiber, ceramic, (e.g., porous ceramic, such as porous silica/alumina composite), lava rock, vermiculite, ion exchange resin, coke, natural porous stone, macroporous sintered glass, steel, zeolite, engineered thermal plastic, concrete, glass beads, Teflon, polyetheretherketone, polyethylene, wood chips, sawdust, cellulose fiber (pulp), or other natural, engineered, or manufactured products. The microorganisms may adhere to the support and form an aggregate, e.g., a biofilm.

In another embodiment, the microorganism is covalently coupled to a support using chemical agents like glutaraldehyde, o-dianisidine (U.S. Pat. No. 3,983,000), polymeric isocyanates (U.S. Pat. No. 4,071,409), silanes (U.S. Pat. Nos. 3,519,538 and 3,652,761), hydroxyethyl acrylate, transition metal-activated supports, cyanuric chloride, sodium periodate, toluene, or the like. See also U.S. Pat. Nos. 3,930,951 and 3,933,589.

In one embodiment, immobilized spores, such as those of *Clostridium*, e.g., *C. acetobutylicum*, are activated by thermal shock and then incubated under appropriate conditions in a growth medium whereby vegetative growth ensues. These cells remain enclosed in or on the solid support. After the microorganisms reach a suitable density and physiological state, culture conditions can be changed for bioproduct, e.g., biofuel, production. If the immobilized cells lose bioproduct, e.g., biofuel, production, they can be reactivated by first allowing the cells to sporulate before repeating the thermal shock and culture sequence.

Vegetative cells can be immobilized in different phases of their growth. For microorganisms that display a biphasic culture, such as *C. acetobutylicum* with its acidogenic and solventogenic phases, cells can be immobilized after they enter the desired culture phase in order to maximize production of the desired products, where in the case of *C. acetobutylicum* it is the organic acids acetic acid and butyric acid in the acidogenic phase and the solvents acetone, butanol and ethanol in the solventogenic phase. Alternatively, biphasic cells can be immobilized in the acidogenic phase and then adapted for solvent production.

In some embodiments, microorganisms to be immobilized in a bioreactor are introduced by way of a cell suspension. Generally, these microorganisms are dispersed in the media as single cells or small aggregates of cells. In other embodiments, the microorganisms are introduced into the bioreactor through the use of suspended particles that are colonized by the microorganisms. These suspended particles can be absorbed onto the solid support and frequently are of sufficiently small size that they can enter and become immobilized in the pore structures of the solid support. Typically, regardless of the suspended particle size, microorganisms can be transferred by contact with the solid support. A biofilm on the introduced particles can transfer to and colonize these new surfaces. In some embodiments, the desired characteristics of the microorganisms can only be maintained by culturing on a solid support, thereby necessitating the use of small colonized particle suspensions for seeding a solid support in a bioreactor.

Support for Immobilized Microbial Growth

In some embodiments, a bioproduct, e.g., biofuel, producing microorganism is grown in an immobilized form on a solid or semi-solid support material in a bioreactor as described herein. In some embodiments, the support comprises a porous material. Non-limiting examples of suitable support materials include bone char, synthetic polymers, natural polymers, inorganic materials, and organic materials.

Natural polymers include organic materials such as cellulose, lignocellulose, hemicellulose, and starch. Organic materials include feedstock such as plant residue and paper. Composites of two or more materials may also be used such as mixtures of synthetic polymer with natural plant polymer.

Examples of semi-solid media include alginate, κ-carrageenan and chitosan, polyacrylamide, polyacrylamide-hydrazide, agarose, polypropylene, polyethylene glycol, dimethyl acrylate, polystyrene divinyl benzene, polyvinyl benzene, polyvinyl alcohol, epoxy carrier, cellulose, cellulose acetate, photocrosslinkable resin, prepolymers, urethane, and gelatin. Examples of solid support include cork, clay, resin, sand, porous alumina beads, porous brick, porous silica, celite, wood chips or activated charcoal.

Suitable inorganic solid support materials include inorganic materials with available surface hydroxy or oxide groups. Such materials can be classified in terms of chemical composition as siliceous or nonsiliceous metal oxides. Siliceous supports include, inter alia, glass, colloidal silica, wollastonite, cordierite, dried silica gel, bentonite, and the like. Representative nonsiliceous metal oxides include alumina, hydroxy apatite, and nickel oxide.

In some embodiments, the support material is selected from bone char, polypropylene, steel, diataomaceous earth, zeolite, ceramic, (e.g., porous ceramic, such as porous silica/alumina composite), engineered thermal plastic, clay brick, concrete, lava rock, wood chips, polyester fiber, glass beads, Teflon, polyetheretherketone, polyethylene, vermiculite, ion exchange resin, cork, resin, sand, porous alumina beads, coke, natural porous stone, macroporous sintered glass, or a combination thereof. In one embodiment, the support material is bone char. Useful support material has a high surface area to volume ratio such that a large amount of active, productive cells can accumulate in the bioreactor. Useful supports may contain one or more macrostructured components containing one or more useful support material(s) that promotes good fluid-mechanical properties, for example, a wire mesh/gauze packing material used for traditional distillation tower packing.

In some embodiments, the support material comprises a surface area of at least about 100 $m^2/m^3$. In some embodiments, the support material comprises a bulk density of at least about 0.15 g/cm3. In some embodiments, the support material comprises a ball-pan hardness number of at least about 60. In some embodiments, the support material comprises a yield strength of at least about 20 MPa.

The particle size for the support material will vary depending upon bioreactor configuration and operation parameters. In some embodiments, the support material is sized by sieving. In some embodiments, the particles are classified by the sieve number of the mesh that they can pass through. In some embodiments, the particles are sieved with a mesh that has a U.S. Sieve Number of 3½, 4, 5, 6, 7, 8, 10, 12, 14, 16, 18, 20, 25, 30, 35, 40, 45, 50, 60, or 70. In some embodiments, the particles are sieved at least twice, first using a mesh with larger openings followed by a mesh with smaller openings to yield particles within a defined particle size distribution range. In some embodiments, the particles are at least about 100 µm, 200 µm, 300 µm, 400 µm, 500 µm, 600 µm, 700 µm, 800 µm, 900 µm, 1000 µm, 1,100 µm, 1,200 µm, 1,300 µm, 1,400 µm, 1,500 µm, 1,600 µm, 1,700 µm, 1,800 µm, 1,900 µm, 2,000 µm, 3,000 µm, 4,000 µm, 5,000 µm, 6,000 µm, 7,000 µm, 8000 µm, 9,000 µm, 10,000 µm, 12,500 µm, 15,000 µm, 17,500 µm, 20,000 µm, 22,500 µm, or 25,000 µm in diameter. In some embodiments, the particles are less than about 100 µm, 200 µm, 300 µm, 400 µm, 500 µm, 600 µm, 700 µm, 800 µm, 900 µm, 1000 µm, 1,100 µm, 1,200 µm, 1,300 µm, 1,400 µm, 1,500 µm, 1,600 µm, 1,700 µm, 1,800 µm, 1,900 µm, 2,000 µm in diameter. In further embodiments, at least about 80%, 85%, 90%, 95%, or 100% of the particle have diameters that are in the range of about 100-400 µm, 100-600 µm, 100-800 µm, 200-500 µm, 200-800 µm, 200-1000 µm, 400-800 µm, 400-1000 µm, 500-1000 µm, 600-1,200 µm, 800-1,400, µm 1,000-1,500, µm 1,000-2000 µm, 2,000-4,000 µm, 4,000-6,000 µm, 5,000-12,000 µm, 3,000-15,000 µm, or 6,000-25,000 µm. In some embodiments, the particle diameters are the equivalent diameters, a parameter that takes into account the irregular shapes of the individual particles.

Ideally, the semi-solid or solid support material should have a high surface area. This can be achieved through the use of small sized particles, particles with high porosity, or a combination thereof. In some embodiments, the surface area of the particles is at least about 0.003 $m^2/g$, 0.01 $m^2/g$, 0.02 $m^2/g$, 0.05 $m^2/g$, 0.1 $m^2/g$, 0.5 $m^2/g$, 1 $m^2/g$, 5 $m^2/g$, 10 $m^2/g$, 25 $m^2/g$, 50 $m^2/g$, 75 $m^2/g$, 100 $m^2/g$, 125 $m^2/g$, 150 $m^2/g$, 175 $m^2/g$, 200 $m^2/g$, 225 $m^2/g$, 250 $m^2/g$, 275 $m^2/g$, 300 $m^2/g$, 325 $m^2/g$, 350 $m^2/g$, 375 $m^2/g$, 400 $m^2/g$, 425 $m^2/g$, 450 $m^2/g$, 500 $m^2/g$, 600 $m^2/g$, 700 $m^2/g$, 800 $m^2/g$, 900 $m^2/g$, 1000 $m^2/g$, or 2000 $m^2/g$. Additionally, the bulk density should be sufficiently high so that the smallest particles settle out of the fluid stream in the column expansion zone and/or particle disengagement zone and are thereby retained in the bioreactor. In some embodiments, the bulk density of the support is at least about 0.1 $g/cm^3$, 0.2 $g/cm^3$, 0.3 $g/cm^3$, 0.4 $g/cm^3$, 0.5 $g/cm^3$, 0.6 $g/cm^3$, 0.7 $g/cm^3$, 0.8 $g/cm^3$, 0.9 $g/cm^3$, 1.0 $g/cm^3$, 1.1 $g/cm^3$, 1.2 $g/cm^3$, or 1.3 $g/cm^3$. The support material should have sufficient hardness to resist abrasion and thereby avoid appreciable dust formation when the support particles touch or collide with each other. In some embodiments, the support has a ball-pan hardness number of at least about 20, 40, 60, 80, 100, 120, 140, 160 or 200. The support material should also have sufficient tensile strength to resist shattering due to internal stresses, which may be caused by the growth of biofilms inside support material pores. In some embodiments, the support has a yield strength of at least about 20 MPa, 40 MPa, 60 MPa, 80 MPa, 100 MPa, 120 MPa, 140 MPa, 160 MPa, 180 MPa, 200 MPa, 300 MPa, or 400 MPa. The support material should also have the ability to resist being crushed by the accumulated weight of material above it. Crush strength is another measurement of the mechanical strength of the support and is typically a function of the composition, shape, size, and porosity of the material (increase in port volume may negatively impact particle strength). In some embodiments, the crush strength is at least about 8 kg.

In some embodiments, the support material is chosen to support growth of the fermenting bioproduct, e.g., biofuel, producing microorganism as a biofilm. The biofilm may grow on exterior surfaces of support particles, in the fluid space between support particles, and/or on surfaces in the interior of pores of the support material.

Microorganisms

The systems and processes described herein include one or more microorganism(s) that is (are) capable of producing a bioproduct, e.g., biofuel. In embodiments in which two or more microorganisms are used, the microorganisms may be the same or different microbial species and/or different strains of the same species.

In some embodiments, the microorganisms comprise bacteria or fungi. In some embodiments, the microorganisms comprise a single species. In some embodiments, the microorganisms comprise a mixed culture of strains from the same species. In some embodiments, the microorganism comprises a mixed culture of different species. In some embodiments, the microorganism comprises an environmental isolate or strain derived therefrom.

In some embodiments of the processes and systems described herein, different species or strains, or different combinations of two or more species or strains, are used in different bioreactors with different hydrolyzed feedstocks as a carbohydrate source.

In some embodiments, a fungal microorganism is used, such as a yeast. Examples of yeasts include, but are not limited to, *Saccharomyces cerevisiae, S. bayanus, S. carlsbergensis, S. Monacensis, S. Pastorianus, S. uvarum* and *Kluyveromyces* species. Other examples of anaerobic or aerotolerant fungi include, but are not limited to, the genera *Neocallimastix, Caecomyces, Piromyces* and other rumen derived anaerobic fungi.

In some embodiments, a bacterial microorganism is used, including Gram-negative and Gram-positive bacteria. Non-limiting examples of Gram-positive bacteria include bacteria found in the genera of *Staphylococcus, Streptococcus, Bacillus, Mycobacterium, Enterococcus, Lactobacillus, Leuconostoc, Pediococcus*, and *Propionibacterium*. Non-limiting examples of specific species include *Enterococcus faecium* and *Enterococcus gallinarium*. Non-limiting examples of Gram-negative bacteria include bacteria found in the genera *Pseudomonas, Zymomonas, Spirochaeta, Methylosinus, Pantoea, Acetobacter, Gluconobacter, Escherichia* and *Erwinia*.

In one embodiment, the bacteria are *Clostridium* species, including but not limited to, *Clostridium saccharobutylicum, Clostridium acetobutylicum, Clostridium beijerinckii, Clostridium puniceum*, and environmental isolates of *Clostridium*.

Further examples of species of *Clostridium* contemplated for use in this invention can be selected from *C. aurantibutyricum, C. butyricum, C. cellulolyticum, C. phytofermentans, C. saccharolyticum, C. saccharoperbutylacetonicum, C. tetanomorphum, C. thermobutyricum, C. thermocellum, C. puniceum, C. thermosaccharolyticum*, and *C. pasterianum*.

Other bacteria contemplated for use in the processes and systems herein include *Corynebacteria*, such as *C. diphtheriae, Pneumococci*, such as *Diplococcus pneumoniae, Streptococci*, such as *S. pyogenes* and *S. salivarus, Staphylococci*, such as *S. aureus* and *S. albus, Myoviridae, Siphoviridae*, Aerobic Spore-forming *Bacilli, Bacilli*, such as *B. anthracia, B. subtilis, B. megaterium, B. cereus, Butyrivibrio fibrisolvens*, Anaerobic Spore-forming *Bacilli, Mycobacteria*, such as *M. tuberculosis hominis, M. bovis, M. avium, M. paratuberculosis, Actinomycetes* (fungus-like bacteria), such as, *A. israelii, A. bovis, A. naeslundii, Nocardia asteroides, Nocardia brasiliensis*, the *Spirochetes, Treponema pallidium, Treponema pertenue, Treponema carateum, Borrelia recurrentis, Leptospira icterohemorrhagiae, Leptospira canicola, Spirillum minus, Streptobacillus moniliformis, Trypanosomas, Mycoplasmas, Mycoplasma pneumoniae, Listeria monocytogenes, Erysipelothrix rhusiopathiae, Streptobacillus monilformis, Donvania granulomatis, Bartonella bacilliformis, Rickettsiae, Rickettsia prowazekii, Rickettsia mooseri, Rickettsia rickettsiae*, and *Rickettsia conori*. Other suitable bacteria may include *Escherichia coli, Zymomonas mobilis, Erwinia chrysanthemi*, and *Klebsiella planticola*.

In some embodiments, the microorganisms comprise the genera *Clostridium, Enterococcus, Klebsiella, Lactobacillus*, or *Bacillus*. In some embodiments, the microorganisms comprise *Clostridium acetobutylicum, Clostridium beijerinckii, Clostridium puniceum, Clostridium saccharobutylicum, Enterococcus faecium, Enterococcus gallinarium, Clostridium aurantibutyricum, Clostridium aurantibutyricum, Clostridium tetanomorphum*, or *Clostridium thermosaccharolyticum*.

In some embodiments, the microorganisms are obligate anaerobes. Non-limiting examples of obligate anaerobes include *Butyrivibrio fibrosolvens* and *Clostridium* species.

In other embodiments, the microorganisms are microaerotolerant and are capable of surviving in the presence of small concentrations of oxygen. In some embodiments, microaerobic conditions include, but are not limited, to fermentation conditions produced by sparging a liquid media with a gas of at least about 0.01% to at least 5% or more $O_2$ (e.g., 0.01%, 0.05%, 0.10%, 0.50%, 0.60%, 0.70%, 0.80%, 1.00%, 1.20%, 1.50%, 1.75%, 2.0%, 3%, 4%, 5% or more $O_2$). In another aspect, the microaerobic conditions include, but are not limited to, culture conditions with at least about 0.05 ppm dissolved $O_2$ or more (e.g., 0.05, 0.075, 0.1, 0.15, 0.2, 0.3, 0.4, 0.5, 0.6, 0.8, 1.0, 2.0, 3.0, 4.0, 5.0, 8.0, 10.0, ppm or more).

Microbial strains may be optimized, mutated, or otherwise selected for desirable characteristics. For example, parent strains of bacteria and fungi may be used for the development of higher product tolerant mutants. See, for example, PCT/US09/40050. Sources of such parent strains include established culture collections, and researchers in universities, government institutions, or companies.

Alternatively, parent strains can be isolated from environmental samples such as wastewater sludge from wastewater treatment facilities including municipal facilities and those at chemical or petrochemical plants. The latter are especially attractive as the isolated microorganisms can be expected to have evolved over the course of numerous generations in the presence of high product concentrations and thereby have already attained a level of desired product tolerance that may be further improved upon.

Parent strains may also be isolated from locations of natural degradation of naturally occurring feedstocks and compounds (e.g., a woodpile, a saw yard, under fallen trees, landfills). Such isolates may be advantageous since the isolated microorganisms may have evolved over time in the presence of the feedstock and thereby have already attained some level of conversion and tolerance to these materials that may be further improved upon.

Individual species or mixed populations of species can be isolated from environmental samples.

In some embodiments, environmental isolates and/or microbial consortiums are used to generate microbial consortiums that have increased product tolerance. Isolates, including microbial consortiums can be collected from numerous environmental niches including soil, rivers, lakes, sediments, estuaries, marshes, industrial facilities, etc. In some embodiments, the microbial consortiums are strict anaerobes. In other embodiments, the microbial consortiums are obligate anaerobes. In some embodiments, the microbial consortiums are facultative anaerobes. In still other embodiments, the microbial consortiums do not contain species of *Enterococcus* or *Lactobacillus*.

When mixed populations of specific species or genera are used, a selective growth inhibitor for undesired species or genera can be used to prevent or suppress the growth of these undesired microorganisms.

In some embodiments, cocultures are utilized. For example, one microorganism may secrete enzymes into the media that break down a feedstock into constituent compounds that can be utilized by another microorganism. For example, ethanol may be produced from a coculture of *Clostridium thermocellum* and *C. thermohydrosulfuricum* (Eng et al. (1981) *Applied and Environmental Microbiology* 41 (6): 1337-1343).

In some embodiments, the microorganisms comprise one or more heterologous genes, the expression of which increases the product tolerance of the microorganisms. In some embodiments, the one or more heterologous genes are introduced into the microorganism before adaptation on a solid support or selection for product tolerance, while in other embodiments, the one or more heterologous genes are introduced into the microorganisms after adaptation or selection for product tolerance.

In some embodiments, the microorganisms are engineered to over-express endogenous genes that increase the product tolerance of the microorganisms. In some embodiments, the microorganisms comprise additional copy numbers of endogenous genes that increase resistance to products. In certain embodiments, the product tolerant microorganisms are not *E. coli* and the heterologous or over-expressed genes are not yfdE, yhhL, yhhM, and csrC. In other embodiments, the microorganisms are not recombinant microorganisms that have increased expression of heat shock proteins. In still other embodiments, the microorganisms are not recombinant microorganisms that comprise a heterologous gene that encodes a polypeptide that exports butanol out of the microorganism.

In some embodiments, the microorganism is a *Clostridium* strain that possesses one or more phenotypic characteristics selected from increased butanol tolerance, increased tolerance to inhibitors of fermentation, low butyric acid and/or acetic acid accumulation, increased stability in continuous fermentation, increased butanol titer, production of biofuel with increased butanol to acetone ratio, increased yield of butanol per unit of feedstock, increased yield of butanol per unit of cellular biomass, increased oxygen tolerance, increased ability to adhere to a solid support, and decreased ability to sporulate, relative to a wild-type or parent *Clostridium* strain and/or relative to *Clostridium saccharobutylicum* B643 (Contag et al. (1990) *Applied Environmental Microbiology* 56:3760-65), *Clostridium saccharobutylicum* P262 (ATCC BAA-11), *Clostridium saccharoperbutylacetonicum* N1-4 ATCC 27021, *Clostridium acetobutylicum* ATCC 824 and/or *Clostridium beijerinckii* ATCC 51743.

In some embodiments, the microorganism is a strain, for example, a *Clostridium* strain, e.g., *Clostridium acetobutylicum, Clostridium saccharobutylicum, Clostridium saccharoperbutylacetonicum*, or *Clostridium beijerinckii*, having tolerance to at least about 2%, 2.5%, 5%, 10%, 12%, or 15% biofuel, in the growth medium by weight, for example, tolerance to at least about 2%, 2.5%, 5%, 10%, 12%, or 15% butanol in the growth medium by weight.

In some embodiments, the microorganism is a mutant strain having at least about 125%, 150%, 200%, 250%, 500%, or 1,000% increased tolerance to a biofuel in the growth medium, for example, at least about 125%, 150%, 200%, 250%, 500%, or 1,000% increased tolerance to butanol in the growth medium, measured by growth of the microorganism in comparison to a corresponding non-mutant microorganism, for example, the corresponding parent or wild-type microorganism, when grown under identical conditions. In some embodiments, the mutant strain is a *Clostridium* strain, e.g., *Clostridium acetobutylicum, Clostridium* saccharobutylicum, *Clostridium saccharoperbutylacetonicum*, or *Clostridium beijerinckii*, having at least about 125%, 150%, 200%, 250%, 500%, or 1,000% increased tolerance to a biofuel, e.g., butanol, in the growth medium, in comparison to *Clostridium saccharobutylicum* B643, *Clostridium saccharobutylicum* P262, *Clostridium saccharoperbutylacetonicum* N1-4 ATCC 27021, *Clostridium acetobutylicum* ATCC 824, and/or *Clostridium beijerinckii* ATCC 51743, when grown under identical conditions.

In some embodiments, a strain that produces a bioproduct, e.g., a biofuel, such as butanol, efficiently from pentoses, such as xylose and other sugars found in hemicellulose hydrolysates, may be obtained by environmental isolation or mutation of a parent strain. Some strains may metabolize insoluble substrates, e.g., xylan, utilizing endogenous enzymatic activities, such as xylanase and/or amylase. Other strains may degrade inulin and/or pectin without addition of exogenous enzymes. Other strains may metabolize a variety of sugars and convert them to products. Such strains may be used as a basis for strain engineering or mutagenesis. A diverse strain library can allow for the rotation of strains in fermentation, preventing phage contamination and providing diversity for metabolism of different feed hydrolysates.

Recovery Processes

The fermentation effluent containing the bioproduct may be concentrated and/or purified. In some embodiments, the product is concentrated prior to further purification using any suitable concentration technique known in the art, including but not limited to distillation, steam stripping distillation, mechanical vapor recompression (MVR) distillation, vacuum distillation, pervaporation, and liquid-liquid extraction.

In one embodiment, the bioproduct is a biofuel, for example, butanol, ethanol, and/or acetone. In some embodiments, primary components of the fermentation effluent are butanol, acetone, ethanol, butyric acid, and acetic acid, all of which may be recovered and used as starting materials for downstream chemical syntheses to produce derivatives and/or further chemical products. Secondary components of the fermentation effluent include, but are not limited to, proteins and other products of metabolic pathways, which may also be used as starting materials for production of derivatives or further chemical products. Secondary components include, but are not limited to, solvents, biomolecules (e.g., proteins (e.g., enzymes), polysaccharides), organic acids (e.g., formate, acetate, butyrate, propionate, succinate), alcohols (e.g., methanol, propanol, isopropanol, hexanol), vitamins, sugar alcohols (e.g., xylitol). Further, chemical compounds generated during acid hydrolysis of feedstock, including but not limited to, furfural, formic acid, levulinic acid, and HMF, may also be separated from the fermentation effluent and used as starting materials for production of derivatives or further chemical products.

In some embodiments, fermentation product streams from multiple bioreactors or series of bioreactors are combined prior to further purification. In some embodiments, fermentation product streams from multiple bioreactors or series of bioreactors are fed to separate purification units. For example, a fermentation product stream from a first bioreactor processing C5 sugars can be combined with fermentation products from a second bioreactor processing C5 and C6 sugars. Alternatively, the product streams from the first and second bioreactors may be processed separately.

In other configurations, fermentation broth may be separated from products in situ (i.e., extractive fermentation) by any of a variety of methods (e.g., LLE (liquid-liquid extraction), vacuum distillation, stripping, pervaporation), to increase the total productivity of the overall conversion process. For example, butanol and other products may be recovered from the bioreactor by condensation of the sparging and naturally occurring gases.

In other configurations, one or more processing steps may be carried out between fermentation stages (e.g., between primary and secondary reactors in a series) to enhance the overall system from an economic, operability, maintenance, energy, and/or water use perspective.

In some embodiments, MVR distillation is used for concentration of a bioproduct, such as a biofuel, from the microbial fermentation medium. In this approach, overhead vapors generated as part of the distillation process are mechanically compressed, and the resulting latent heat released from the condensation process is supplied to the evaporation process. In some embodiments, MVR reduces separation energy requirements by at least about 80% in comparison to conventional distillation.

In some embodiments, a conventional distillation process is used for the remaining product separation, optionally with thermally cascaded heat integration. Previously, separation of biobutanol from fermentation media has been hindered due to the impact of secondary compounds on the separation process. Distillation avoids this issue since surface chemistry is not the basis for the separation.

In some embodiments, process equipment is selected to optimize energy, water, and/or other metric of interest. In the case of energy use, this may include the addition of heat exchangers to recover stream enthalpy for useful purposes, or to avoid complete condensation or evaporation of feed and/or overhead streams.

In one embodiment of a butanol recovery process, fermentation broth (effluent) is passed from a fermentation module to a product recovery module in which solvents (e.g., butanol, acetone, ethanol) and other volatile compounds are separated from water and less volatile compounds such as biomass residue, carbohydrates and hydrolysis generated sugars. Some water accompanies the solvents and other volatiles in the overhead of the product recovery module. The volatile-water stream may or may not be passed to a decanting operation to increase the effectiveness and efficiency of the remaining product separation. The product recovery overhead stream is passed to a high-low volatile splitter module in which two (or more) streams are generated—a light fraction, a heavy fraction and potentially a mixed solvent side draw. The mixed solvent side draw may contain primarily acetone, ethanol, and water. The light fraction contains primarily acetone, ethanol and water. Optionally, the light fractions are sent to an acetone column in which acetone is separated from the other components in the feed stream (e.g., ethanol and water). The lower volatility stream exiting the high-low volatility splitter (heavy fraction) is passed to a decanter where a phase separation occurs. The upper phase is an organic rich phase which is passed to a butanol column. For example, the upper phase may contain about 80% butanol and about 20% water. The operating temperature and pressure affect the partitioning of compounds in the phases. The phase separation unit may be in fluid contact with a butanol column and a water column. The butanol column separates butanol from an overhead stream primarily comprised of a butanol-water azeotropic stream. The azeotrope stream is returned to the decanter (phase separation operation) for further separation. The aqueous phase of the decanter, which may contain nearly or about 9% butanol and about 89% water, is passed to the aqueous column in which water is separated from a mostly butanol-water azeotrope. The butanol-water azeotrope is returned to the decanter for further processing.

In some embodiments, butyric acid is removed from the butanol product stream formed in the distillation process. In one embodiment, butyric acid is adsorbed from the butanol product stream. For example, a tertiary amine ion-exchange resin may be used for adsorption of butyric acid. In another embodiment, butanol and butyric acid are separated by distillation. In a further embodiment, butanol and butyric acid are separated by pervaporation. In one embodiment, the butyric acid is removed and may be sold as a chemical product. In another embodiment, the butyric acid is returned to the solventogenic portion of the process, and may be added to the fermentation medium in the bioreactor as a feedstock which may be converted to butanol by the fermenting microorganism.

In some embodiments, furfural is removed from the butanol product stream formed in the distillation process. In one embodiment, furfural is adsorbed from the butanol product stream. For example, a tertiary amine ion-exchange resin or activated carbon may be used for adsorption of furfural. In another embodiment, butanol and furfural are separated by pervaporation. In a further embodiment, butanol and furfural are separated from one another through the use of a solvent, such as triocyl-phosphine oxide (TOPO). In one embodiment, the furfural is removed and may be sold as a chemical product.

In some embodiments, other products are removed from the butanol product stream to remove impurities from the butanol product stream and recovered as useful products, for example, acetic acid, butyric acid, HMF, extractives.

Biobutanol produced according to the methods described herein may also serve as a platform molecule for the production of other compounds. For example, butanol may be converted into propylene, from which a wide variety of plastics and other compounds may be produced. A mixture of butanol, dibutyl ether (a derivative of butanol), and plant oil in specified proportions may constitute a full performance diesel fuel. In addition, through well-understood chemistry involving dehydration of butanol followed by oligomerization through the use of a catalyst, butanol may be converted into full performance jet fuel.

Biobutanol produced according to the methods described herein may also be used as an intermediate chemical for producing other chemical products, including but not limited to, butyl acrylate, n-butyl acetate, and glycol ethers. It may also be dehydrated to produce 1-butene, which may be oligomerized to produce other products, including but not limited to, jet fuel, diesel fuel, lubricants, or alpha olefins. Butanol may also be used directly to produce butene derivatives. Any of these derivatives of butanol may be produced using chemical processes that are well known in the art.

Continuous Process

A continuous process for bioproduct, e.g., biofuel, production is provided. In a continuous production process herein, a carbohydrate-containing feedstock is continuously pretreated to produce soluble sugar molecules, the pretreated feedstock containing soluble sugar molecules is continuously fed to one or more bioreactors for microbial production of the bioproduct, e.g., biofuel, the bioproduct is continuously produced by immobilized microorganism(s) in the one or more bioreactors, and bioproduct-containing effluent, i.e., fermentation broth, is continuously withdrawn from the one or more reactors, for the duration of fermentation. In some embodiments, the feedstock is continuously hydrolyzed to release soluble sugar molecules. In one embodiment, the feedstock is lignocellulosic feedstock, and is hydrolyzed with nitric acid to release soluble sugar molecules from cellulose and hemicellulose, as described supra.

In some embodiments, the continuous process may also include downstream continuous concentration and/or purification processes for recovery of the bioproduct, e.g., biofuel, product, wherein continuously withdrawn effluent is continuously processed in one or more concentration and/or purification processes to produce a bioproduct.

In some embodiments, the process may also include a conditioning process to remove inhibitors of microbial growth or bioproduct, e.g., biofuel, production, as described herein. The conditioning process may operate continuously downstream from a feedstock hydrolysis process, and upstream from the bioreactor(s), and conditioned hydrolyzed feedstock may be continuously fed to the bioreactor for the duration of fermentation.

In some embodiments, the process may also include deconstruction of the feedstock and/or removal of extractives from the feedstock, as described herein. Deconstruction and/or removal of extractives may be continuous or may occur prior to or periodically throughout the continuous process.

In some embodiments, the process operates continuously for at least about 50, 100, 200, 300, 400, 600, 800, 1000, 1350, 1600, 2000, 2500, 3000, 4000, 5000, 6000, 7000, 8000, or 8400 hours.

A "continuous" process as described herein may include periodic or intermittent partial or complete shutdowns of one or more parts of the bioproduct, e.g., biofuel, production system for processes such as maintenance, repair, regeneration of resin, etc.

Continuous fermentation, with constant feed of hydrolyzed feedstock and withdrawal of product-containing microbial broth, can minimize the unproductive portions of a fermentation cycle, such as lag, growth, and turnaround time, thereby reducing the capital cost, and can reduce the number of inoculation events, thus minimizing operational costs and risk associated with human and process error.

The continuous methods and systems described herein can utilize one or more, e.g., one, two, or three or more, bioreactors. When multiple (two or more) bioreactors are used, they may be arranged in parallel, series, or a combination thereof. The bioreactors can grow the same or different strains of microorganism(s). The strains can be different based on the type of sugar they metabolize to maximize bioproduct, e.g., biofuel, production. For example, a first bioreactor or multiple bioreactors arranged in parallel, series, or a combination thereof can grow a strain that has been selected to metabolize C5 sugars and a second bioreactor or multiple bioreactors arranged in parallel, series, or a combination thereof can grow another strain that has been selected to metabolize C5 and C6 sugars. The bioreactors are coupled to an upstream feedstock hydrolysis unit, and may also be coupled to a downstream recovery/separation unit. In some embodiments, the connection may be interdigitated, such that some product separation may occur between primary and/or secondary and/or further reactors in series.

A first bioreactor or multiple bioreactors arranged in parallel, series, or a combination thereof with a strain that metabolizes C5 sugars can be coupled to an upstream first stage hydrolysis module of a nitric acid hydrolysis unit for hydrolysis of lignocellulosic feedstock. A second set of bioreactors or multiple bioreactors arranged in parallel, series, or a combination thereof with a strain that metabolizes C5 and C6 sugars can be coupled to an upstream second stage hydrolysis module of a nitric acid hydrolysis unit for hydrolysis of a lignocellulosic feedstock. Alternatively, the same bioreactor or multiple bioreactors arranged in parallel, series, or a combination thereof may be used for conversion of both C5 and C6 sugars to bioproduct, e.g., biofuel. For example, both first and second stage nitric acid hydrolysates of a lignocellulosic feedstock may be added either separately or as a combined mixture to the bioreactor(s).

In some embodiments of continuous biofuel production processes and systems described herein, butanol may be produced by a microbial strain, such as a *Clostridium* strain, at a titer of about or at least about 5, 6, 7, 8, 10, 12, 15, 20, 25, 30, 40, 50, 60, 70, 80, or 90 g butanol per liter, or about 5 to about 90, about 5 to about 10, about 8 to about 20, about 15 to about 30, about 25 to about 50, about 40 to about 80, or about 60 to about 90 g butanol per liter. Titer may be affected by ambient conditions (e.g., pressure/temperature) and composition (acetone, salts, etc.). In some embodiments of continuous biofuel production processes and systems described herein, butanol may be produced by a microbial strain, such as a *Clostridium* strain, with a yield of about or at least about 30, 35, 40, 50, or 60% or about 30% to about 60%, about 40% to about 60%, or about 50% to about 60%. In some embodiments of continuous biofuel production processes and systems described herein, butanol may be produced by a microbial strain, such as a *Clostridium* strain, with a productivity of about or at least about 1, 3, 5, 10, 15, or 20 g, butanol per liter per hour, or about 1 to about 20, about 3 to about 10, about 5 to about 15, or about 10 to about 20 g butanol per liter per hour.

In some embodiments, water saturated butanol may be skimmed off the top of the liquid or separated by equipment known in the art for the separation of two liquid phases in the bioreactor, for further processing/product recovery operations.

System for Bioproduct Production

The invention provides a system for continuous production of a bioproduct, e.g., biofuel, i.e., for conducting a continuous bioproduct production process as described herein. The system contains a feedstock hydrolysis unit upstream from and in fluid communication with one or more bioreactor(s). A carbon-containing feedstock is continuously hydrolyzed in the hydrolysis unit to produce soluble sugar molecules, and the hydrolysate is continuously fed to the bioreactor(s) as a carbon source to support microbial growth. One or more immobilized microorganism(s) in the bioreactor(s) continuously convert the hydrolysate into a bioproduct, e.g., biofuel, and bioproduct-containing effluent is continuously withdrawn from the system.

In some embodiments, the system contains multiple bioreactors arranged in parallel, series, or a combination thereof. In one embodiment, multiple bioreactors in parallel are all in fluid communication with a single hydrolysis unit or multiple bioreactors in parallel are each in fluid communication with a different hydrolysis unit wherein the hydrolysis units are arranged in parallel and each feed a different bioreactor, and hydrolyzed feedstock is fed continuously to each bioreactor, with effluent continuously withdrawn from each bioreactor. In one embodiment, the system contains multiple bioreactors arranged in series, the first bioreactor in the series is in fluid communication with the hydrolysis unit, and hydrolyzed feedstock is fed continuously to the first bioreactor in the series, with effluent continuously withdrawn from each bioreactor and fed to each subsequent downstream bioreactor in the series, and effluent from the last bioreactor in the series continuously withdrawn from the system.

In some embodiments, the system for bioproduct, e.g., biofuel, production operates with the bioreactor(s) under pressure to compress gas in the bioreactor(s), including $CO_2$ generated by the microorganisms during fermentation. $CO_2$ generated during fermentation effectively reduces the liquid volume in the bioreactor, thus decreasing the residence time of the liquid hydrolyzed feedstock. Compression of gas in the bioreactor has the effect of increasing residence time of the hydrolyzed feedstock in the reactor, which improves utilization of the sugar molecules in the feedstock and conversion of the sugar to bioproduct, e.g., biofuel, for example, butanol. Operation under pressure impacts the solubility of gaseous species ($CO_2$ and $H_2$) and may affect fermentation parameters of interest, such as product yield, selectivity and/or productivity, for example, by affecting the redox potential, pH, or other parameters. Hydrolyzed feedstock may be added to the bioreactor continuously under pressure. The pressure in the bioreactor may be about 1 to about 30 atm, or about or at least about 1, 2, 3, 5, 10, 15, 20, 25, or 30 atm. Alternatively, $CO_2$ may be removed periodically, intermittently, or continuously from the bioreactor, for example, at points along the length of the bioreactor. Fermentation gases may also be removed between reactor stages (e.g., primary and/or secondary and/or further reactors in series). In a further embodiment, residence time of the hydrolyzed feedstock may be increased by using a solid support with hydroscopic properties to increase liquid holdup, and thus increase residence time. Both productivity (g bioproduct, e.g., biofuel, per hour per liter) and titer (g bioproduct, e.g., biofuel, per liter) may be increased as a result of the increased residence time of hydrolyzed feedstock in the bioreactor.

In some embodiments, the system may also include downstream continuous concentration and/or purification modules for recovery of the bioproduct, e.g., biofuel, product, for processing of continuously withdrawn effluent to produce a bioproduct. In some embodiments, the system includes a module for concentration of the bioproduct-containing effluent, in fluid communication with and downstream from the bioreactor(s). In one embodiment, concentration includes distillation. In one embodiment, distillation comprises MVR. In a further embodiment, the system includes a module for purification of bioproduct, e.g., biofuel, from the concentrated bioproduct-containing effluent, in fluid communication with and downstream from the concentration module. In one embodiment, purification includes distillation.

In some embodiments, the system may also include a conditioning unit for removal of inhibitors of microbial growth or bioproduct, e.g., biofuel, production, as described herein. The conditioning unit may operate continuously downstream from and in fluid communication with the feedstock hydrolysis process, and upstream and in fluid communication with the bioreactor(s), and conditioned hydrolyzed feedstock may be continuously fed to the bioreactor for the duration of fermentation. In one embodiment, the conditioning unit includes ion exchange resin, and the inhibitors are retained on the resin. In another embodiment, the conditioning unit includes a precipitation unit and the inhibitors are removed with the separated precipitate. In a further embodiment, inhibitory compounds are separated from the hydrolysate in a steam stripping operation.

In some embodiments, the system may also include units for deconstruction of the feedstock and/or removal of extractives from the feedstock, as described herein. Deconstruction and/or removal of extractives may operate continuously upstream and in fluid communication with the hydrolysis unit, or may occur prior to or periodically throughout the continuous process.

Energy Integration

The bioproduct, e.g., biofuel, production processes and systems described herein may include one or more energy integration systems, for capturing and recycling energy generated in one part of the bioproduct production process and using the captured energy to drive another part of the process. The energy integration schemes described herein include integration between process areas and effect a global change to the overall plant energy use.

Methods of energy exchange are well known in the art, for example, feed bottoms exchangers for distillation towers. Heat exchange methods may also be used at various points in the system.

In one embodiment in which a two stage nitric acid hydrolysis process is used for hydrolysis of a lignocellulosic feedstock, as described supra, flash steam generated in the first stage and/or second stage hydrolysis process(es) may be captured and used for deconstruction of the feedstock prior to hydrolysis.

In one embodiment in which a two stage nitric acid hydrolysis process is used for hydrolysis of a lignocellulosic feedstock, as described supra, flash steam generated in the second stage hydrolysis process may be recompressed and the recompressed steam used to provide energy for the first stage hydrolysis. In one embodiment, the flash stream is not compressed.

In one embodiment in which a two stage nitric acid hydrolysis process is used for hydrolysis of a lignocellulosic feedstock, as described supra, flash steam generated as part of the hydrolysis process may be used to provide lie steam for steam stripping operations, to preheat streams, remove inhibitory compounds from hydrolysate, and/or to facilitate product separation and recovery operations.

In one embodiment in which a two stage nitric acid hydrolysis process is initially used for hydrolysis of a lignocellulosic feedstock, as described supra, flash steam is generated in the second stage hydrolysis process may be used to provide energy for a third stage hydrolysis, with the temperature of the third stage lower than the temperature of the second stage, and with the temperature and/or residence time of the second stage reduced in comparison to a process without the third stage, thus permitting hydrolysis of remaining oligomeric sugar molecules with less degradation than hydrolysis performed at a higher temperature than the temperature of the third stage. This method could also be extended to four or more stages of hydrolysis with decreasing temperature in a cascade effect. In one embodiment with three hydrolysis stages, flash steam generated in the second stage is used to provide energy for the first stage, and flash steam generated in the first stage is used to provide energy for the third stage.

In one embodiment in which a two stage nitric acid hydrolysis process is used for hydrolysis of a lignocellulosic feedstock, as described supra, flash steam generated in the first and/or second stage hydrolysis process may be recompressed and the recompressed steam is used to provide energy for a distillation process for purification of bioproduct, e.g., biofuel, from bioproduct containing effluent from continuous microbial fermentation, as described supra.

In one embodiment in which a two stage nitric acid hydrolysis process is used for hydrolysis of a lignocellulosic feedstock, as described supra, flash steam generated in the first and/or second stage hydrolysis process may be used to provided energy for preheating a feed stream to a distillation process for purification of bioproduct, e.g., biofuel, from bioproduct containing effluent from continuous microbial fermentation, as described supra. The flash steam may optionally be recompressed prior to use for preheating the feed stream.

In one embodiment in which a two stage nitric acid hydrolysis process is used for hydrolysis of a lignocellulosic feedstock, as described supra, flash steam generated in the first and/or second stage hydrolysis process may be recompressed and the recompressed steam is used to provide energy for drying and/or dehydration of products separated in a distillation process as described supra. For example, the recompressed steam may be used to provide energy for drying and/or dehydration of biomass from the fermentation process.

In some embodiments, lignin is recovered in the solids-containing residue remaining after hydrolysis of lignocellulosic feedstock, for example, in the solids-containing residue remaining after the second stage of a two stage nitric acid hydrolysis process, as described supra. The lignin-containing residue may be used as an energy source for the bioproduct, e.g., biofuel, production process, as a fuel source for electricity generation, as a feedstock for chemical production, for example, production of phenolic resins, and/or as a soil enhancer.

Integrated Bioproduct Production Plant

Figure 2:
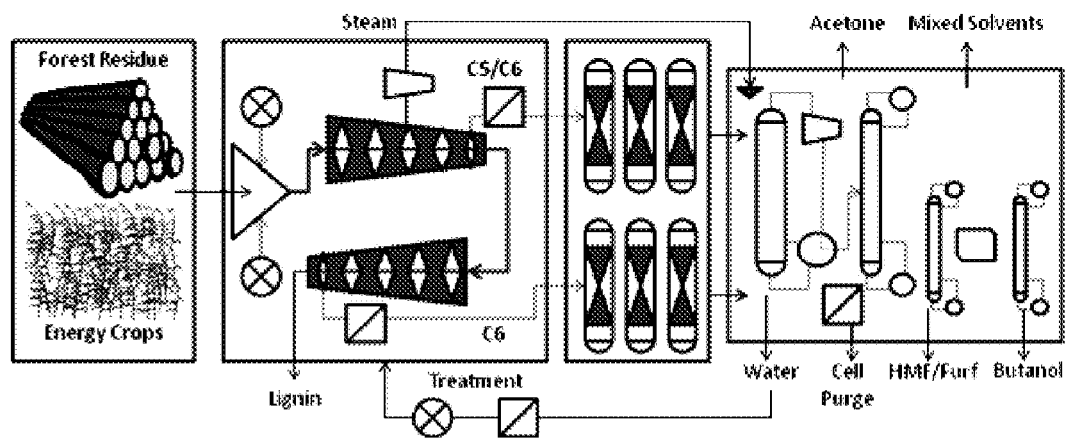
FIG. 2 shows a schematic diagram of an embodiment of an integrated biofuel plant in which biobutanol production processes and systems described herein
Figure 3:
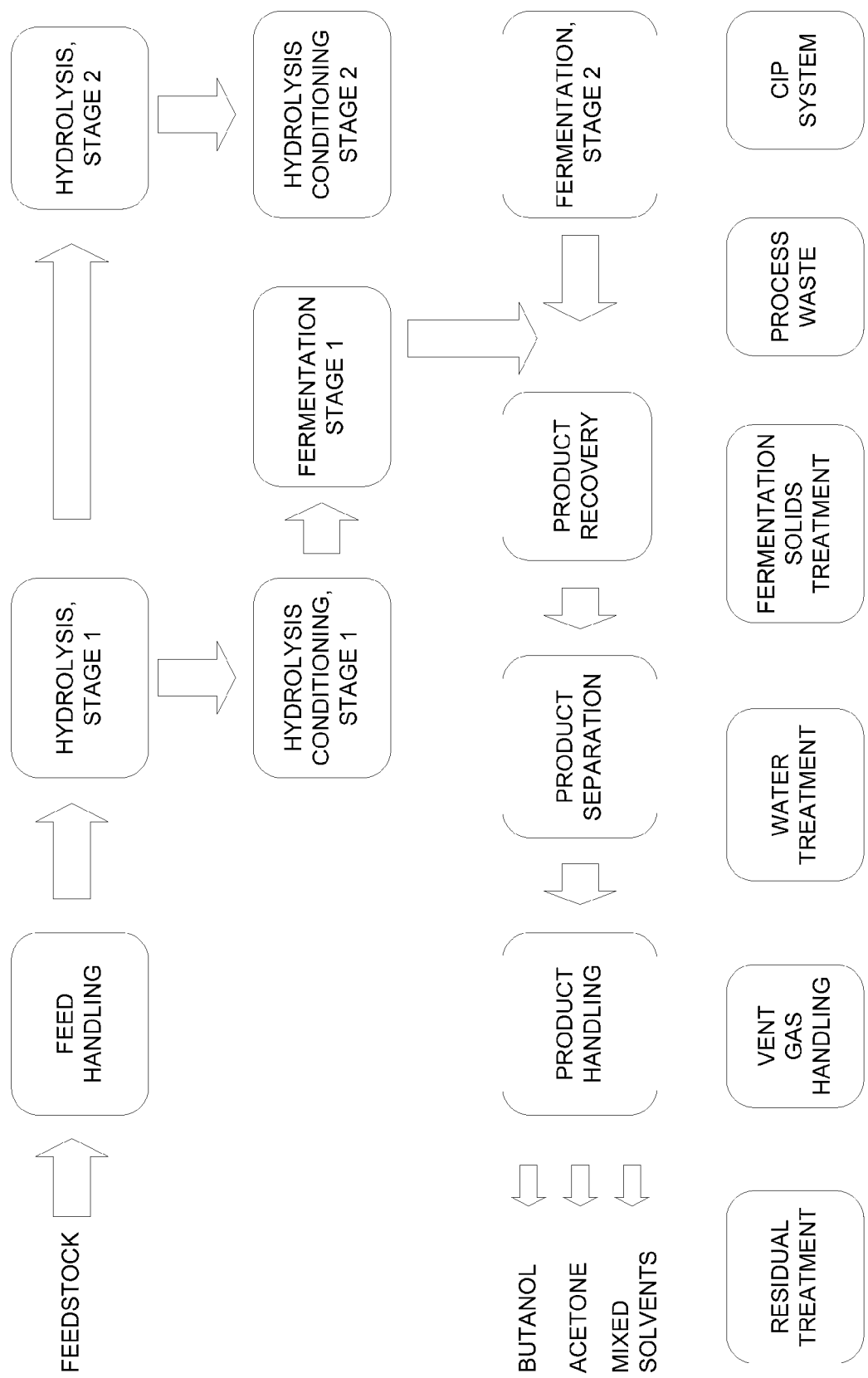
FIG. 3 shows a process flow diagram for an embodiment of an integrated biofuel plant in which biofuel production processes and systems described herein may be utilized.

An integrated plant is provided that can produce a bioproduct, such as a biofuel. For example, biobutanol may be produced from a wide variety of feedstocks in a capital and energy efficient process, with low greenhouse gas (GHG) emissions and the potential to make a significant contribution to reducing oil imports, achieving advanced biofuels targets, developing a domestic bioindustry, creating jobs, and promoting economic development. Embodiments of such an integrated biofuel, e.g., biobutanol, plant, utilizing processes and systems for continuous biofuel production described herein, are schematically depicted in FIGS. 1-3.

A biorefinery as described herein may provide an economic benefit, the production of bioproducts with a reduced carbon intensity (emission, footprint) as compared to petrochemically derived counterparts. The primary driver for this reduction in carbon intensity is the relatively rapid utilization of carbon in the feedstock as compared to petroleum based chemical feedstocks. As an example of the reduction of carbon intensity, n-butanol is the bioproduct and the bioproduct is used to displace gasoline use. The carbon intensity of gasoline depends on the feedstock source of production, production energy, product transportation and product use and is approximately 0.095 kg $CO_2e$/MJ of gasoline. Similarly, butanol produced in such a biorefinery as described herein has a carbon intensity of approximately 0.010 kg $CO_2e$/MJ of butanol. The carbon intensity of the biorefinery also depends on the feedstock source of production, production energy, product transportation and product use. In the case where reduction in intensity is largely attributed to a feedstock, $CO_2$ uptake credit is generated as the biomass is produced prior to harvest.

The avoidance of carbon intensity has been valued by commodity agencies such as the Chicago Board of Trade. A price target is subject to market demand and is priced accordingly. As an example, at \$10/MT $CO_2e$, or \$0.01/kg $CO_2e$ avoided, a production facility that generated 1e9 MJ of butanol which was used to displace gasoline would result in an avoidance of 8.5e7 kg $CO_2e$, with a value of \$0.85MM.

An integrated bioproduct, e.g., biofuel, plant can be built to a variety of capacities. In some instances, a pilot plant has the capacity to process one to five dry tonne(s) of feedstock per day. The feedstock for the plant can be cellulosic biomass, for example, lignocellulosic biomass such as woody biomass, which may be sourced locally and is available in many regions of the country. Pretreatment of the biomass can be accomplished an acid hydrolysis process, such as a two stage dilute acid process to extract soluble sugars from the hemicellulose and cellulose.

In some embodiments, these sugars can be fermented to biofuel, e.g., biobutanol, using *Clostridium* strains. In some embodiments, a *Clostridium* strain can produce n-butanol from both monomeric and multimeric forms of both C5 and C6 sugars. Fermentation can occur in an immobilized bed bioreactor running a continuous process, which can deliver up to or more than ten times the productivity of a comparably-sized batch fermentor. Product recovery and distillation (for example, high-efficiency mechanical vapor compression) techniques and advanced integration of heat streams from adjacent process streams and areas to produce high purity biofuel, e.g., biobutanol with low overall energy use.

The integrated bioproduct, e.g., biofuel, production plant can be a fully integrated standalone facility. In addition to the operations contained in the integrated plant, the facilities can include feedstock storage and handling, product storage and loadout, and on-site utilities. The integrated plant can have one or more streams to recover heat and/or materials. For example, recycle streams can be used to improve efficiency of separation processes or bioconversion processes. Other streams can be used for heat exchange from one process unit to another, or within a process unit.

In some embodiments, an integrated bioproduct, e.g., biofuel, production plant may be co-located to utilize a waste stream, such as hemicellulose from a pulp mill, to achieve economic advantages gained through co-location and co-utilization of utilities, feed handling, feed logistics, off-take, chemical production, etc.

In various embodiments, the bioproduct, e.g., biofuel, production plant can utilize one or more hydrolysis stages for feedstock preparation, one or more conditioning processes to prepare hydrolysates for bioconversion, one or more fermentors for growing one or more strains that are capable of producing a bioproduct such as butanol and optionally other products of interest, and one or more separation processes to isolate the desired products. The various processing units can be designed and coordinated such that the complete operation of the plant is in a continuous manner. Accumulation of products or feed materials between process operations can be avoided. Residence time of processed materials prior to being fed to a downstream operation can be reduced to avoid undesirable degradation or modification of materials. Rates of processing for upstream processing units can be controlled based on performance of downstream processing units and vice-versa. For example, if a reduction in bioconversion by a microbial strain is observed, the rate of hydrolysis of a feedstock can be reduced such that accumulation of products is avoided.

In some embodiments, commercial plant output can include butanol as the primary product, acetone, a mixed solvent containing acetone, ethanol and sugar degradation products, and lignin. Per tonne of a particular feedstock, the plant can produce about or at least about 53.5 gallons of butanol, 4.1 gallons of acetone, 0.039 tonnes of mixed solvents and 0.419 tonnes of a lignin. The butanol and acetone can be sold into the fuels and chemicals markets, respectively. The mixed solvents (which may include acetone, ethanol, butanol, degradation products, woody biomass compounds, fermentation byproducts, fermentation generated biomass, and/or water) and most of the lignin can be used in an onsite co-generation unit to generate all of the steam and electricity required to operate the plant, and the remaining lignin can be dried to remove water, for example to about 15% moisture content, and sold as boiler fuel. The removal of water from the lignin is important to increase the value of the lignin stream in that the energy content per unit weight is increased by removing the water and the commensurate latent heat of the water. Drying techniques are well known in the art.

An integrated biobutanol plant can produce butanol at a variety of scales. Butanol can be produced at pilot scale at about 13,000 gallons per year, at demonstration scale at about 2 to 2.5 million gallons per year (consuming about 150 tonnes of feedstock per day) and at commercial scale at about 50 million gallons per year.

For every gallon of biobutanol produced, the plant can produce about or at least about 0.08 gallons of acetone and about or at least about 2.7 kg of lignin. The estimated feedstock consumption of the commercial plant can be about 2,700 dry tonnes per day (112,500 dry kg/hr), based on a yield of 53 gallons of biobutanol per tonne of feedstock.

The amount of butanol that can be produced per tonne of feedstock can be about, up to about or at least about 10, 20, 30, 40, 50, 60, 70, or 80 gallons. A petroleum analysis indicates a displacement of 2.7 million equivalent barrels of oil annually for a 50 million gallon per year facility. The plant can be located in numerous areas in the country where this amount of forest waste, with sufficient surplus to avoid market pressure, is available locally. The plant can include all of the unit operations of the feedstock bioconversion, plus feedstock handling and product distribution and load out operations. In addition, the commercial facility can have its own biomass-fired power plant on site, which can use lignin in the solids-containing residue remaining after feedstock hydrolysis, the small amount of ethanol and a portion of the acetone produced in the fermentation process recovered in the distillation system, plus furfural and HMF extracted from the feedstock to provide all of the steam and electricity required by the process, with excess lignin sold to offsite power facilities. The facility may require about or at least about 20,000, 30,000, 40,000, 50,000, 60,000, 70,000, 80,000, 90,000, 100,000, 150,000, 200,000, 250,000, 300,000, 350,000, 400,000, 450,000, or 500,000 BTUs of thermal energy per gallon of butanol, about or at least about 1, 1.5, 2, 2.5, 3, 3.5, 4, 5, or 10 kilowatt hours per gallon and about or at least about 1, 2, 3, 4, 5, 6, 7, 8, 10, 20, or 30 gallons of water per gallon of biobutanol produced, depending on the process configuration. These numbers can be reduced, including further reductions in the estimated water usage. For example, air coolers can be used whenever possible to reduce cooling tower evaporative losses and minimize the fresh water footprint.

The equipment for an integrated bioproduct production plant as described herein can be purchased from commercial manufacturers of industrial process equipment. The equipment materials can be selected based on corrosion and erosion resistance. In particular, the equipment materials can be evaluated for the hydrolysis processes, which may be performed under acidic conditions at elevated temperatures and pressures. In some embodiments, the equipment design does not require the use of exotic materials or specialized equipment available from a single or limited number of vendors. Notably, in embodiments in which a nitric acid hydrolysis process is used, pretreatment vessels can be made of stainless steel (e.g., Duplex 2205) rather than the expensive alloys often required in other processes. Spare parts can be kept at the plant to ensure continuous processing without a lengthy interruption or turnaround.

Operating parameters and behavior of fermentors including inoculation, longevity of growth, pH control, and sterilization can be determined at lab bench or pilot scale prior to implementation at commercial scale. In some embodiments, variability can be addressed by segregating C5 and C6 fermentor volumes into multiple vessels, for example, two, three, or more vessels per unit operation. This design concept can allow maximum flexibility as the vessels can be manifolded to allow isolation or recirculation of media by individual reactor. This operational flexibility can allow run times to be extended by rotating the position of the individual fermentors within the train while optimizing microbial, e.g., *Clostridium* performance. Individual reactors can be isolated, sterilized, and inoculated while the remaining vessels are online. The bioreactor design and operational configurations, which can include multiple reactors in series, can be chosen to maximize the production of the bioproduct of interest, for example, a biofuel, e.g., biobutanol, thereby reducing capital costs and improving operational logistics.

An integrated bioproduct, for example, biofuel, e.g., biobutanol production plant can include a high degree of instrumentation and control using a supervisory control and data acquisition (SCADA) system and/or distributed control system (DCS). These systems collect real time data on a wide range of performance parameters and the data may be used to optimize process control parameters, setpoints, and conditions. For example, a custom designed SCADA system can collect multiple parameters including fermentor offgas concentration data measured by an online MS, which can be an effective real-time indicator of metabolism and optionally solvent production in embodiments in which a solvent such as biobutanol is produced.

A variety of products can be produced using the systems and methods described herein. These products include butanol, acetone, ethanol, green gasoline, and mixed alcohols. Other products include lignin, cellulose, hemicellulose, sugars, acids, or any other product described herein. Natural products such as xylitol, vitamin B12, and other compounds may be separated in the production process to improve plant economics. Organic products that can be used as a fuel can be blended with each other, or blended with additional materials. For example, butanol can be blended with gasoline or any other combustible fuel.

Butanol produced by the systems and methods described herein, including fermentation and separation, can be at a purity of about or at least about 30, 40, 50, 60, 70, 75, 80, 85, 90, 95, 97, 99, 99.5, 99.8, 99.9, or 99.99%. Acetone produced by the systems and methods described herein, including fermentation and separation, can be at a purity of about or at least about 30, 40, 50, 60, 70, 75, 80, 85, 90, 95, 97, 99, 99.5, 99.8, 99.9, or 99.99%. Ethanol produced by the systems and methods described herein, including fermentation and separation, can be at a purity of about, up to about, or greater than about 30, 40, 50, 60, 70, 75, 80, 85, 90, 95, 97, 99, 99.5, 99.8, 99.9, or 99.99%.

Butanol produced by the systems and methods described herein, after fermentation or separation, can be a blend of butanol, acetone, and ethanol. In one embodiment, the blend can be 70 parts butanol to 30 parts acetone. This can be determined on an organic solvent basis, excluding water. In other embodiments, the blend can include butanol:acetone:ethanol at a ratio of 33:12:1, 58:12:1, or 90:9:1.

Butanol production for a commercial plant can be about 50 million gallons of butanol per year. In some embodiments, a plant may be designed to produce less than about 1 million gallons per year of butanol, or about 1 to about 2, about 2 to about 5, about 5 to about 10, about 10 to about 50, about 20 to about 50, about 30 to about 50, about 40 to about 50, or about 45 to about 50 million gallons per year of butanol.

Lignin separated in an integrated bioproduct production plant as described herein, in the form of lignin-containing residue remaining after hydrolysis of lignocellulosic feedstock, can be stored or processed by a lignin handling and storage unit. For example, this unit operation can process the lignin-containing residual material from the second stage acid hydrolysis of lignocellulosic feedstock, as described supra, including unconverted cellulose and hemicellulose material. The lignin product stream can be dried, for example, using hydrolysis flash steam. At about 35 wt % moisture, the material will have a usable heating value. The material can be further dried to improve the product value, for example, to about 15 wt % moisture, subsequently pelletized, and stored for sale as fuel, for example, for electricity generation or burned as dried to provide thermal energy. Dried, pelletized lignin may also be used to generate high pressure steam to provide energy for use in first and second stage nitric acid hydrolysis processes for hydrolysis of lignocellulosic feedstock, as described supra.

In some embodiments, biomass can be removed from the fermentation broth during the product separation and distillation phase. The recovered material can be dried and burned for process heat or can be digested to generate methane and remove the cellular mass without release to the environment.

The effluent streams from a nitric acid pretreatment process can contain significant levels of nitrogen. Ammonium nitrate created during neutralization of nitric acid can be converted to nitrogen and water. Ammonium nitrate containing solutions may also be used as feedstocks for subsequent microbial water treatment ponds.

The following examples are intended to illustrate, but not limit, the invention.

EXAMPLES

Example 1

Butanol Production in Continuous Packed Bed Bioreactors

*Clostridium* strains were grown in 100 mL or 1 L continuous packed bed bioreactors for lengths of time as shown in Table 1. Co-7449 is a strain of *Clostridium saccharobutylicum* that is very stable in continuous culture, possesses increased acid recycle capabilities in comparison to wild-type, and utilizes mixed sugars in a softwood hydrolysate well. Co-5673, an environmental isolate of *Clostridium*, is also stable in continuous culture, and possesses increased tolerance to acids. The microbial cells were grown anaerobically on bone char, using a sugar substrate. Butanol titer, yield, and performance are included in Table 1, calculated using the best sustained performance (100 hours or more) for each fermentation. Substrate concentrations in the table are expressed as weight of substrate per volume of liquid. Data from representative fermentation runs is presented in FIGS. 6-12.

TABLE 1

| Run No. | Bioreactor volume | Total EFT* (h) | Strain | Substrate | Butanol (g/L) | $Y_{BuOH}$ (% theor) | $P_{BuOH}$ (g/L/h) |
|---|---|---|---|---|---|---|---|
| 2008065 | 100 mL | 1024 | Co-7449 | 4% Glucose | 4.2 | 49 | 3.1 |
| 2008137 | 1000 mL | 831 | Co-7449 | 4% Sucrose | 7.5 | 61 | 5.1 |
| 2009012 | 1000 mL | 478 | Co-5673 | 5% Sucrose | 8.4 | 63 | 6.1 |
| 2009021 | 1000 mL | 473 | Co-7449 | 4% Xylose | 5.4 | 63 | 4.1 |
| 2009023 | 1000 mL | 568 | Co-5673 | 4% Xylose | 4.0 | 63 | 3.0 |
| 2009047 | 1000 mL | 1250 | Co-7449 | 4% Xylose | 4.7 | 88 | 3.4 |
| 2009054 | 1000 mL | 352 | Co-7449 | 4% Mixed sugar simulated hydrolysate** | 5.6 | 61 | 4.0 |
| 2009057 | 1000 mL | 628 | Co-5673 | 4% Mixed sugar simulated hydrolysate | 5.9 | 61 | 4.3 |
| 2009060 | 1000 mL | 640 | Co-7449 | 4% Mixed sugar simulated hydrolysate | 5.0 | 56 | 3.6 |

*EFT = elapsed fermentation time
**Mixed sugar simulated hydrolysate = 5 parts mannose (31%), 4 parts xylose (27%), 3 parts glucose (16.5%), 2 parts galactose (12%), 2 parts arabinose (11%)

Example 2

Continuous Biobutanol Production and Recovery

A continuous biobutanol production and recovery process is described below, with all of the described component processes (e.g., feedstock hydrolysis, fermentation, recovery of product) operating simultaneously and continuously in an integrated biobutanol production plant.

Hydrolysis of Lignocellulosic Feedstock

C5 and C6 sugars are produced from hemicelluloses and cellulose components of wood chips in a two-stage dilute nitric acid hydrolysis process. The two-stage approach includes two reaction stages at two different temperatures, minimizes thermal degradation products and maximizes sugar recovery from both the hemicelluloses and cellulose components of the feedstock.

First Stage Hydrolysis

Wood chips are mixed with nitric acid and water and pressured into the first stage hydrolysis reactor using a progressive reducing screw auger. The first stage hydrolysis reactor operates at or around 175° C. using 115 psig steam and is sized to provide a residence time of 5 to 9 minutes. A discharge auger and blow valve deliver reactor effluent to a flash tank where low pressure steam is recovered for re-use in the process. The steam may be augmented by recovered steam from other operations.

C5 hydrolysate is separated from the unconverted biomass in a screw press, stripped with nitrogen for oxygen removal, and pumped to the C5 fermentation section of the biobutanol production plant. (Despite containing both C5 and C6 sugars, the stage 1 hydrolysate liquor contains nearly all of the C5 sugars, and as a matter of nomenclature has been termed "C5 hdyrolysate" herein.) The C5 hydrolysate is brought to about pH 3.5 with ammonium hydroxide and passed through an anion exchange resin bed upstream of fermentation. The screw press may include a solids wash step to maximize recovery of fermentable sugars.

Second Stage Hydrolysis

Residual uncoverted biomass from the first stage hydrolysis is mixed with nitric acid and water and pressured into the second stage hydrolysis reactor using a progressive reducing screw auger. The second stage hydrolysis utilizes a higher temperature than the first stage hydrolysis to break down the recalcitrant cellulose component.

The second stage reactor operates by injecting saturated live steam at 215° C. (with the relationship between temperature and pressure well known by those of skill in the art) and is sized to provide a residence time of 3-8 minutes. A discharge auger is used to deliver reactor effluent to a flash tank where additional low pressure steam is recovered.

The C6 hydrolysate is separated from solids containing unconverted cellulose and lignin in a screw press, stripped with nitrogen for oxygen removal, evaporated to remove water and some acetic acid, brought to about pH 3.5 with ammonium hydroxide, passed through an anion exchange resin bed (e.g., Duolite A7), and pumped to the C6 fermentation section of the biobutanol production plant. The screw press separation also contains a solids wash step to maximize recovery of fermentable sugars. Residual cellulose/lignin is either neutralized and disposed of or steam dried and utilized as boiler fuel for process steam and/or electricity generation.

C5 Fermentation

Neutralized C5 hydrolysate from the first stage hydrolysis unit operation is cooled to fermentation temperature, treated to remove fermentation inhibitors via anion exchange as discussed above, mixed with nutrients and charged to a bioreactor or the first bioreactor in a series of bioreactors. The C5 hydrolysate is fermented into biobutanol in the bioreactor using an immobilized *Clostridium* strain that has been selected to maximize titer, yield, and butanol selectivity for C5 hydrolysate.

The fermentation process also produces fermentation off gas, primarily carbon dioxide and hydrogen, which strips some solvent from the bioreactor. All three reactors operate near atmospheric pressure and include a heating/cooling jacket to maintain temperature at 32° C. Each of the reactors includes a controlled nitrogen purge into the vapor space that is sampled and vented to a vent gas treatment unit operation along with fermentation off gas.

The fermentation is carried out in a temperature controlled bioreactor under anaerobic conditions after supplementing the hydrolysate with nutrients for growth of the microorganism. After colonization of the bioreactor by the microorganism is achieved, a continuous feed of supplemented hydrolysate is started together with the simultaneous continuous withdrawal of the same amount of fermentation broth.

C6 Fermentation

Neutralized C6 hydrolysate from the second stage hydrolysis unit operation is cooled to fermentation temperature, treated to remove fermentation inhibitors via anion exchange as discussed above, mixed with nutrients and charged to a separate bioreactor or a series of bioreactors. The C6 fermentation unit operation is nearly identical to the C5 fermentation, discussed above, with the exception that the specific strain of *Clostridium* has been optimized to maximize titer, yield, and butanol selectivity for C6 hydrolysate. Alternatively, the same strain is used for both C5 and C6 fermentations in the same or separate bioreactors.

Product Concentration

Reactor effluent from the C5 and C6 fermentations is combined into a product recovery feed tank (or "harvest tank") where fermentation continues before being fed to the product recovery distillation column feed tank. Fermentor effluent is pumped from the feed tank to the distillation column where the dilute product stream is concentrated, for example from about 2.5 wt % total organics in the feed to about 50 wt % in the overhead liquid product or from about 1 wt % total organics to about 35 wt % in the overhead liquid product.

Overhead vapor from the distillation column is condensed in the overhead condensor. The recovered bottoms stream is passed through a heat exchanger, where energy is exchanged with the column feed stream to recover energy. The overhead stream is pumped to additional separation equipment for further purification of separate biofuel products, for example, acetone, butanol, and ethanol.

Product Distillation

Organic products are further purified from the concentrate by distillation. For example, high purity butanol and acetone may be produced with some ethanol removed via a side draw.

Example 3

Two-Stage Nitric Acid Hydrolysis of Lignocellulosic Feedstock in a Batch Reactor Nitric acid hydrolysis of a lignocellulosic feedstock was performed in two stages. The feedstock was beetle killed lodgepole pine obtained through Renewable Fiber in Fort Lupton, Co. Three quarter inch wood chips were milled to pass through a ¼ inch screen.

Approximately 1.3% nitric acid on a dry wood basis was reacted with feedstock in a 1.9 L reactor. The milled ¼ inch wood chips were loaded into a five gallon bucket and charged with water and nitric acid. The nitric acid concentration was approximately 1.3% on a dry wood basis and water was added to the bucket to completely submerge the wood chips. The total solids loading of the mixture was approximately 12 wt %, which corresponded to a liquids to solids ratio of approximately 7.5. The bucket was then sealed and placed on rollers where the contents of the bucket mixed for approximately 30 minutes. This step was done to impregnate the acid into the wood chips. The contents of the bucket were then transferred to the 1.9 L reactor, where the hydrolysis reaction took place. The reactor was sealed and charged with steam in order to reach a reaction temperature of 175° C. The time that the contents of the reactants were at this temperature was approximately 7 minutes, after which the contents of the reactor were flashed into a vessel at atmospheric pressure with additional cooling to rapidly cool the material and stop the hydrolysis reaction. The pH of the solution was approximately 2 during the reaction.

The reaction mixture was separated using a vacuum filtration unit into first stage hydrolysate and solid residue. The first stage hydrolysate was analyzed for conversion of cellulose and hemicellulose to soluble sugar molecules using high performance liquid chromatography (HPLC). The yields of soluble sugars based on cellulose and hemicellulose conversion were calculated by measuring sugars produced from complete hydrolysis of cellulose and hemicellulose concentrations in the starting material. Concentrated acid was used to hydrolyze both the cellulose and hemicellulose fractions of the wood. A theoretical maximum amount of sugar was then calculated based on the conversion of cellulose and hemicellulose to sugars. The yield from the dilute nitric acid hydrolysis was then compared to the theoretical maximum. In the first stage nitric acid hydrolysis reaction, 15.8% of hydrolyzed cellulose was detected as soluble sugars (glucose and oligomers) and 71.1% of hydrolyzed hemicellulose was detected as soluble sugars (xylose, mannose, and other oligomers) in the first stage hydrolysis reaction.

The solid residue from the first stage hydrolysis was rinsed with water to remove residual soluble sugars from the solids and to minimize the amount of sugar degradation in the second stage hydrolysis reaction. A nitric acid concentration of approximately 1.3 wt % on a dry solids basis was used to for hydrolysis of the solid residue. The residual solids were contacting with acid in a rolling bucket for approximately 30 minutes, as described above. The solids loading was approximately 14 wt %, or a ratio of about 6.5 liquid to solids. The acid impregnated residual material was then transferred to the 1.9 L reactor and injected with steam. The operating temperature of the second stage hydrolysis reaction was approximately 220° C. The contents in the reactor were heated to 220° C. for approximately 4 5 minutes and then flashed into a flash vessel to rapidly cool the reactants and stop the reaction. The pH of the solution was approximately 2 during the reaction.

The reaction mixture was separated into second stage hydrolysate and residual biomass using a vacuum filtration process. The second stage hydrolysate was analyzed for conversion of cellulose and hemicellulose to soluble sugar molecules, as described above. 23% of hydrolyzed cellulose was detected as soluble sugars (glucose and oligomers) and 0% of hydrolyzed hemicellulose was detected as soluble sugars (xylose, mannose, and other oligomers) in the second stage hydrolysis reaction.

Example 4

Conditioning of Hydrolyzed Feedstock with Ion Exchange Resin

First stage nitric acid hydrolysate from beetle killed lodgepole pine, prepared as described in Example 3, was conditioned to remove inhibitors of microbial growth by passage through an anion exchange column. Duolite A7 resin was used for conditioning of the first stage hydrolysate. The anion exchange resin was prepared using a 1 M solution of sodium hydroxide and then rinsed with distilled water.

The first stage hydrolysate, with a sugar concentration of approximately 50 g/L, was brought to room temperature and then to pH 5.5 using ammonium hydroxide, and was then applied to the prepared ion exchange column. Hydrolysate that passed through the column was used as a feed for microbial fermentation, and microbial growth was assessed, in comparison with hydrolysate that had not passed through the column. Fifteen milliliter fractions were eluted from the ion exchange column and were collected, 10 ml of which were then used as a fermentation feed to test for microbial growth. The remaining 5 ml in each fraction was analyzed for sugar concentration and presence of phenolic compounds.

Nutrients were added to the wood hydrolysate fractions and filtered with a 0.2 m filter to sterilize the media before inoculation. The filtered media was then inoculated with *Clostridium* strain Co-7449. The fermentations were inspected for growth over a 72 hour time frame. There was a clear point at which the bacteria stopped growing and that point represents a breakthrough of unidentified compounds in the ion exchange column.

Effluents from the fermentations with conditioned and unconditioned hydrolysate were analyzed by HPLC. Based on the HPLC analysis, an increase in an unidentified peak correlates well with the inhibited growth that was observed with the microorganism. Therefore, this peak may have played a role in the toxicity of the hydrolysate. Based on the residence time in the HPLC column, the peak is believed to contain a phenolic compound that is strongly related to toxicity. Duolite A7 is a phenolic based anion exchange resin, so it is possible that the postulated phenolic inhibitor compound was retained on the resin due to hydrophobic interaction with phenolic groups on the resin. It was also noted that the ion exchange process resulted in a loss of sugar in the hydrolysate. The amount of sugar loss was approximately less than 10% of the initial concentration.

Figure 5:
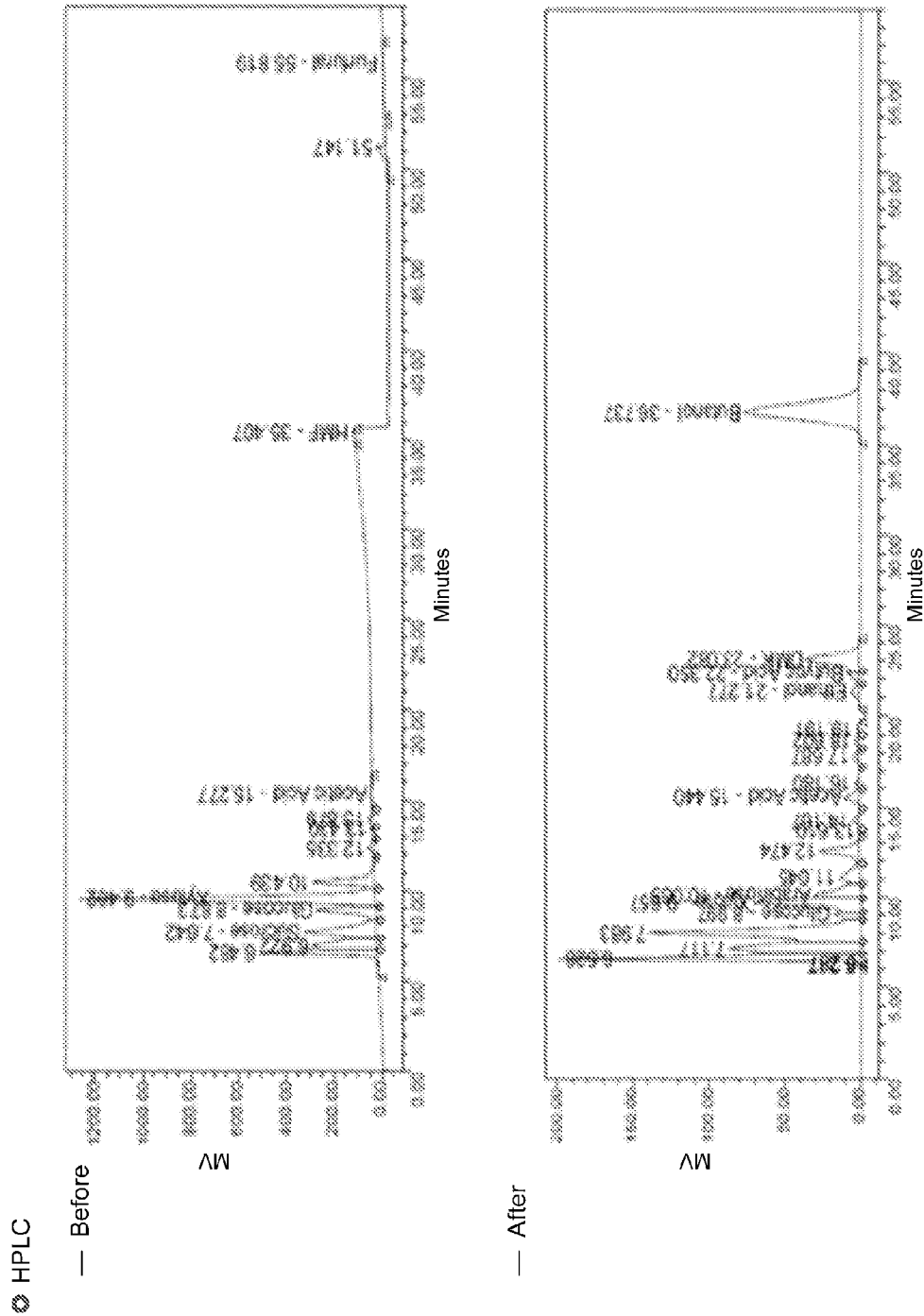
FIG. 5 shows the results of HPLC analysis of effluent from microbial fermentation on conditioned and unconditioned hydrolyzed feedstock, as described in Example 4.
Figure 6:
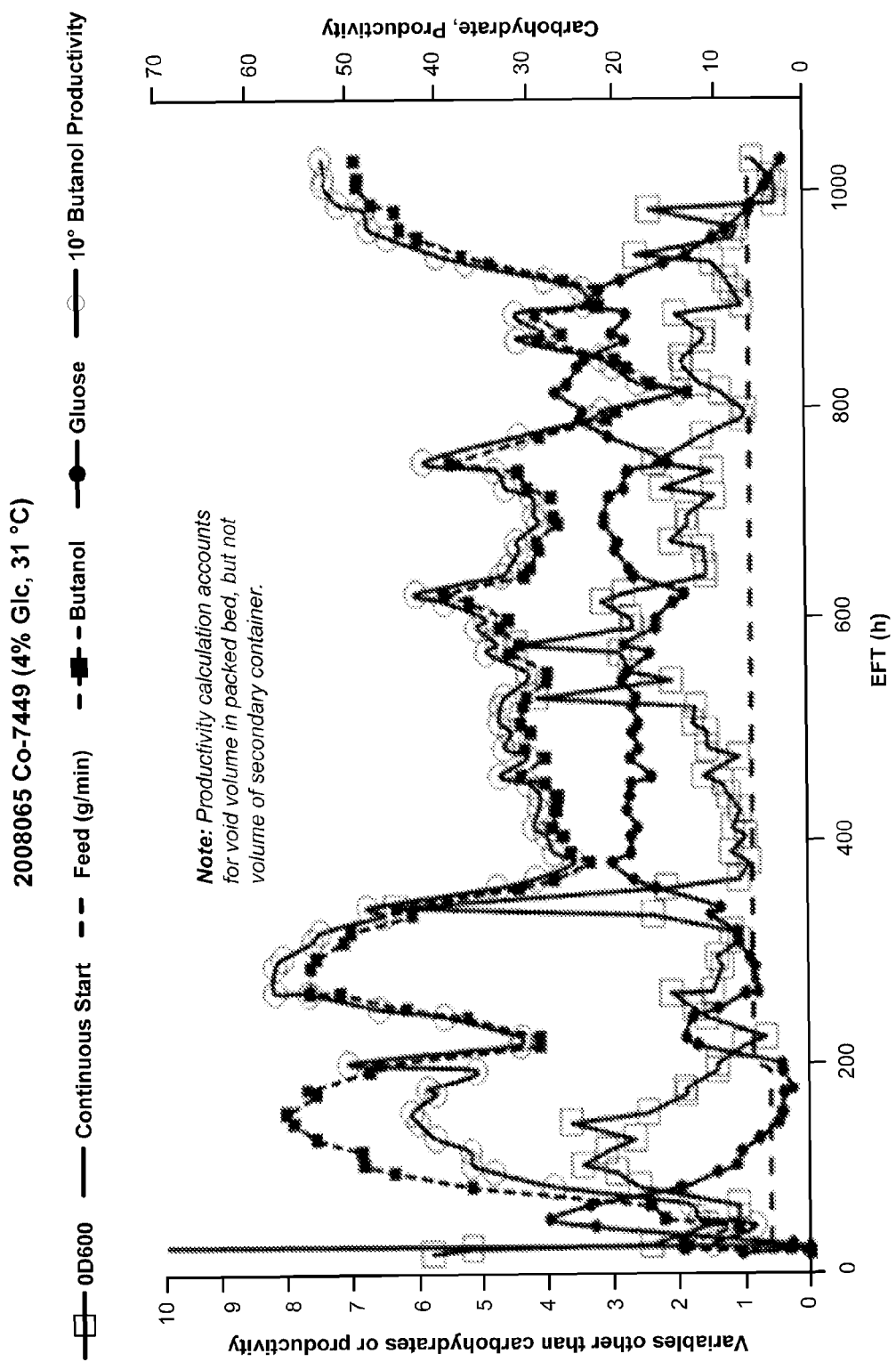
FIG. 6 shows the results of continuous culture of immobilized *Clostridium*, in run no. 2008065 (strain Co-7449 on 4% glucose) as described in Example 1.
Figure 7:
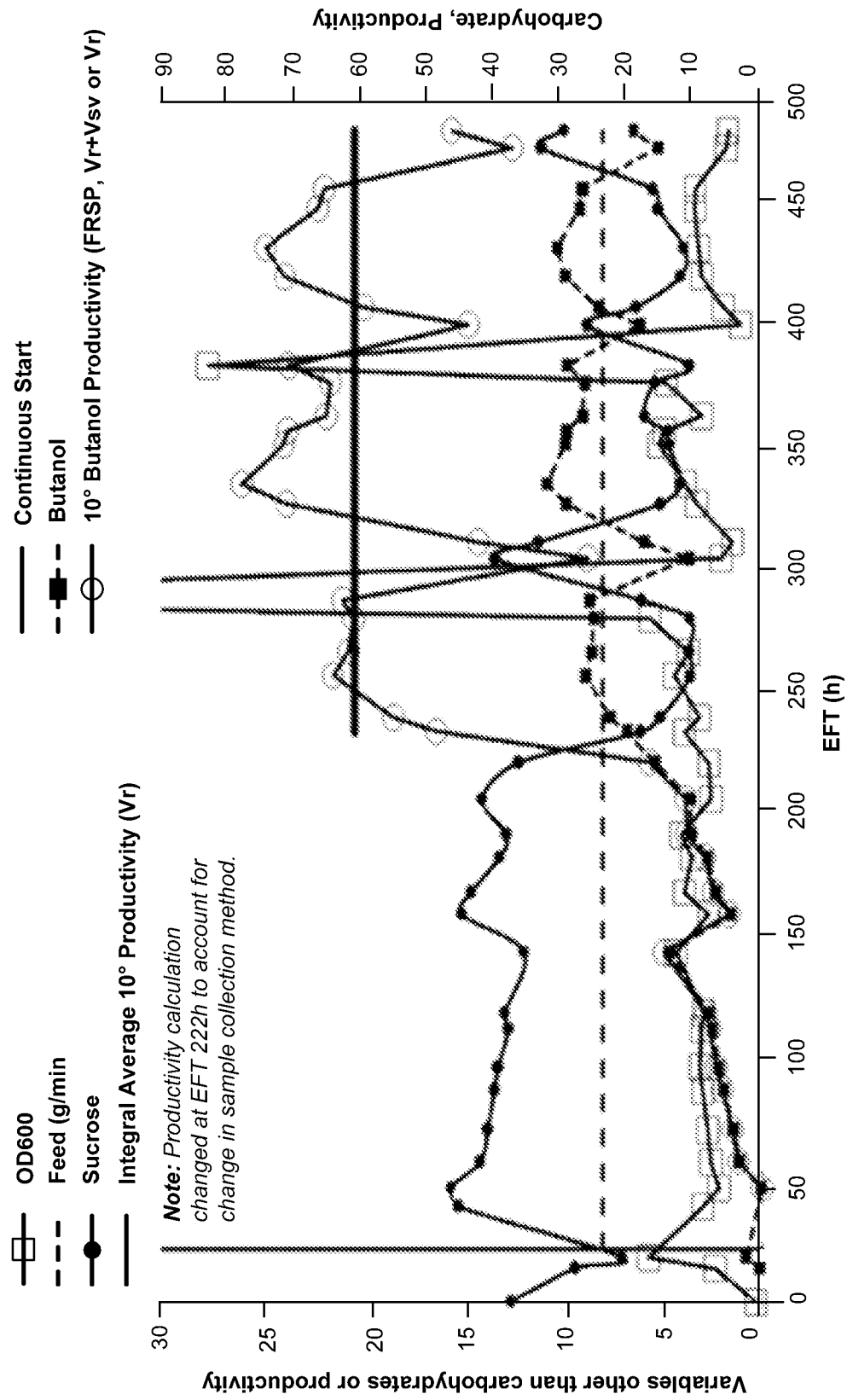
FIG. 7 shows the results of continuous culture of immobilized *Clostridium*, in run no. 2009012 (strain Co-5673 on 5% sucrose) as described in Example 1.
Figure 8:
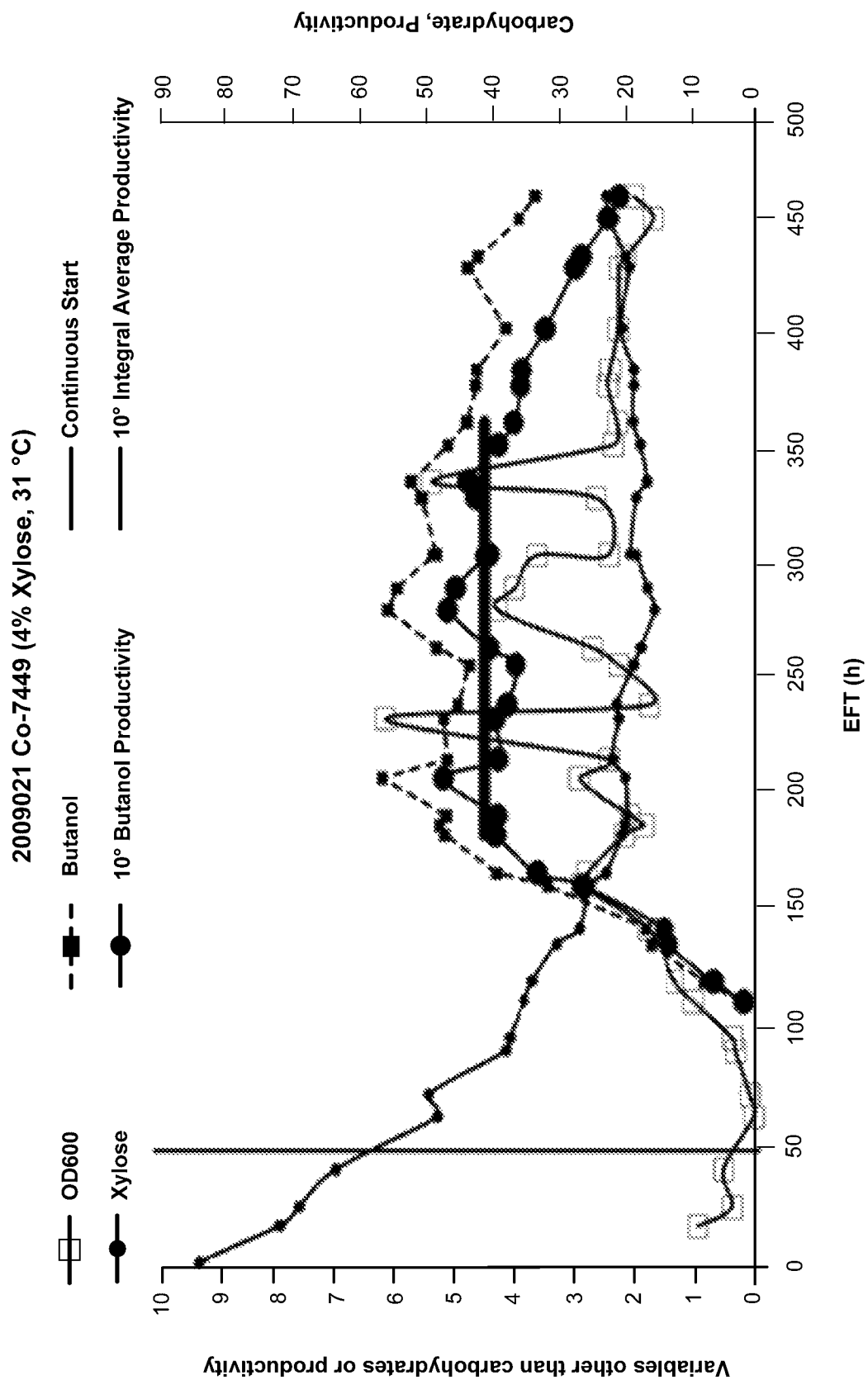
FIG. 8 shows the results of continuous culture of immobilized *Clostridium*, in run no. 2009021 (strain Co-7449 on 4% xylose) as described in Example 1.
Figure 9:
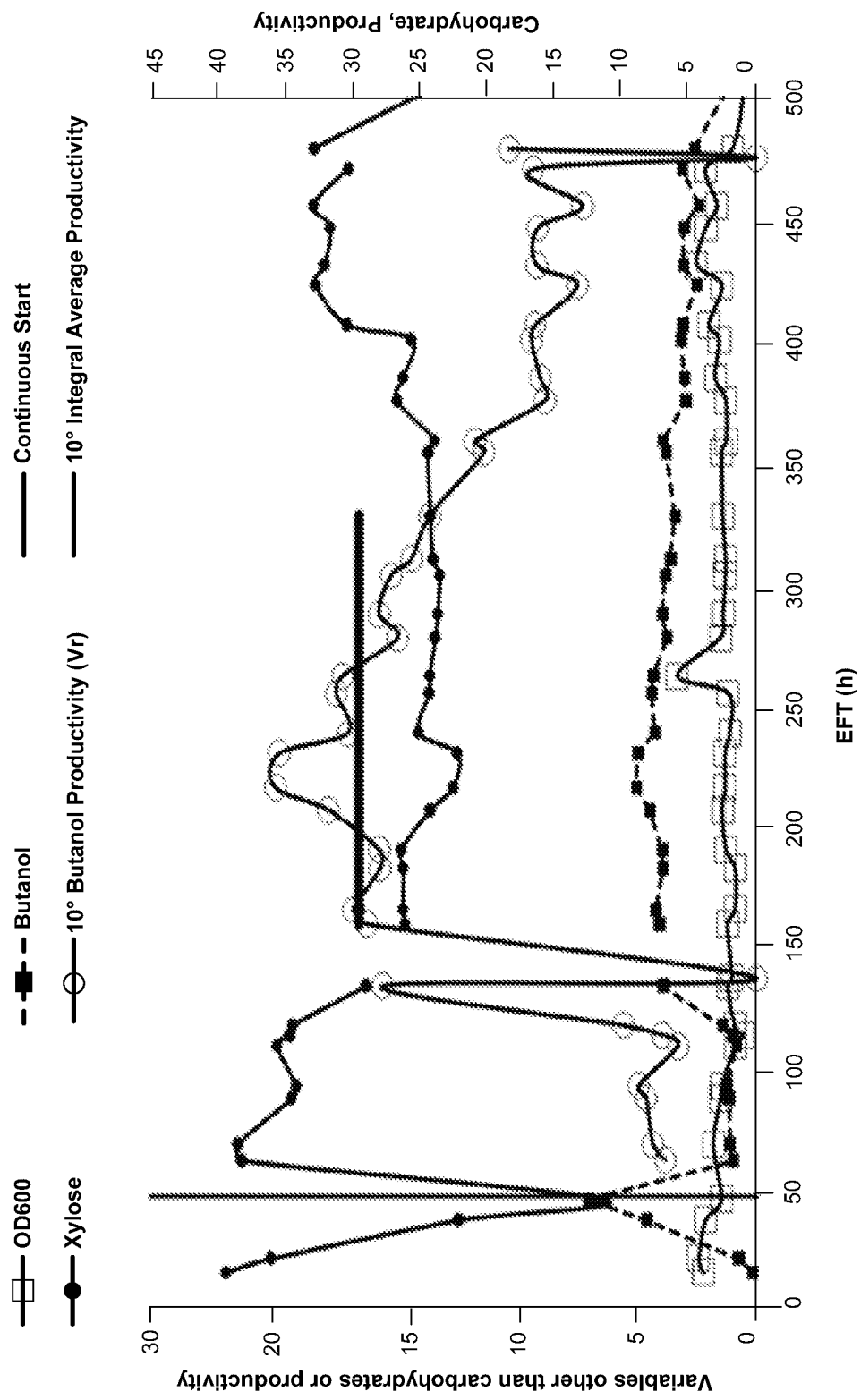
FIG. 9 shows the results of continuous culture of immobilized *Clostridium*, in run no. 2009023 (strain Co-5673 on 4% xylose) as described in Example 1.
Figure 10:
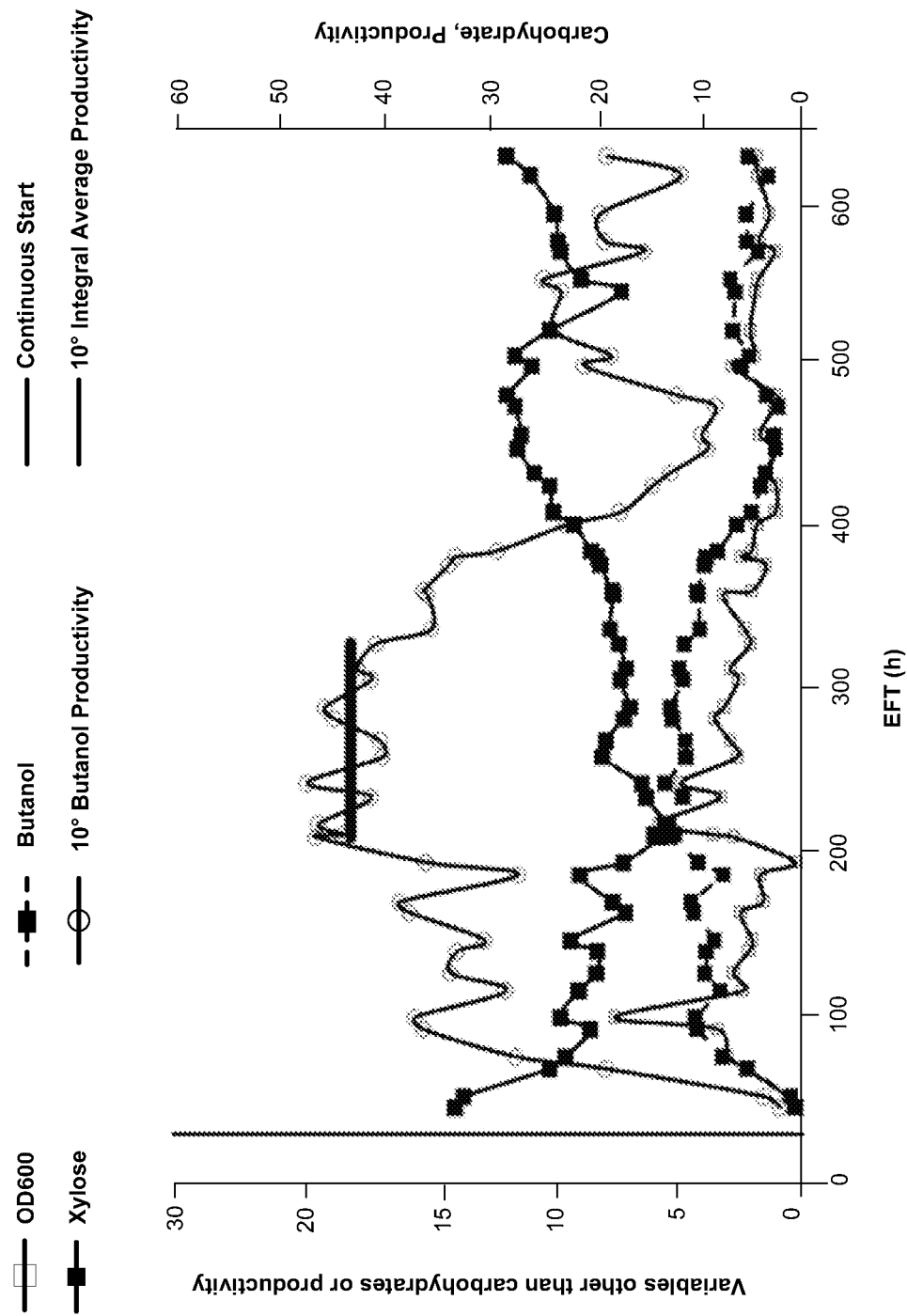
FIG. 10 shows the results of continuous culture of immobilized *Clostridium*, in run no. 2009057 (strain Co-5673 on 4% mixed sugar simulated hydrolysate) as described in Example 1.
Figure 11:
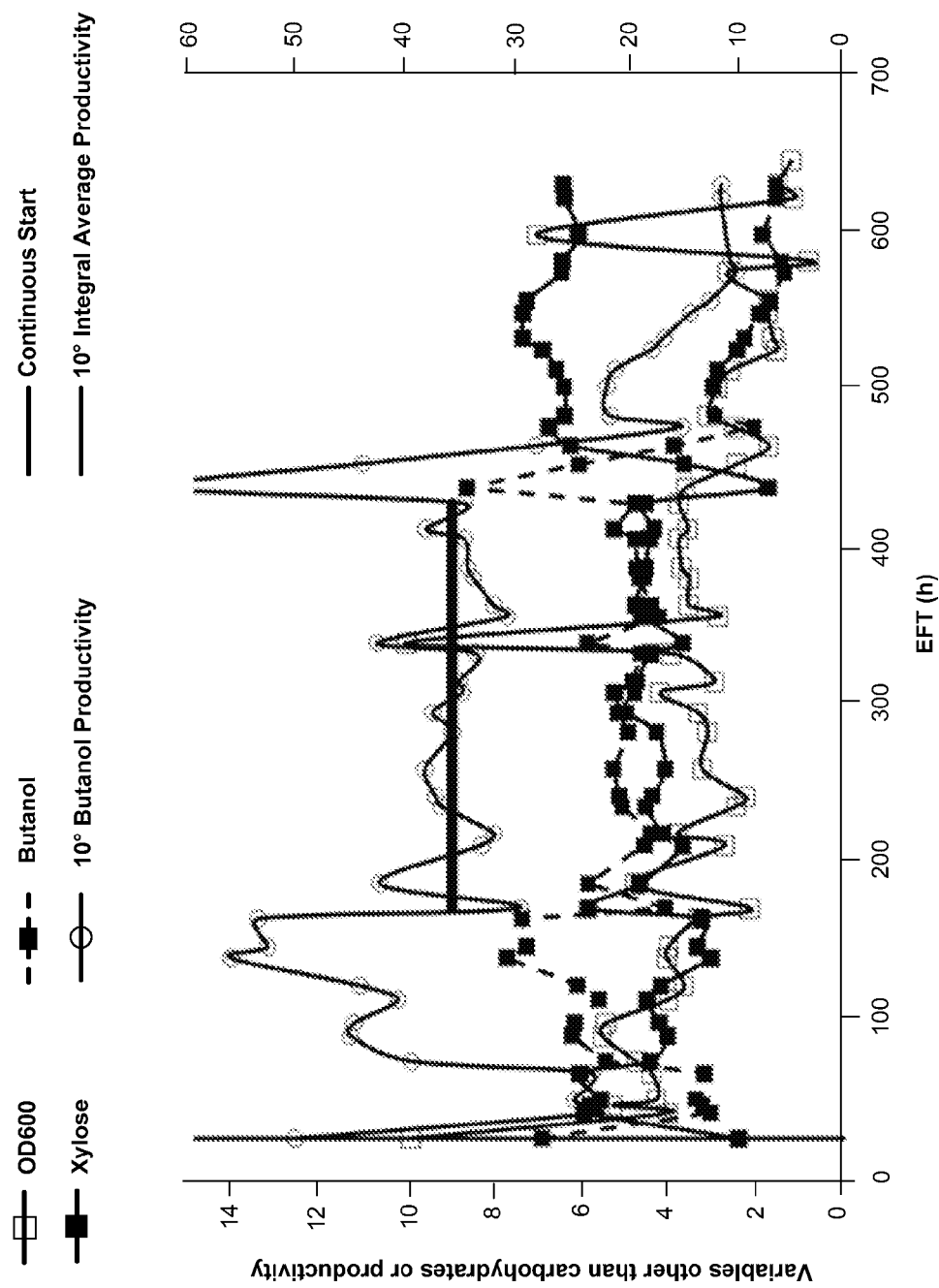
FIG. 11 shows the results of continuous culture of immobilized *Clostridium*, in run no. 2008137 (strain Co-5673 on 4% mixed sugar simulated hydrolysate) as described in Example 1.
Figure 12:
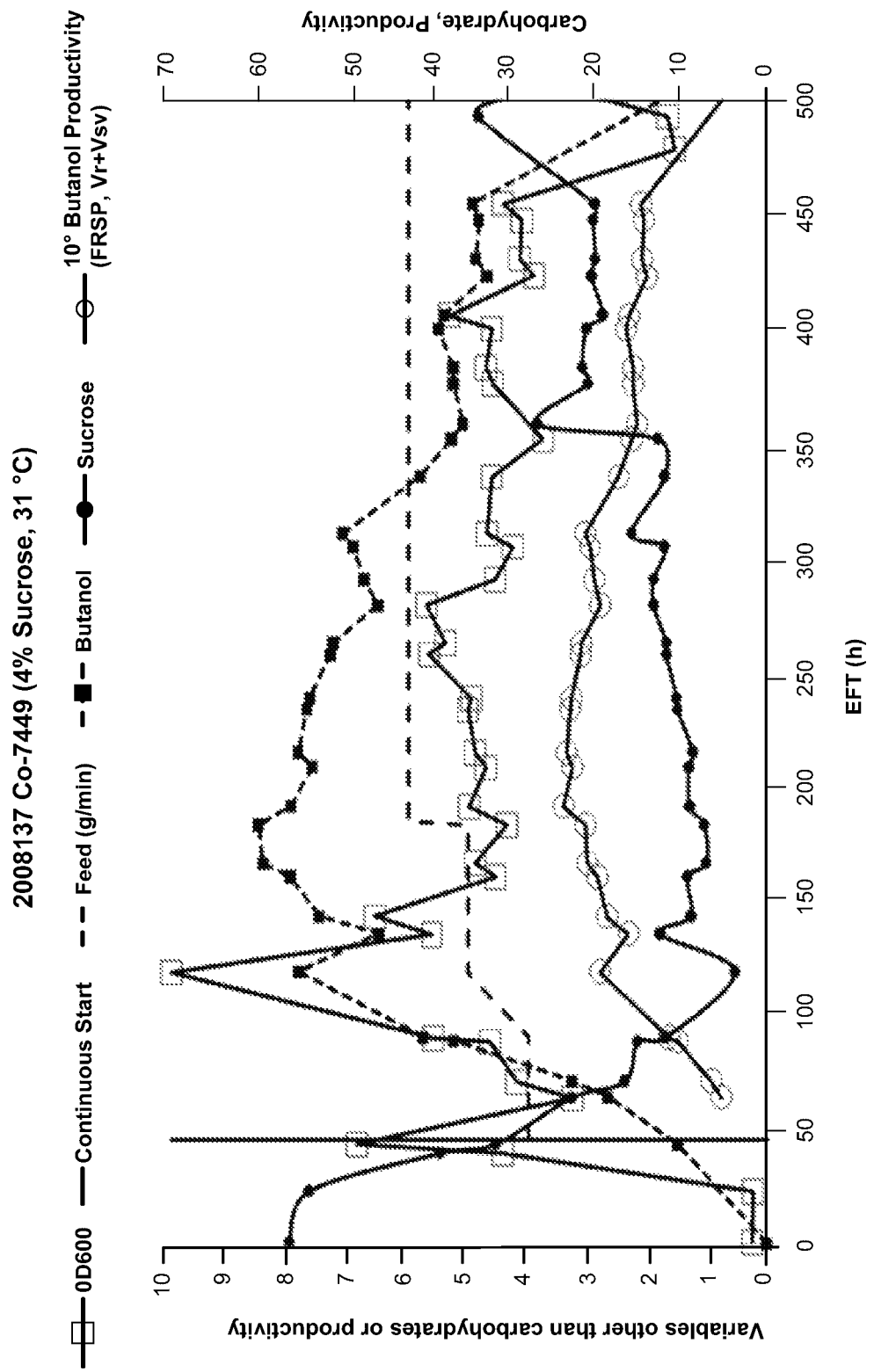
FIG. 12 shows the results of continuous culture of immobilized *Clostridium*, in run no. 2009060 (strain Co-7449 on 4% sucrose) as described in Example 1.

A larger batch slurry process with Duolite A7 resin was used for evaluation of effect of conditioned hydrolysate on butanol titer and yield. The butanol titer and yield on the conditioned hydrolysate were 7.7 g/L and 0.17 g/g sugars converted, respectively. The microorganism did not grow on the unconditioned hydrolysate. The results of HPLC analysis are shown in FIG. 5.

Example 5

Continuous Fermentation of *Clostridium* Immobilized in a 110 Liter Packed Bed Bioreactor for 350 Hours

*Clostridium saccharobutylicum* Co-7449 (PCT/US09/40050) was grown anaerobically in a packed bed bioreactor with 110 L nominal volume and 63.7 L working volume. The L/D ratio of the bioreactor was 8.

The *Clostridium* was immobilized on bonechar. The bonechar particles had a size of 3000 to 5000 microns, with a bulk density of about 0.72/ml. About 100 pounds of bonechar was loaded into the reactor. Immobilization was achieved by first filling the reactor with about 40 L of CP3 media with 4% sucrose and then adding to the reactor 20 L of *Clostridium* broth that had an OD at 600 nm of about 1, and recalculating the contents of the reactor for 24 hours.

The growth medium was essentially identical to P2 medium, as described in Jesse et al. (2002) *Journal of Industrial Microbiology and Biotechnology* 29:117-123, with 4% sucrose as carbohydrate feed.

Continuous culture was achieved after the bioreactor had been inoculated by pumping the growth media at a constant rate into the bottom of the bioreactor and continuously removing broth from the top of the bioreactor in order to maintain a constant liquid level in the bioreactor. Continuous fermentation continued for 350 hours.

The feed rate for the run was initially 800 g/min, was reduced to 400 g/min at about 60 hours, and was increased to 500 g/min at about 143 hours. The average pH was about 4.95 and the average pressure was about 3.24 psi. N2 was added at a rate of 0.7 L/min for the duration of the fermentation. The average butanol titer, productivity, and yield were 3.44 g butanol/L, 1.55 g butanol/L/hr, and 0.172 g butanol/g sucrose, respectively.

Example 6

Conditioning of Hydrolyzed Feedstock with Metal Salts

A hydrolysate was prepared from beetle killed Lodgepole pine using nitric acid as the catalyst for the hydrolysis reaction. The following conditions were used for hydrolysis: nitric acid concentration 0.4-0.5% on a dry wood basis, pH approximately 1.9-2.2, temperature 170° C., time 7 minutes, approximately 25-30% solids in the feed.

The raw hydrolysate was measured out into 100 ml glass bottles to volumes of 50 ml using a pipette. The pH of the hydrolysate samples was then adjusted to pH values in the range of 5.5 to 10 with a 15% solution of ammonium hydroxide.

Aluminum sulfate and ferric chloride were added at concentrations in the range of 3 g/L to 5 g/L and the solutions incubated for about 30 minutes at temperatures in the range of 20° C. to 40° C. The solutions were mixed during the incubation using a magnetic stir plate. The solutions were then filtered through a 0.2 micron filter to separate precipitate from the liquid hydrolysate.

The solutions were then cooled to room temperature if not already at room temperature. The pH of the solutions was then adjusted to 7.2 with nitric acid or ammonium hydroxide. After pH adjustment, 10 ml of each solution was then filtered through a Pall sterile syringe filter with a pore size of 0.2 microns into a 15 ml falcon tube. The solutions were then placed in an anaerobic hood overnight to de-oxygenate.

Media components were added to the de-oxygenated hydrolysate solution at the prescribed concentrations to support microbial growth (i.e., growth media components and trace elements). The tubes were then inoculated with a butanol-producing *Clostridium* strain at a concentration of approximately $5 \times 10^7$ CFU. The conditions used for fermentation were as follows: volume 10 ml, pH approximately 6.8 before inoculation, temperature 30° C.

Aluminum sulfate and ferric chloride were both successful in transforming an otherwise un-fermentable hydrolysate into a fermentable feedstock that supported microbial growth and production of butanol. Under the conditions used for fermentation, aluminum sulfate produced a feedstock that resulted in higher butanol production along with less precipitate in the final product than ferric chloride. The best results for treatment of raw hydrolysate with aluminum sulfate and ferric chloride were at the following conditions: metal salt concentration 3 g/L, pH 9.5, room temperature (about 20° C.). The butanol concentrations after microbial fermentation for 72 hours were 8.64 g/L and 7.69 g/L for aluminum sulfate and ferric chloride, respectively.

Adjustment of hydrolysate pH before metal salt addition was found to be important. For example, a solution adjusted to pH 9 before addition of metal salts did not ultimately support microbial growth. However, adjustment of the solution to pH 9.5 resulted in a conditioned hydrolysate in which the microorganism grew and produced butanol.

Lower temperatures also resulted in lower sugar loss. At room temperature, the sugar loss was only 6%.

Example 7

Hemicellulose Extraction from Wood Chips with Deconstruction of Residual Cellulose Grey stage Lodgepole pine chips, moisture content approximately 24.9%, were screened for debris and passed through a thermomechanical disintegrator in order to ensure (1) adequate acid impregnation throughout the chip for the liberation of hemicellulosic sugars, and (2) to remove some wood extractives.

The disintegrator was a Bauer/Andritz RT Impressifiner, used under the following conditions. Some dilution water was added to saturate the wood chips, steam was added at a delivery pressure of 1.38 bar, residence time was 20 seconds, and the flow restriction at the exit of the RT Impressifiner was set to 1 inch.

A sample of the preliminary pressate was collected. 1.42% (w/w) nitric acid was added to the solid material at the exit of the RT Impressifiner and resulted in a 32-37% (w/w) solids stream. The material was collected in drums, stored at about 10° C. for processing 12-18 hours later. The temperature of the material at the exit of the disintegrator was 60° C., and cooled about 15-20° C. in 15 hours.

The acid impregnated material was then added to a feed hopper for a digestor feeding system. The digestor was a continuous feed, pressure rated, screw conveyor vessel operated nominally at 7.92-6.13 bar (90-110 psig), which corresponds to a steam saturation temperature of 167-176° C. Material was fed at an average rate of 11 ODMT/day to the ~1000 L digestor through a plug screw feeder (PSF) system with a compression ratio of approximately 8:1 or a rotary valve. The liquids to solids ratio feeding the digestor was 2.1:1. The residence time within the digestor was 300-480 seconds.

The liquid pressate from the PSF was measured at a rate of approximately 2 gallons per minute (gpm) (7.6 liters/minute) and contained free nitric acid (pH 1.3), as well as turpentine/tall oil type components (by smell). In some cases, all of the liquid pressate was added back to the digestor. In other cases, a portion of the liquid pressate was added back to the digestor with the balance of the 2 gallons per minute supplied by city water. In other cases, the PSF pressate was discarded and 2 gallons per minute of water were added to the digestor.

Pressure was maintained in the digestor with a 6 inch ball type blow valve. The hydrolysate and residual solids were expanded to atmospheric pressure through a cyclone to separate the vapor from the liquid and solids. Some volatiles were removed in the vent stream. Residual solids were approximately 32% by weight.

A 560 screw press was used to attempt to separate solids from liquids. Very little dewatering was achieved. Average feed solids was measured at about 36% and the residual solids exiting from the screw press was measured to be 36-37%, due to the small average fiber dimension.

Surprisingly, the residual material had very little fiber quality or structure. Microscopic imaging of the residual material showed little distinguishable cellulosic fiber. The fiber had the following characteristics:

| | |
|---|---|
| Length weighted average length (mm) | 0.276 |
| Arithmetic average length (mm) | 0.151 |
| Weight weighted average length (mm) | 0.544 |
| Average width (μm) | 36.14 |
| Surface area (m$^2$/kg) | 1441 |
| Fiber Classifications | |
| % on 14 mesh | 0.5 |
| % on 28 mesh | 1.7 |
| % on 48 mesh | 3.7 |
| % on 100 mesh | 8.2 |
| % on 200 mesh | 9.6 |
| % through 200 mesh | 76.3 |

*% denotes weight fraction retained on the indicated mesh.

The hydrolysate liquor contained significant concentrations of primarily hemicellulose sugars (~75 g/L) in the ratios typical of softwood dilute acid hydrolysis: mannose, xylose, glucose, arabinose, and galactose.

In a follow up experiment, material that had been passed through the disintegrator under conditions of either no acid added or 1.42% (w/w) nitric acid was reacted in a 7.6 liter Parr bomb type reactor. No additional water was added, in order to duplicate as closely as possible the conditions in the digestor (5 minutes, 166° C.). In this run, 750 g of the moist feed (36.8% solids by weight) were added. 450 g of water were also added to the reactor. Live steam was added until the reactor reached the setpoint temperature at which point the blow valve was released (5 minutes) and the material was blown into a blow tank where the pressure was permitted to equilibrate with the environment.

Figure 13:
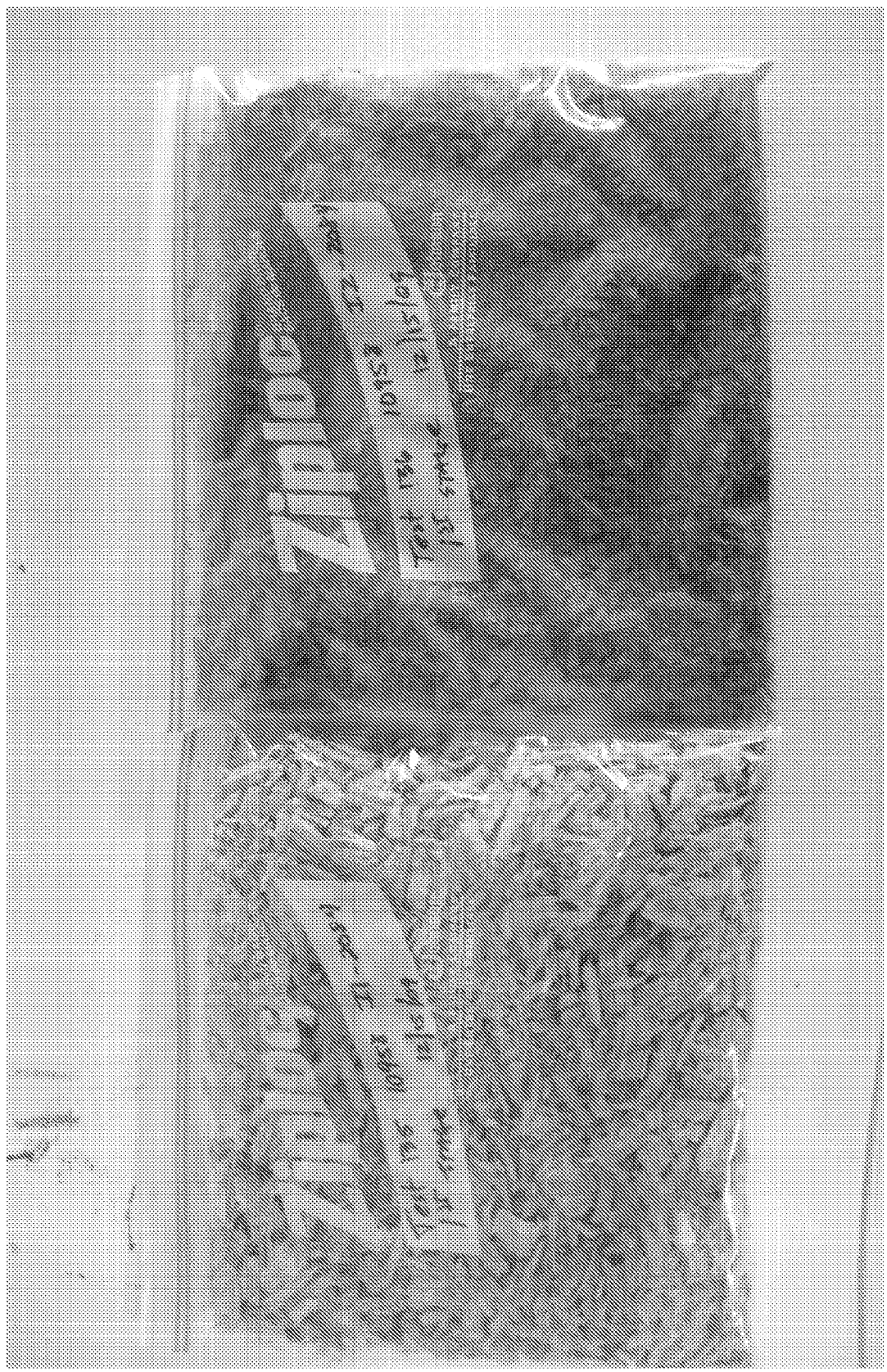
FIG. 13 shows the residual material remaining after performing the hemicellulose extraction procedure described in Example 7 with acid (right hand panel) or water (left hand panel).

The results are shown in FIG. 13. The residual solids from the no acid condition are shown in the photograph on the left, and the residual solids produced with 1.42% nitric acid are shown in the photograph on the right. Visible cellulosic fiber was observed in the no acid sample but not in the nitric acid sample.

Example 8

Hemicellulose Extraction from Wood Chips

Grey stage Lodgepole pine chips, moisture content approximately 31.6%, were passed through a thermomechanical disintegrator, as described in Example 1 except that the wood chips were not screened for debris and the flow restriction at the exit of the disintegrator was 0.5 inch.

0.44% (w/w) nitric acid was added to the solid material at the exit of the RT Impressifiner and resulted in a 33.0% (w/w) solid discharge. The material was fed to a digestor as described in Example 1, with storage from 1 to 12 hours prior to processing. The digestor conditions were as described in Example 1, except the residence time was 360 seconds. No PSF pressate was retained in the process, but water was added to the rotary feeder (~1.9 gpm) parallel to the PSF, the mechanical refiner (post digestor, between the digestor and the blow valve) (~3 gpm), and the discharge cyclone, which is located post blow valve.

The resulting visible fiber quality was greater than in the product described in Example 1, and was effectively dewatered in the screw press. Residual solids were 57.7% by weight.

The fiber had the following characteristics:

| | |
|---|---|
| Length weighted average length (mm) | 0.379 |
| Arithmetic average length (mm) | 0.202 |
| Weight weighted average length (mm) | 0.862 |
| Average width (μm) | 49.72 |
| Surface area (m$^2$/kg) | 1105 |
| Fiber Classifications | |
| % on 14 mesh | 11.6 |
| % on 28 mesh | 18.0 |
| % on 48 mesh | 19.7 |
| % on 100 mesh | 20.2 |
| % on 200 mesh | 7.4 |
| % through 200 mesh | 23.1 |

*% denotes weight fraction retained on the indicated mesh.

The hydrolysate liquor contained significant concentrations of hemicellulose sugars (~43.5 g/L) in the ratios typical of softwood dilute acid hydrolysis: mannose, xylose, glucose, arabinose, and galactose.

Example 9

Continuous Fermentation of *Clostridium* Immobilized in a 1 Liter Packed Bed Bioreactor for 422 Hours with Conditioned Hydrolysate A butanol-producing *Clostridium* strain was grown anaerobically in a packed bed bioreactor with 1 L nominal volume and 670 mL working volume. The L/D ratio of the bioreactor was 3.

The *Clostridium* was immobilized on bonechar. The bonechar particles had a size of 3000 to 5000 microns, with a bulk density of about 0.72/ml. About 1.5 pounds of bonechar was loaded into the reactor. Immobilization was achieved by first filling the reactor with about 670 mL of CP3 media with 6% w/v softwood sugars synthetic mix (20.04% w/w D-glucose, 31.32% w/w D-xylose, 12.88% w/w L-arabinose, 35.76% w/w D-mannose) and then adding to the reactor 60 mL of *Clostridium* broth that had an OD at 600 nm of about 0.8, and recirculating the contents of the reactor for 24 hours.

The initial growth medium as well as the medium used during the continuous part of the fermentation, contained conditioned beetle killed lodgepole pine acid hydrolysate with about 45 g/L sugar, supplemented with P2 medium components and trace elements, except that ammonium was added as ammonium sulfate instead of as ammonium acetate. The hydrolysate was prepared as described in Example 7, and conditioned on Duolite A7 resin at acidic pH.

Continuous culture was started around 21 hours after inoculation by pumping the growth media at a constant rate into the bottom of the bioreactor and continuously removing broth from the top of the bioreactor in order to maintain a constant liquid level in the bioreactor. Continuous fermentation continued for 422 hours.

The feed rate for the run was 8 g/min and N2 was added at a rate of 0.1 L/min for the duration of the fermentation. During the fermentation period between 164 and 422 hours the average pH was about 5.1. The average butanol titer, productivity, and yield were 7.6 g butanol/L, 5.5 g butanol/L/hr, and 0.26 g butanol/g carbohydrate, respectively.

Example 10

Production of Multiple Bioproducts in a Continuous Immobilized Microbial Fermentation

*Clostridium* was grown anaerobically in a packed bed bioreactor with 111.3 L nominal volume and 65.7 L working volume. The L/D ratio of the bioreactor was 5.7.

The *Clostridium* was immobilized on bonechar initially screened with a 5×8 mesh, with a bulk density of about 45 lb/ft3. About 100 pounds of bonechar was loaded into the reactor. Immobilization was achieved by first filling the reactor with about 100 L of fermentation media with 4% by weight softwood hydrolysate, prepared as described in Example 8 and conditioned on Duolite A7 resin at acidic pH, draining approximately 15 L of feed media and then adding to the reactor about 15 L of *Clostridium* broth that had A600 absorbance of about 1. The fermentation broth was circulated for approximately 24 h prior to setting the reactor into continuous operation.

Continuous culture was achieved after the bioreactor had been inoculated by pumping the growth media at a constant rate into the bottom of the bioreactor and continuously removing broth from the top of the bioreactor in order to maintain a constant liquid level in the bioreactor.

The feed rate for the run was about 540 g/min. The average pH was about 5.5 and the average pressure was about 3.4 psi. N2 was added at a rate of 1.0 L/min for the duration of the fermentation. After 106 hours elapsed fermentation time, yield of butanol, acetone, ethanol, acetic acid, and butyric acid were 0.220, 0.050, 0.020, 0.015, and 0.111 g/g sugars converted, respectively. Sugar conversion in the reactor varied throughout the run and was approximately 50-80%.

Example 11

Purification of Biobutanol from Fermentation Broth

Fermentation broth from a continuous culture of immobilized *Clostridium*, grown in a packed bed bioreactor with 111.3 L nominal volume, 73.4 L working or packed bed volume, and L/D ratio (packed section) 5.7, was collected from the bioreactor and pumped into a 500 gallon harvest tank. The residence time in the harvest tank was about 60 h, depending on the bioreactor harvest rate. When sufficient material had been collected, a microfiltration step (2"×3' microfiltration membrane unit, 0.1 um cutoff) was performed to remove cell mass and other debris.

The material was then transferred to a 75 gallon steam heated batch distillation vessel with an insulated, packed overhead 4" column to provide some reflux. The vessel was indirectly heated with steam and the overheads were condensed and collected by a receiver. Vessel pressure was maintained at ambient pressure. Upon discharge from the receiver, the material was decanted and the butanol rich organic phase (60-80% BuOH by weight) was further distilled in a smaller, electrically heated 5-stage Snyder distillation apparatus. The aqueous butanol phase (7-9% BuOH by weight) was discarded rather than subsequently separated. Recovery yield was 12%.

Preliminary analytical results for biobutanol derived from simple sugars (5% hardwood synthetic mix (9.0 g/l glucose, 32.8 g/l xylose, 5.8 g/l arabinose, 3.3 g/l mannose)+1 g/L yeast extract, 2.2 g/L ammonium acetate, 1 g/L $K_2HPO_4$, 0.1 g/L $KH_2PO_4$)), as described in this example, are presented in Table 2.

TABLE 2

Composition of Purified Biobutanol

| Butanol (v/v %) | Water (w/w %) | Acetic Acid (v/v %) | Butyric Acid (v/v %) |
|---|---|---|---|
| 98.2 | 0.67 | 0.03 | 0.03 |

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description and claims should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process for producing a bioproduct, comprising:
   (i) hydrolyzing a carbohydrate-containing feedstock upstream from a bioreactor that comprises a microbial growth medium and a microorganism that is immobilized on a support in the bioreactor, wherein the carbohydrate-containing feedstock is deconstructed prior to hydrolysis; and
   (ii) feeding a resulting hydrolyzed feedstock to the bioreactor,
   wherein the hydrolyzed feedstock comprises carbohydrate molecules that serve as a carbon source for growth of the microorganism,
   wherein the microorganism ferments the hydrolyzed feedstock to produce the bioproduct, and
   wherein the hydrolysis of the feedstock, feeding of the hydrolyzed feedstock to the bioreactor, and production of the bioproduct are continuous.

2. A process according to claim 1, wherein the hydrolyzed feedstock is fed continuously into multiple bioreactors arranged in parallel and/or in series, wherein the bioproduct is produced in each of the multiple bioreactors, wherein the fermentation occurs continuously in the multiple bioreactors, and wherein the multiple bioreactors comprise the same or different microorganism(s).

3. A process according to claim 1, wherein said feedstock is a lignocellulosic material.

4. A process according to claim 3, wherein said lignocellulosic material is pretreated to remove extractives.

5. A process according to claim 4, wherein the pretreatment to remove extractives comprises compression, water extraction, solvent extraction, alkaline extraction, enzymatic treatment, fungal treatment, oxygen treatment, or air drying, wherein the pretreatment occurs prior to or in conjunction with deconstruction.

6. A process according to claim 3, wherein said hydrolysis comprises treatment with nitric acid.

7. A process according to claim 6, wherein said nitric acid hydrolysis comprises a first stage and a second stage, and wherein the second stage hydrolysis is performed at a higher temperature than the first stage.

8. A process according to claim 7, wherein the first and second stage hydrolysates are combined prior to introduction into the bioreactor.

9. A process according to claim 7, wherein the first and second stage hydrolysates are introduced as separate hydrolyzed feedstock streams into separate bioreactors, wherein the first stage hydrolysate is introduced into a first bioreactor and the second stage hydrolysate is introduced into a second bioreactor, wherein the first and second bioreactors comprise the same or different microorganism(s).

10. A process according to claim 9, wherein the first bioreactor comprises a first microorganism and the second bioreactor comprises a second microorganism, wherein the first and second microorganisms are different, and wherein the first microorganism is optimized for growth and/or desired product production on the first stage hydrolysate and the second microorganism is optimized for growth and/or desired product production on the second stage hydrolysate.

11. A process according to claim 7, wherein conditions in the first stage are chosen to achieve hydrolysis of at least about 70% of the hemicellulose in the feedstock, and wherein the conditions in the second stage are chosen to achieve hydrolysis of at least about 40% of the cellulose in the feedstock.

12. A process according to claim 7, wherein flash steam is generated in the second stage hydrolysis, and wherein the flash steam is used to deconstruct the feedstock prior to hydrolysis and/or to provide energy for the first stage hydrolysis.

13. A process according to claim 7, wherein flash steam is generated in the second stage hydrolysis, wherein the flash steam is recompressed, and wherein the recompressed steam is used to provide energy for the first stage hydrolysis and/or a downstream distillation process for product purification.

14. A process according to claim 7, wherein flash steam is generated in the second stage hydrolysis, wherein the flash steam is used to provide energy for a third stage hydrolysis, wherein a temperature of the third stage hydrolysis is lower than a temperature of the second stage hydrolysis, and wherein the lower temperature permits hydrolysis of remaining oligomeric sugar molecules with less degradation than hydrolysis performed at a higher temperature.

15. A process according to claim 3, wherein hydrolysis of the feedstock produces a lignin-containing residue, and wherein the lignin-containing residue is used as an energy source for said process and/or for electricity generation.

16. A process according to claim 3, wherein the lignocellulosic material is wood selected from softwood, hardwood, or a combination thereof.

17. A process according to claim 16, wherein the lignocellulosic material comprises wood chips, sawdust, saw mill residue, or a combination thereof.

18. A process according to claim 3, wherein the lignocelluosic material is from a feedstock source that has been subjected to a disease or infestation.

19. A process according to claim 3, wherein the lignocellulosic material comprises bagasse or straw.

20. A process according to claim 1, wherein said hydrolysis of the feedstock comprises treatment with one or more acid, enzymatic hydrolysis, or autohydrolysis with acetic acid released by the feedstock.

21. A process according to claim 20, wherein the acid comprises one or more acids selected from the group consisting of nitric acid, formic acid, acetic acid, phosphoric acid, hydrochloric acid, and sulfuric acid.

22. A process according to claim 1, wherein hydrolysis comprises treatment with one or more acid, wherein flash steam is generated during the hydrolysis process, and wherein said flash steam is used to provide energy for one or more processes selected from deconstruction of feedstock, further hydrolysis of feedstock, purification of the bioproduct, and recovery of other products of interest.

23. A process according to claim 1, wherein the hydrolyzed feedstock is conditioned to remove inhibitors of microbial growth and/or bioproduct production prior to introduction of the hydrolyzed feedstock into the bioreactor.

24. A process according to claim 1, wherein the microorganism is a *Clostridium* strain.

25. A process according to claim 24, wherein the *Clostridium* strain is derived from a species selected from the group consisting of *Clostridium saccharobutylicum*, *Clostridium saccharoperbutylacetonicum*, *Clostridium acetobutylicum*, *Clostridium beijerinckii*, *Clostridium puniceum*, *Clostridium aurantibutyricum*, *Clostridium tetanomorphum*, *Clostridium thermosaccharolyticum*, *Clostridium butyricum*, *Clostridium cellulolyticum*, *Clostridium phytofermentans*, *Clostridium thermohydrosulfuricum*, *Clostridium thermobutyricum*, *Clostridium thermocellum*, and *Clostridium pasteurianum*.

26. A process according to claim 24, wherein the *Clostridium* strain is an environmental isolate or is derived from an environmental isolate.

27. A process according to claim 1, wherein the immobilized microorganism comprises a biofilm.

28. A process according to claim 1, wherein the bioreactor comprises a packed bed, an expanded bed, or a fluidized bed.

29. A process according to claim 1, wherein the bioproduct comprises a biofuel.

30. A process according to claim 29, wherein the biofuel comprises butanol.

31. A process according to claim 1, wherein bioproduct-containing effluent is continuously withdrawn from the bioreactor, and wherein the process further comprises recovery of the bioproduct from the effluent.

32. A process according to claim 31, wherein the bioproduct comprises butanol, and wherein the recovery comprises distillation to separate butanol from other components of the fermentation medium.

33. A process according to claim 32, wherein butyric acid is recovered in the distillation, and wherein the butyric acid is added to the fermentation medium in the bioreactor, wherein the microorganism converts the butyric acid to butanol.

34. A process according to claim 32, wherein flash steam is generated during hydrolysis of the feedstock and the flash steam provides energy for the distillation.

35. A process according to claim 1, wherein the carbohydrate-containing feedstock is a cellulosic material.

36. A process according to claim 35, wherein the carbohydrate-containing feedstock comprises cellulose and hemicellulose.

37. A process according to claim 1, wherein the deconstruction comprises one or more process selected from presteaming, mechanical grinding, and mechanical explosion.

38. A process according to claim 1, wherein the deconstruction occurs due to one or more natural or intentional causes comprising drought, infestation, fire, or herbicide.

39. A process according to claim 1, wherein the support material in the bioreactor comprises bone char, polypropylene, steel, diatomaceous earth, zeolite, ceramic, engineered thermal plastic, clay brick, concrete, lava rock, wood chips, polyester fiber, glass beads, Teflon, polyetheretherketone, or polyethylene.

40. A process according to claim 1, wherein the bioreactor comprises a packed bed, an expanded bed, or a fluidized bed.

* * * * *